(12) United States Patent
Kerr et al.

(10) Patent No.: US 8,277,650 B2
(45) Date of Patent: Oct. 2, 2012

(54) METHODS AND APPARATUS FOR CENTRIFUGAL LIQUID CHROMATOGRAPHY

(75) Inventors: Robert R. Kerr, Cupertino, CA (US); James D. Whitaker, Santa Clara, CA (US)

(73) Assignee: Terrasep, LLC, Mountain View, CA (US)

(*) Notice: Subject to any disclaimer, the term of this patent is extended or adjusted under 35 U.S.C. 154(b) by 379 days.

(21) Appl. No.: 12/723,089

(22) Filed: Mar. 12, 2010

(65) Prior Publication Data
US 2010/0230353 A1    Sep. 16, 2010

Related U.S. Application Data

(60) Provisional application No. 61/210,118, filed on Mar. 13, 2009, provisional application No. 61/313,215, filed on Mar. 12, 2010.

(51) Int. Cl.
*B01D 15/08* (2006.01)
(52) U.S. Cl. ................ 210/198.2; 210/657
(58) Field of Classification Search .......... 210/635, 210/657, 96.1, 198.2; 73/61.52, 61.56; 422/70
See application file for complete search history.

(56) References Cited

U.S. PATENT DOCUMENTS

| | | | |
|---|---|---|---|
| 3,113,103 A | 12/1963 | Alfred | |
| 3,266,554 A | 8/1966 | Brownrigg | |
| 3,395,093 A | 7/1968 | Liberti | |
| 3,503,712 A | 3/1970 | Sussman | |
| 3,547,547 A * | 12/1970 | Anderson | 356/427 |
| 3,617,557 A | 11/1971 | Giltrow | |
| 3,732,982 A * | 5/1973 | Dunnill et al. | 210/198.3 |
| 3,757,952 A | 9/1973 | Baitsholts et al. | |
| 3,798,459 A * | 3/1974 | Anderson et al. | 250/576 |
| 3,810,545 A | 5/1974 | Filz et al. | |
| 3,813,031 A * | 5/1974 | Anderson | 494/43 |
| 4,139,458 A | 2/1979 | Harrison | |
| 4,146,706 A | 3/1979 | Hisatsuka et al. | |
| 4,153,508 A | 5/1979 | Hisatsuka et al. | |
| 4,235,871 A | 11/1980 | Papahadjopoulos et al. | |
| 4,241,046 A | 12/1980 | Papahadjopoulos et al. | |
| 4,340,675 A | 7/1982 | Johansen | |
| RE31,030 E | 9/1982 | Hisatsuka et al. | |

(Continued)

FOREIGN PATENT DOCUMENTS
GB    1135522    12/1968
(Continued)

OTHER PUBLICATIONS

International Search Report dated Jul. 9, 2010 in PCT Application No. PCT/US10/27179.

(Continued)

*Primary Examiner* — Ernest G Therkorn
(74) *Attorney, Agent, or Firm* — Beyer Law Group LLP

(57) ABSTRACT

Apparatus and methods related to centrifugal liquid chromatography are described. An angular velocity can be simultaneously imparted to a large number of chromatographic enclosures. Via centrifugal forces, a mobile phase fluid including a sample can be driven through a stationary phase within the chromatographic enclosure to perform a chromatographic separation process on components of the sample. The use of centrifugation as a driving force can allow significantly smaller stationary phase particles to be employed as compared to high performance liquid chromatography (HPLC). Further, for an equivalent chromatographic separation process, the use of centrifugation can provide much greater separation efficiencies than HPLC.

23 Claims, 18 Drawing Sheets

U.S. PATENT DOCUMENTS

| | | |
|---|---|---|
| 4,388,193 A | 6/1983 | Buncak |
| 4,388,406 A | 6/1983 | Johansen |
| 4,390,628 A | 6/1983 | Johansen |
| 4,394,149 A | 7/1983 | Szoka, Jr. et al. |
| 4,394,448 A | 7/1983 | Szoka, Jr. et al. |
| 4,422,941 A | 12/1983 | Vaughan, Jr. et al. |
| RE31,664 E | 9/1984 | Hisatsuka et al. |
| 4,614,793 A | 9/1986 | Hughes et al. |
| 4,678,570 A * | 7/1987 | Meszaros et al. .......... 210/198.2 |
| 4,726,904 A | 2/1988 | Ayers |
| 4,797,215 A | 1/1989 | Nyiredy et al. |
| 4,841,045 A | 6/1989 | Kuehne |
| 4,874,601 A | 10/1989 | Flanagan |
| 4,897,477 A | 1/1990 | Kuehne |
| 4,900,435 A | 2/1990 | Anderson |
| 4,900,446 A | 2/1990 | Anderson |
| 4,990,250 A * | 2/1991 | Hellinger ................... 210/198.2 |
| 4,999,105 A * | 3/1991 | Melcher et al. ............ 210/198.2 |
| 5,024,749 A | 6/1991 | Snyder et al. |
| 5,028,531 A | 7/1991 | Ueda et al. |
| 5,039,409 A | 8/1991 | Blaffert et al. |
| 5,081,264 A | 1/1992 | Toki et al. |
| 5,186,824 A | 2/1993 | Anderson et al. |
| 5,208,007 A | 5/1993 | Mills |
| 5,208,160 A | 5/1993 | Kikyotani et al. |
| 5,217,608 A * | 6/1993 | Conway ...................... 210/198.2 |
| 5,240,856 A | 8/1993 | Goffe et al. |
| 5,262,522 A | 11/1993 | Gearing |
| 5,272,075 A | 12/1993 | Anderson et al. |
| 5,273,656 A | 12/1993 | Anderson et al. |
| 5,281,525 A | 1/1994 | Mitsushima et al. |
| 5,332,504 A | 7/1994 | Ito et al. |
| 5,338,676 A | 8/1994 | Mitsushima et al. |
| 5,340,449 A | 8/1994 | Shukla |
| 5,350,683 A | 9/1994 | Sims et al. |
| 5,354,847 A | 10/1994 | Liu et al. |
| 5,364,780 A | 11/1994 | Hershey et al. |
| D354,013 S | 1/1995 | Ninomiya et al. |
| 5,395,521 A | 3/1995 | Jagadeeswaran |
| 5,422,263 A | 6/1995 | Zarlenga, Jr. et al. |
| 5,426,048 A | 6/1995 | Gearing |
| 5,433,847 A | 7/1995 | Rice |
| 5,436,143 A | 7/1995 | Hyman |
| 5,443,734 A | 8/1995 | Fetner et al. |
| 5,444,166 A | 8/1995 | Ecker et al. |
| 5,449,461 A | 9/1995 | Ito |
| 5,455,021 A | 10/1995 | Mills |
| 5,464,937 A | 11/1995 | Sims et al. |
| 5,480,972 A | 1/1996 | Avjioglu et al. |
| 5,484,532 A | 1/1996 | Rice |
| 5,500,362 A | 3/1996 | Robinson et al. |
| 5,508,188 A | 4/1996 | Barsky et al. |
| 5,512,168 A | 4/1996 | Fetner et al. |
| 5,576,195 A | 11/1996 | Robinson et al. |
| 5,589,062 A | 12/1996 | Rice |
| 5,595,898 A | 1/1997 | Robinson et al. |
| 5,602,322 A | 2/1997 | Ecker et al. |
| 5,603,899 A | 2/1997 | Franciskovich |
| 5,608,143 A | 3/1997 | Hershey et al. |
| 5,610,074 A | 3/1997 | Beritashvili |
| 5,618,920 A | 4/1997 | Robinson et al. |
| 5,641,627 A | 6/1997 | Moehle |
| 5,643,787 A | 7/1997 | Barsky et al. |
| 5,650,553 A | 7/1997 | Ecker et al. |
| 5,660,811 A | 8/1997 | Mills |
| 5,665,357 A | 9/1997 | Rose et al. |
| 5,672,481 A | 9/1997 | Minshall et al. |
| 5,676,830 A | 10/1997 | Janik et al. |
| 5,677,180 A | 10/1997 | Robinson et al. |
| 5,684,712 A | 11/1997 | Goffe et al. |
| 5,691,167 A | 11/1997 | Avjioglu et al. |
| 5,693,493 A | 12/1997 | Robinson et al. |
| 5,693,755 A | 12/1997 | Buonagurio et al. |
| 5,698,417 A | 12/1997 | Robinson et al. |
| 5,698,435 A | 12/1997 | Robinson et al. |
| 5,721,108 A | 2/1998 | Robinson et al. |
| 5,736,149 A | 4/1998 | Avjioglu et al. |
| 5,738,985 A | 4/1998 | Miles et al. |
| 5,744,648 A | 4/1998 | Elango et al. |
| 5,756,670 A | 5/1998 | Guss et al. |
| 5,759,807 A | 6/1998 | Breece et al. |
| 5,763,284 A | 6/1998 | Tal et al. |
| 5,766,460 A | 6/1998 | Bergstrom et al. |
| 5,767,064 A | 6/1998 | Sims et al. |
| 5,770,083 A | 6/1998 | Ma et al. |
| 5,834,494 A | 11/1998 | Ham et al. |
| 5,837,135 A * | 11/1998 | Nakamura ................. 210/198.2 |
| 5,837,818 A | 11/1998 | Buonagurio et al. |
| 5,846,818 A | 12/1998 | Robinson et al. |
| 5,851,907 A | 12/1998 | Mohan et al. |
| 5,859,329 A | 1/1999 | Holton et al. |
| 5,859,334 A | 1/1999 | Brugliera et al. |
| 5,871,923 A | 2/1999 | Moehle |
| 5,874,251 A | 2/1999 | Zarlenga, Jr. et al. |
| 5,888,775 A | 3/1999 | Tal et al. |
| 5,900,152 A | 5/1999 | Janik et al. |
| 5,907,086 A | 5/1999 | Neill et al. |
| 5,916,745 A | 6/1999 | Cook et al. |
| 5,923,431 A | 7/1999 | Masterson et al. |
| 5,952,544 A | 9/1999 | Browse et al. |
| 5,976,861 A | 11/1999 | Guss et al. |
| 5,981,171 A | 11/1999 | Kuhns |
| 5,981,187 A | 11/1999 | Cook et al. |
| 6,013,496 A | 1/2000 | Cook et al. |
| 6,037,128 A | 3/2000 | Ranjekar et al. |
| 6,066,503 A | 5/2000 | Graham et al. |
| 6,080,920 A | 6/2000 | Holton |
| 6,091,000 A | 7/2000 | Haynes |
| 6,095,202 A | 8/2000 | Colon et al. |
| 6,120,767 A | 9/2000 | Robinson et al. |
| 6,129,840 A * | 10/2000 | Kitaoka ..................... 210/198.2 |
| 6,143,866 A | 11/2000 | Brewer et al. |
| 6,156,178 A | 12/2000 | Mansfield et al. |
| 6,156,496 A | 12/2000 | Miles et al. |
| 6,174,531 B1 | 1/2001 | Zhang et al. |
| 6,180,778 B1 | 1/2001 | Bastian et al. |
| 6,204,023 B1 | 3/2001 | Robinson et al. |
| 6,224,761 B1 | 5/2001 | Tanimura |
| 6,233,093 B1 | 5/2001 | Arnold et al. |
| 6,265,186 B1 | 7/2001 | Swinkels et al. |
| 6,337,021 B1 | 1/2002 | Ma et al. |
| 6,355,439 B1 | 3/2002 | Chung et al. |
| 6,383,393 B1 | 5/2002 | Colpan et al. |
| 6,413,521 B1 | 7/2002 | McMichael-Phillips et al. |
| 6,423,685 B1 | 7/2002 | Drummond et al. |
| 6,440,705 B1 | 8/2002 | Stanton, Jr. et al. |
| 6,451,369 B1 | 9/2002 | Triantafyllou |
| 6,458,945 B1 | 10/2002 | Stanton, Jr. et al. |
| 6,464,882 B1 | 10/2002 | Prior et al. |
| 6,465,233 B1 | 10/2002 | Knauseder et al. |
| 6,475,392 B2 | 11/2002 | Tanimura |
| 6,500,631 B1 | 12/2002 | Schindler et al. |
| 6,500,650 B1 | 12/2002 | Stanton, Jr. et al. |
| 6,503,398 B2 | 1/2003 | Ma et al. |
| 6,504,023 B1 | 1/2003 | Sims et al. |
| 6,521,740 B1 | 2/2003 | Sims et al. |
| 6,533,912 B2 | 3/2003 | Mansfield et al. |
| 6,534,638 B1 | 3/2003 | Graham et al. |
| 6,541,610 B1 | 4/2003 | Smith |
| 6,541,620 B1 | 4/2003 | Brewer et al. |
| 6,566,059 B1 | 5/2003 | Stanton, Jr. et al. |
| 6,576,137 B1 * | 6/2003 | Ma ............................... 210/657 |
| 6,579,674 B2 | 6/2003 | Miles et al. |
| 6,582,923 B2 | 6/2003 | Stanton, Jr. et al. |
| 6,600,094 B1 | 7/2003 | Cho et al. |
| 6,623,961 B2 | 9/2003 | Miles et al. |
| 6,641,783 B1 * | 11/2003 | Pidgeon et al. ................. 422/70 |
| 6,652,852 B1 | 11/2003 | Robinson et al. |
| 6,667,152 B2 | 12/2003 | Miles et al. |
| 6,774,285 B2 | 8/2004 | Brugliera et al. |
| 6,777,179 B2 | 8/2004 | Miles et al. |
| 6,787,638 B1 | 9/2004 | Watkins et al. |
| 6,812,015 B1 | 11/2004 | Klumpp et al. |
| 6,818,756 B2 | 11/2004 | Sano et al. |
| 6,824,976 B1 | 11/2004 | Miles et al. |
| 6,825,009 B2 | 11/2004 | Stanton, Jr. et al. |
| 6,893,625 B1 | 5/2005 | Robinson et al. |

| | | |
|---|---|---|
| 6,913,898 B2 | 7/2005 | Schindler et al. |
| 6,942,804 B2 | 9/2005 | Herman |
| 6,946,250 B2 | 9/2005 | Bastian et al. |
| 6,991,939 B2 | 1/2006 | Walt et al. |
| 7,022,673 B2 | 4/2006 | Drummond et al. |
| 7,045,284 B2 | 5/2006 | Miles et al. |
| 7,074,916 B2 | 7/2006 | Bastian et al. |
| 7,115,716 B2 | 10/2006 | Watkins |
| 7,192,767 B2 | 3/2007 | Buchberger et al. |
| 7,285,383 B2 | 10/2007 | Miles et al. |
| 7,309,579 B2 | 12/2007 | Schindler et al. |
| 7,347,943 B2 | 3/2008 | Herman |
| 7,351,333 B2 * | 4/2008 | Hawes et al. ............... 210/198.2 |
| 7,354,611 B1 | 4/2008 | Ferkovich et al. |
| 7,815,799 B2 * | 10/2010 | Pfeiffer ....................... 210/198.2 |
| 2001/0053554 A1 | 12/2001 | Mansfield et al. |
| 2002/0022231 A1 | 2/2002 | Vasil |
| 2002/0045187 A1 | 4/2002 | Bogoch |
| 2002/0081367 A1 | 6/2002 | Triantafyllou |
| 2002/0081619 A1 | 6/2002 | Bastian et al. |
| 2002/0084222 A1 * | 7/2002 | Brann ............................ 210/656 |
| 2002/0086819 A1 | 7/2002 | Drummond et al. |
| 2002/0137161 A1 | 9/2002 | Manstein et al. |
| 2002/0142974 A1 | 10/2002 | Kohn et al. |
| 2002/0150914 A1 | 10/2002 | Andersen et al. |
| 2002/0160948 A1 | 10/2002 | Pilon et al. |
| 2002/0160977 A1 | 10/2002 | Miles et al. |
| 2002/0165194 A1 | 11/2002 | Miles et al. |
| 2002/0182656 A1 | 12/2002 | Bird et al. |
| 2002/0182705 A1 | 12/2002 | Drummond et al. |
| 2003/0032204 A1 | 2/2003 | Walt et al. |
| 2003/0054433 A1 | 3/2003 | Schindler et al. |
| 2003/0060616 A1 | 3/2003 | Sims et al. |
| 2003/0078398 A1 | 4/2003 | Graham et al. |
| 2003/0082736 A1 | 5/2003 | Smith |
| 2003/0087398 A1 | 5/2003 | Stanton, Jr. et al. |
| 2003/0096343 A1 | 5/2003 | Robinson et al. |
| 2003/0096416 A1 | 5/2003 | Sano et al. |
| 2003/0099962 A1 | 5/2003 | Schernthaner et al. |
| 2003/0104611 A1 | 6/2003 | Johnston et al. |
| 2003/0134290 A1 | 7/2003 | Stanton, Jr. et al. |
| 2003/0144226 A1 | 7/2003 | Miles et al. |
| 2003/0198638 A1 | 10/2003 | Watkins |
| 2003/0207249 A1 | 11/2003 | Beske et al. |
| 2003/0224389 A1 | 12/2003 | Bastian et al. |
| 2003/0232978 A1 | 12/2003 | Seeberger et al. |
| 2004/0038316 A1 | 2/2004 | Kaiser et al. |
| 2004/0053405 A1 | 3/2004 | Buchberger et al. |
| 2004/0076637 A1 | 4/2004 | Delmedico et al. |
| 2004/0091945 A1 | 5/2004 | Fitzer-Attas et al. |
| 2004/0122214 A1 | 6/2004 | Bray et al. |
| 2004/0137512 A1 | 7/2004 | Horii |
| 2004/0248077 A1 | 12/2004 | Rodriguez Rilo et al. |
| 2004/0254140 A1 | 12/2004 | Miles et al. |
| 2005/0003390 A1 | 1/2005 | Axenovich et al. |
| 2005/0003469 A1 | 1/2005 | Watkins et al. |
| 2005/0020498 A1 | 1/2005 | Flores et al. |
| 2005/0036993 A1 | 2/2005 | Kohn et al. |
| 2005/0053972 A1 | 3/2005 | Stanton, Jr. |
| 2005/0066380 A1 | 3/2005 | Herring et al. |
| 2005/0080006 A1 | 4/2005 | Lin et al. |
| 2005/0081264 A1 | 4/2005 | Brugliera et al. |
| 2005/0123563 A1 | 6/2005 | Doranz et al. |
| 2005/0163708 A1 | 7/2005 | Robinson et al. |
| 2005/0197297 A1 | 9/2005 | Drummond et al. |
| 2005/0227308 A1 | 10/2005 | Schindler et al. |
| 2005/0238658 A1 | 10/2005 | Maskell et al. |
| 2005/0250100 A1 | 11/2005 | Hayashizaki et al. |
| 2005/0265975 A1 | 12/2005 | Miles et al. |
| 2006/0099171 A1 | 5/2006 | Tone et al. |
| 2006/0188897 A1 | 8/2006 | Charles et al. |
| 2006/0193874 A1 | 8/2006 | Jones |
| 2006/0216751 A1 | 9/2006 | Boschetti et al. |
| 2006/0223072 A1 | 10/2006 | Boyes et al. |
| 2006/0223073 A1 | 10/2006 | Boyes et al. |
| 2006/0228366 A1 | 10/2006 | Watkins |
| 2006/0233825 A1 | 10/2006 | Jayappa et al. |
| 2006/0233832 A1 | 10/2006 | Melber |
| 2006/0243665 A1 | 11/2006 | Couillard et al. |
| 2006/0247416 A1 | 11/2006 | Delmedico et al. |
| 2006/0251661 A1 | 11/2006 | Galili |
| 2006/0269629 A1 | 11/2006 | Bates et al. |
| 2006/0275868 A1 | 12/2006 | Smith |
| 2007/0009994 A1 | 1/2007 | Horii |
| 2007/0020706 A1 | 1/2007 | Gorodeski et al. |
| 2007/0034052 A1 | 2/2007 | Vanheusden et al. |
| 2007/0041932 A1 | 2/2007 | Jeong et al. |
| 2007/0060513 A9 | 3/2007 | Drummond et al. |
| 2007/0135349 A1 | 6/2007 | Drummond et al. |
| 2007/0160644 A1 | 7/2007 | Kenan et al. |
| 2007/0166350 A1 | 7/2007 | Hamilton et al. |
| 2007/0218470 A1 | 9/2007 | Miles et al. |
| 2007/0218553 A1 | 9/2007 | Rodriguez Rilo et al. |
| 2007/0244165 A1 | 10/2007 | Fischer et al. |
| 2007/0248491 A1 | 10/2007 | Brann |
| 2007/0276131 A1 | 11/2007 | Ferre et al. |
| 2007/0290175 A1 | 12/2007 | Kim |
| 2008/0015138 A1 | 1/2008 | Hamilton et al. |
| 2008/0032924 A1 | 2/2008 | East et al. |
| 2008/0034921 A1 | 2/2008 | Vanheusden et al. |
| 2008/0063637 A1 | 3/2008 | Tsichlis et al. |
| 2008/0145379 A1 | 6/2008 | Graham et al. |
| 2008/0207422 A1 * | 8/2008 | Hawes et al. .................. 494/50 |
| 2010/0276351 A1 * | 11/2010 | Ito .............................. 210/198.2 |

FOREIGN PATENT DOCUMENTS

WO  WO 2004/087931  10/2004

OTHER PUBLICATIONS

Written Opinion dated Jul. 9, 2010 in PCT Application No. PCT/US10/27179.

International Search Report dated Jul. 9, 2010 from International Application No. PCT/US 10/27179.

Written Opinion dated Jul. 9, 2010 from International Application No. PCT/US 10/27179.

Scott et al., "Centrifugal Elution Chromatography with Eluate Monitoring", Journal of Chromatography, 99, 1974, pp. 35-42.

Shumate, II et al., "Centrifugal System for Affinity Chromatography with Eluate Monitoring", Clinical Chemistry, vol. 22, No. 9, 1996.

* cited by examiner

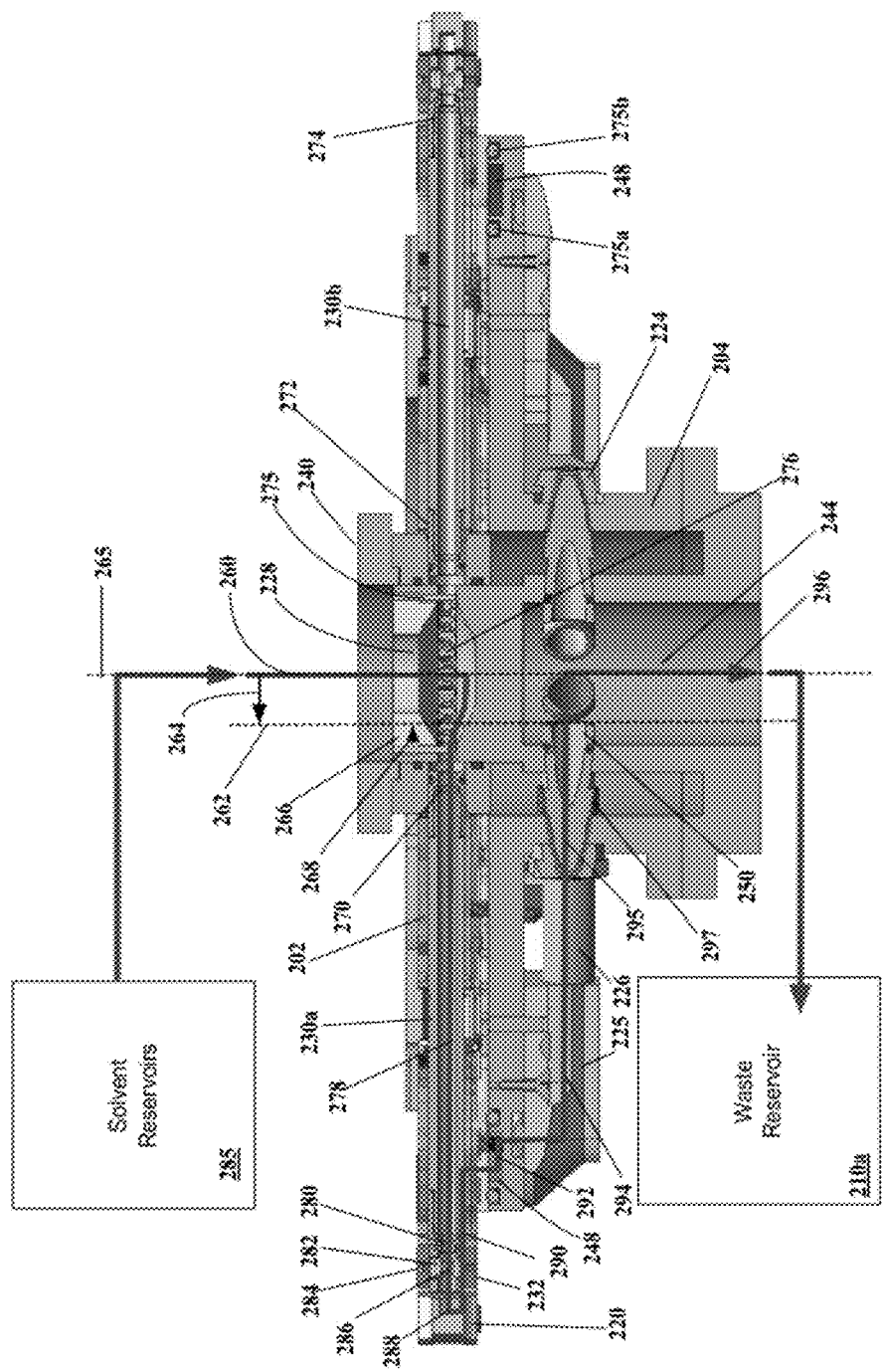

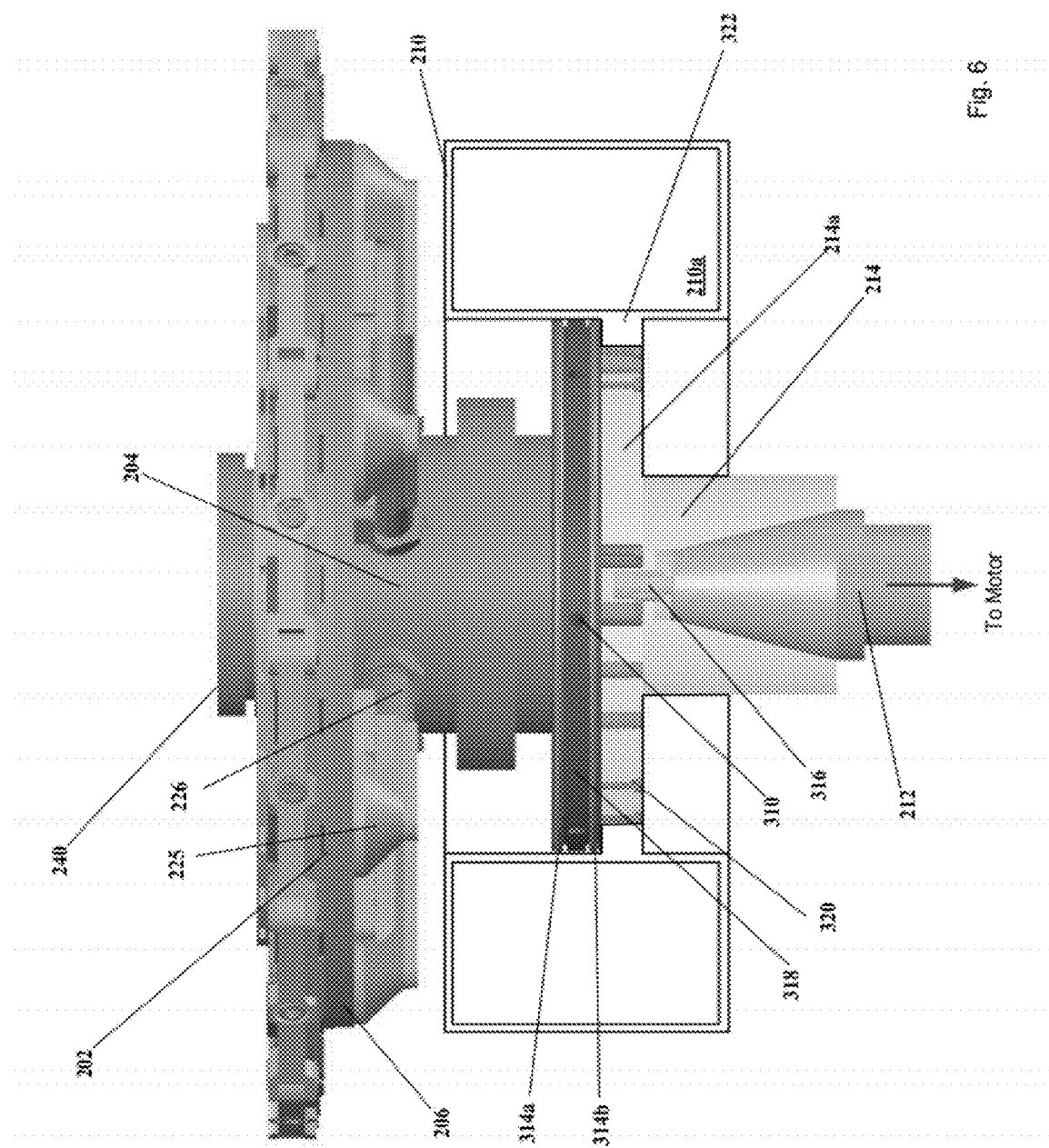

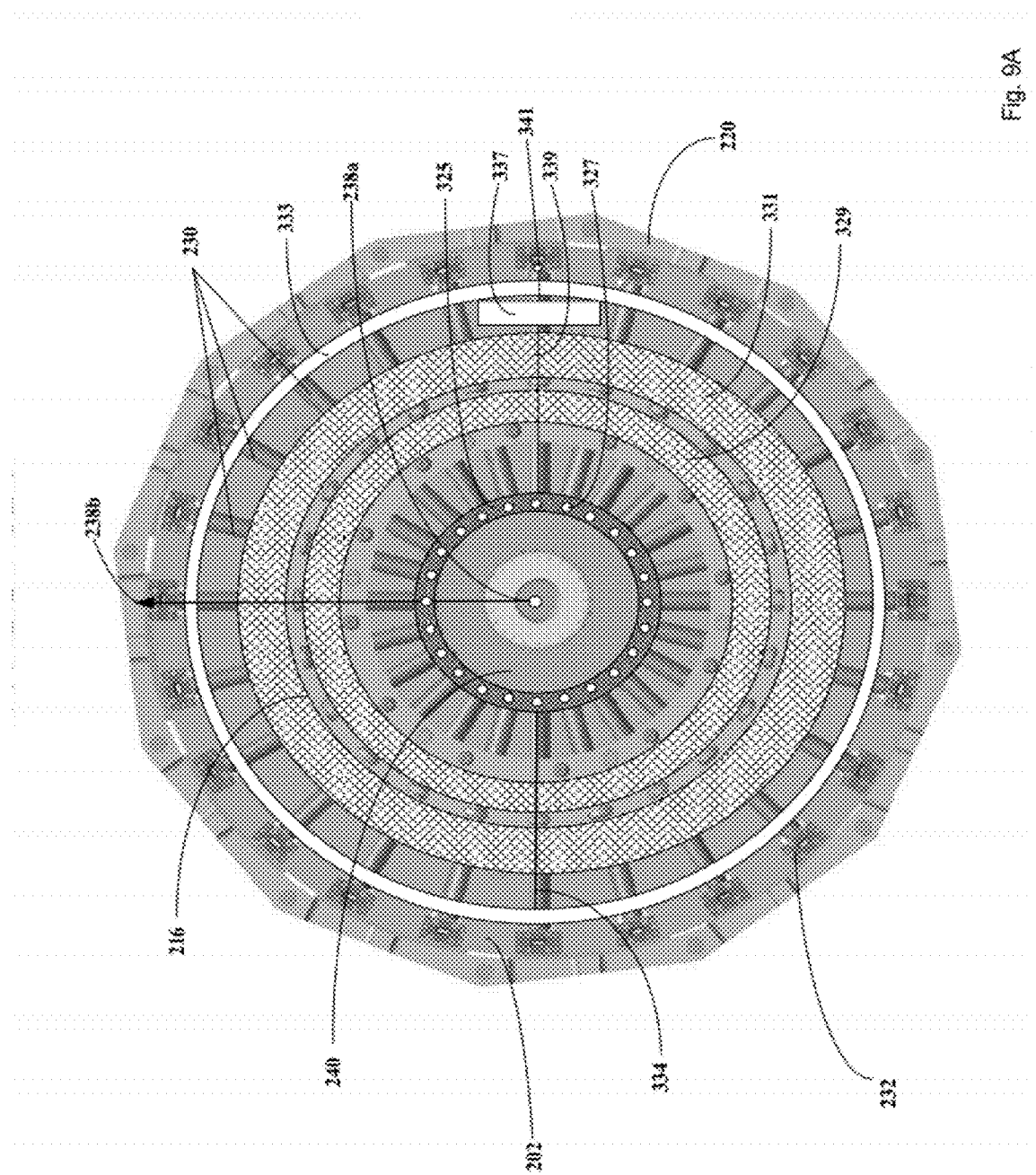

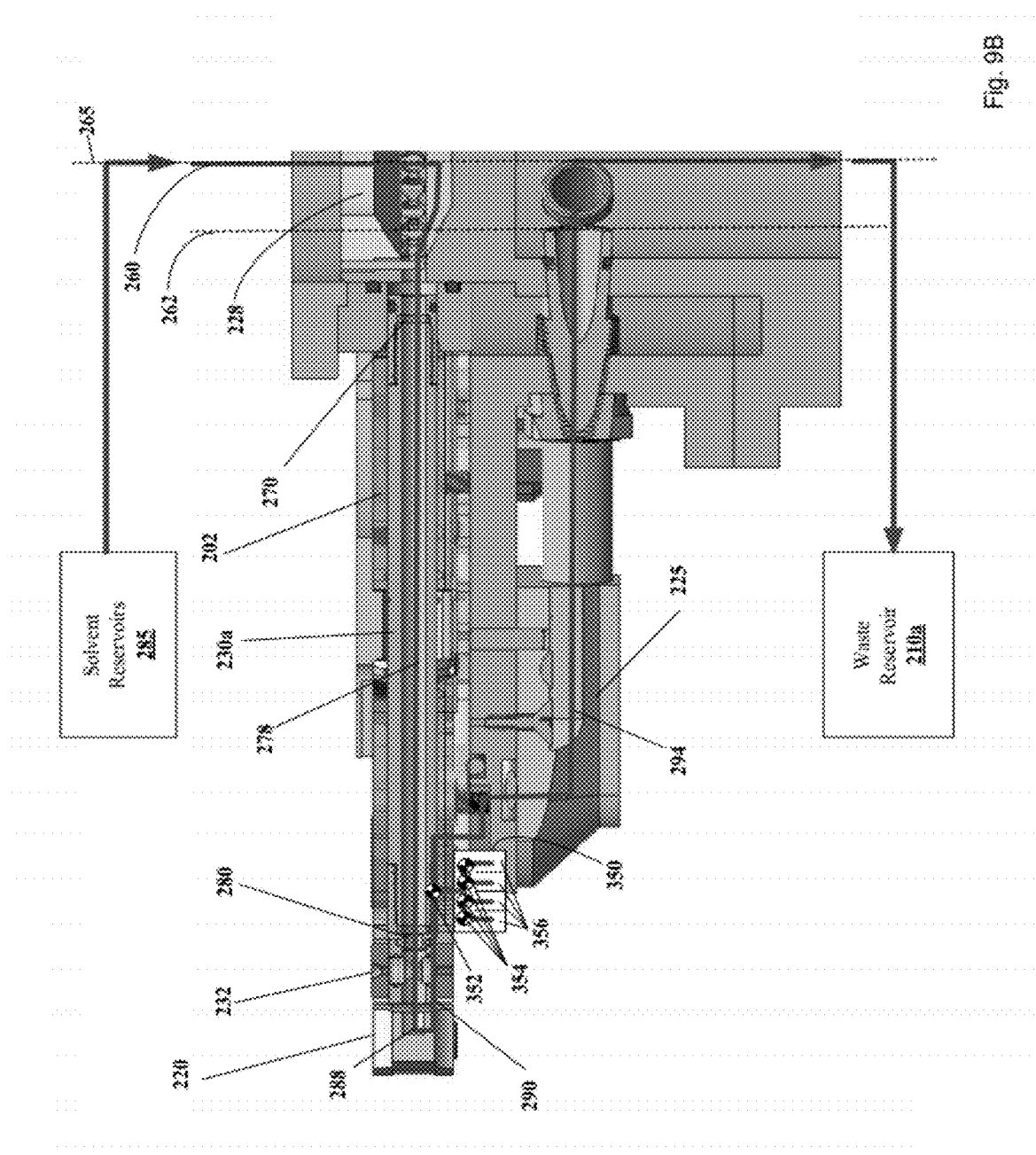

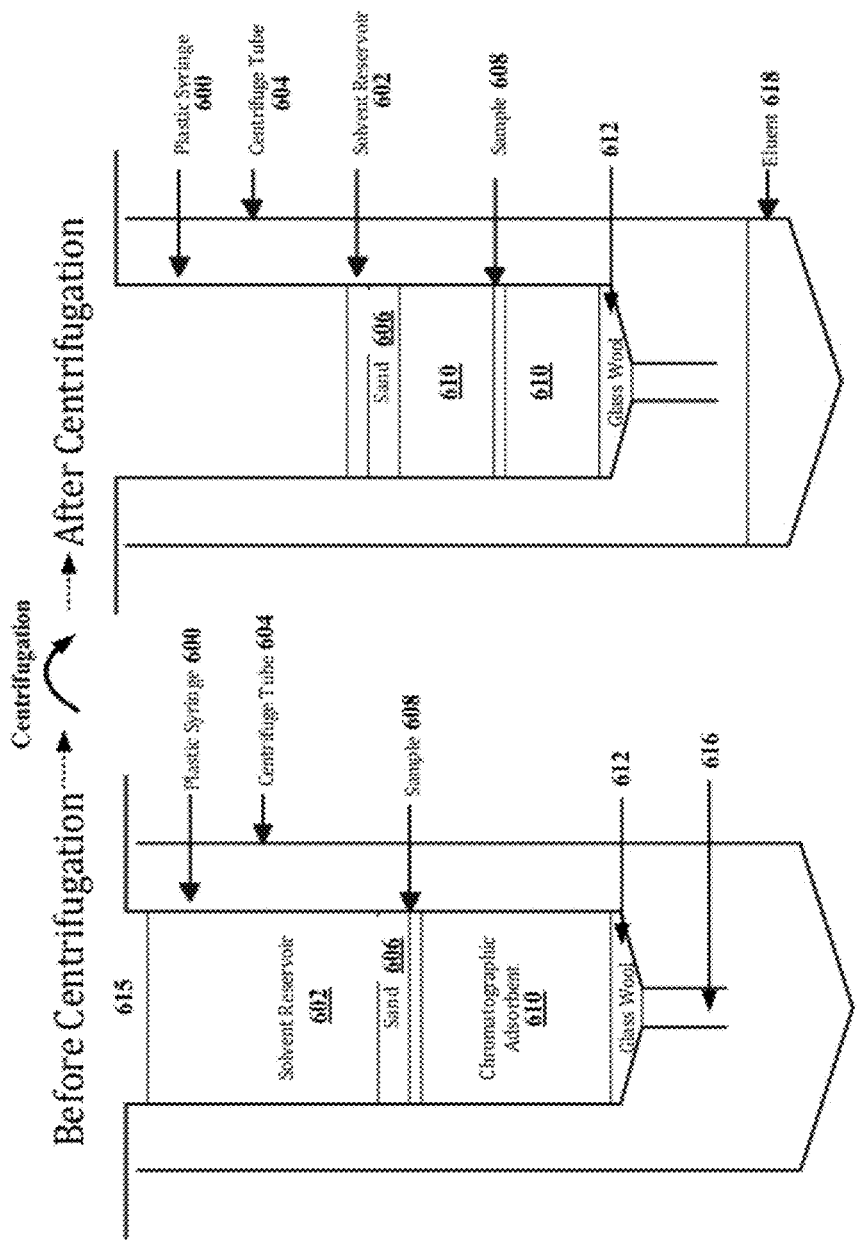

METHODS AND APPARATUS FOR CENTRIFUGAL LIQUID CHROMATOGRAPHY

CROSS REFERENCE TO RELATED APPLICATIONS

This application claims priority under 35 U.S.C. §119(e) to U.S. Provisional Patent Application Ser. No. 61/210,118, entitled "Centrifugal Column Chromatograph System," by Kerr et al. filed Mar. 13, 2009, which is incorporated herein in its entirety and for all purposes. This application also claims priority under 35 U.S.C. §119(e) to U.S. Provisional Patent Application Ser. No. 61/313,215, entitled "Methods and Apparatus for Centrifugal Liquid Chromatography," by Kerr et al. filed Mar. 12, 2010, which is incorporated herein in its entirety and for all purposes.

FIELD OF THE INVENTION

The described embodiments relate generally to systems for performing liquid chromatography. More particularly, the present embodiments relate to methods and apparatus for performing liquid chromatography in a column subject to centrifugal forces.

DESCRIPTION OF THE RELATED ART

Chromatography is a tool for practicing chemists as well as others who are applying chemistry in their own discipline. Chromatography is widely used in and essential to the petroleum industry, food industry, pharmaceutical industry, medicine (e.g., diagnostics), and many others. Chromatography is a separation process. During the chromatographic process, the constituents of a mixture can be physically separated from one another. The physically separated constituents can be analyzed, such as for the purposes of identification. Also, the separated constituents can be collected and utilized for other purposes, such as for use as a component in forming another chemical composition.

Two important aspects of chromatography are separation efficiency and throughput. In the chromatographic process, separation efficiency relates to the ability of the process to separate constituents of a mixture such that the constituents can be distinguished from one another and their chemical identity can be established and collected if desired. A consequence of inadequate separation efficiency in a chromatographic process is an inability to either identify or collect particular constituents of the mixture on which the chromatographic process is being performed. Throughput relates to how long a chromatographic process takes and when a separated constituent is collected, how long it takes to gather a particular amount of the constituent. Typically, as throughput times increase the costs of utilizing a chromatographic process and an associated chromatographic system increase.

A commonly used methodology to perform chromatographic separation is high-performance liquid chromatography (HPLC). Currently, in liquid chromatography, chromatographic systems employing HPLC provide some of the best separation efficiencies and throughput times. HPLC uses pressure as a driving force to move a liquid including a mixture of constituents to be separated through a bed of particles. When a liquid is moved through the bed of particles, interactions between the bed of particles and the liquid can separate the constituents of the liquid from one another.

To improve separation efficiency, it is desirable to use smaller particle sizes within the bed of particles. However, as the particle size decreases, throughput times can increase if the liquid is not efficiently moved through the bed of particles. In HPLC, further gains in separation efficiency are currently limited by the use of pressure as a driving force. To employ a particle size of about 2 micrometers in diameter and obtain a sufficient throughput time, in HPLC, pressures of about 10,000 PSI are required. It is expected that increasing pressures beyond this level will be of limited benefit because at greater pressure levels the particles tend to be crushed and the costs associated with constructing and maintaining a system that provides the greater pressure levels are prohibitive. Therefore, there is a need for improved methods and apparatus of performing liquid chromatography that can provide better separation efficiency and throughput without the limitations of HPLC.

SUMMARY OF THE DESCRIBED EMBODIMENTS

This paper describes various embodiments that relate to systems, methods, and apparatus for providing centrifugal liquid chromatography. A rotor with one or more chromatographic enclosures is provided. Each chromatographic enclosure can be arranged to contain a chromatographic stationary phase and to provide a flow path through the chromatographic stationary phase. Via centrifugal forces, a mobile phase fluid including a sample can be driven through the chromatographic stationary phase within the chromatographic enclosure to perform a chromatographic separation process on components of the sample. Introduction of the sample can be controlled to allow a flow on the rotor to reach a steady-state condition prior to sample introduction. The use of centrifugation as a driving force can allow significantly smaller stationary phase particles to be employed as compared to high performance liquid chromatography (HPLC). Further, for an equivalent chromatographic separation process, the use of centrifugation can provide much greater separation efficiencies than HPLC.

One aspect is generally characterized as a centrifugal chromatographic system. The centrifugal chromatographic system includes 1) a chromatographic enclosure; 2) a rotor that carries the chromatographic enclosure where the rotor is configured to rotate the chromatographic enclosure; and 3) a sample introduction mechanism in fluid communication with the chromatographic enclosure. The sample introduction mechanism is arranged to introduce a sample fluid to the chromatographic enclosure while the rotor is rotating. Further, the sample introduction mechanism is configured to receive a sample introduction signal and to trigger the introduction of the sample fluid in response to receiving the sample introduction signal. In a particular embodiment, a controller is coupled to the sample introduction mechanism where the controller is arranged to automatically trigger the introduction of the sample fluid. In various embodiments, the sample introduction mechanism and/or the controller can be carried on the rotor.

Another aspect is generally characterized as centrifugal column chromatographic system. The centrifugal column chromatographic system includes 1) a rotor configured to rotate about an axis; 2) a number of chromatographic column enclosures carried by the rotor and 3) a sample introduction mechanism in fluid communication with at least a selected one of the chromatographic column enclosures and 4) an eluent reservoir carried by the rotor, in fluid communication with the number of chromatographic enclosures for receiving fluids eluted from the plurality of chromatographic enclosures.

In various embodiments, each chromatographic column enclosure is arranged to contain an associated chromatographic stationary phase and to facilitate transmission of a fluid through the chromatographic stationary phase contained within the chromatographic column enclosure. The fluid is driven generally axially through the chromatographic column enclosure including through the chromatographic stationary phase via centrifugal force generated from the rotation of the rotor. The sample introduction mechanism is arranged to introduce a sample fluid to the selected chromatographic column enclosures while the rotor is rotating.

Yet another aspect is generally characterized as a centrifugal chromatographic system. The centrifugal chromatographic system includes 1) a rotor configured to rotate about an axis; 2) at least one chromatographic enclosure carried by the rotor; and 3) a mixing chamber carried by the rotor and arranged to mix a mobile phase fluid with a sample on the rotor to create a mixed fluid. The mixing chamber utilizes the rotation of a component carried by the rotor to enhance the mixing of the sample with the mobile phase fluid. Further, the mixing chamber is typically located upstream of the chromatographic enclosures. In various embodiments, the centrifugal chromatographic system can also include a mobile phase fluid reservoir in fluid communication with the mixing chamber; and a sample introduction mechanisms in fluid communication with the mixing chamber where the mobile phase fluid reservoir and the sample introduction mechanism may be located either on or off the rotor.

A further aspect is generally characterized as a chromatographic system. The chromatographic system can include 1) a chromatographic enclosure where chromatographic enclosure is arranged to contain an associated chromatographic stationary phase and to facilitate transmission of a fluid through the chromatographic stationary phase contained within the chromatographic enclosure; 2) a rotor that carries the chromatographic enclosure wherein the rotor is configured to rotate the chromatographic enclosure at an angular velocity such that fluid is driven through chromatographic enclosure including through the chromatographic stationary phase via centrifugal force; and 3) a fluid enclosure including a first portion configured to remain stationary while the rotor is rotating and a second portion, carried on the rotor, configured to rotate with the rotor wherein the fluid enclosure is in fluid communication with the chromatographic enclosure.

In one embodiment, the chromatographic system can include a fluid delivery mechanism in fluid communication with the chromatographic enclosure configured to facilitate the delivery of a mobile phase fluid to the chromatographic enclosure. The fluid delivery mechanism includes a first portion configured to remain stationary while the rotor is rotating and a second portion carried on the rotor and configured to rotate with the rotor. The fluid delivery mechanism is arranged so that fluid can be passed from the first portion to the second portion of the fluid delivery mechanism while the rotor is rotating.

One aspect is generally characterized as a centrifugal chromatographic system. The centrifugal chromatographic system includes 1) a rotor including a chromatographic enclosure carried by the rotor; and 2) a gas bearing proximate to the rotor wherein the gas bearing is arranged to stabilize the rotor while it is rotating. The system can also include a containment structure surrounding the rotor; and a plurality of rotor support structures that are supported by the containment structure. The rotor support structures can each include a gas bearing where the gas bearings cooperate to help stabilize the rotor while the rotor is rotating An additional aspect is generally characterized as chromatographic system. The system can include 1) a plurality of chromatographic enclosures, carried on the rotor, each chromatographic enclosure being arranged to contain an associated chromatographic stationary phase and to facilitate transmission of a fluid through the chromatographic stationary phase contained within the chromatographic enclosure where the fluid is driven through the chromatographic stationary phase and towards an outer perimeter of the rotor via centrifugal force generated from the rotation of the rotor; and 2) a plurality of links arranged around the outer perimeter of the rotor each link configured for connection with two other links to form an unbroken chain to be around the outer perimeter of the rotor; wherein one or more of the links includes a flow path arranged to i) receive the fluid moving toward the outer perimeter and ii) redirect the fluid inwardly away from the outer perimeter.

Another aspect is generally characterized as a centrifugal chromatographic system. The system includes 1) a rotor configured to rotate about an axis; 2) a chromatographic enclosure carried on the rotor, said chromatographic enclosure being arranged to contain an associated chromatographic stationary phase and to facilitate transmission of a fluid through the chromatographic stationary phase contained within the chromatographic enclosure, wherein the fluid is driven through the chromatographic stationary phase via centrifugal force generated from the rotation of the rotor; and 3) a flow cell in fluid communication with the chromatographic enclosure, the flow cell including a flow window, wherein an inner cross sectional area of a flow path through the chromatographic enclosure and the flow cell is substantially constant starting at a location in the chromatographic stationary phase of the chromatographic enclosure and progressing past the flow window.

A further aspect can be generally characterized as method of operating a centrifugal chromatographic system. The method includes 1) rotating a rotor that carries a chromatographic column; 2) establishing a flow of a mobile phase fluid through the chromatographic column in which centrifugal force drives the mobile phase through the chromatographic column; and 3) introducing a sample fluid into the chromatographic column by inserting the sample fluid into the mobile phase fluid flow where the introduction of the sample occurs while the rotor rotates. The method can also include determining whether a steady mobile phase fluid flow condition has been reached within the chromatographic column where the sample fluid is released after it is determined that a steady mobile phase fluid flow condition has been reached within the chromatographic column. After it is determined that a steady mobile phase fluid flow condition has been reached, the method can further include introducing a sample fluid into the chromatographic column to facilitate centrifugal chromatographic separation of the sample fluid.

An additional aspect can be generally characterized as a method of operating a centrifugal chromatographic system. The method includes 1) rotating a rotor that carries a chromatographic column that contains a chromatographic stationary phase; 2) delivering a mobile phase fluid to the chromatographic column while the rotor rotates so that centrifugal force drives the mobile phase fluid through the chromatographic stationary phase; and 3) determining when to introduce a sample fluid into the chromatographic column to facilitate centrifugal chromatographic separation of the sample fluid.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which:

FIG. 5A is a side cross sectional view of a rotor assembly with an illustrated flow path.

FIG. 6 is a side view of the rotor assembly with a cross-sectional view of a reservoir.

FIG. 9A is a top view of an embodiment of a rotor assembly configured for use in a chromatographic system.

FIG. 9B is a side view of an embodiment of a rotor assembly configured for use in a chromatographic system.

FIG. 11 is a front view of a column configured for a chromatographic process before and after centrifugation.

DETAILED DESCRIPTION OF SELECTED EMBODIMENTS

Figure 1:
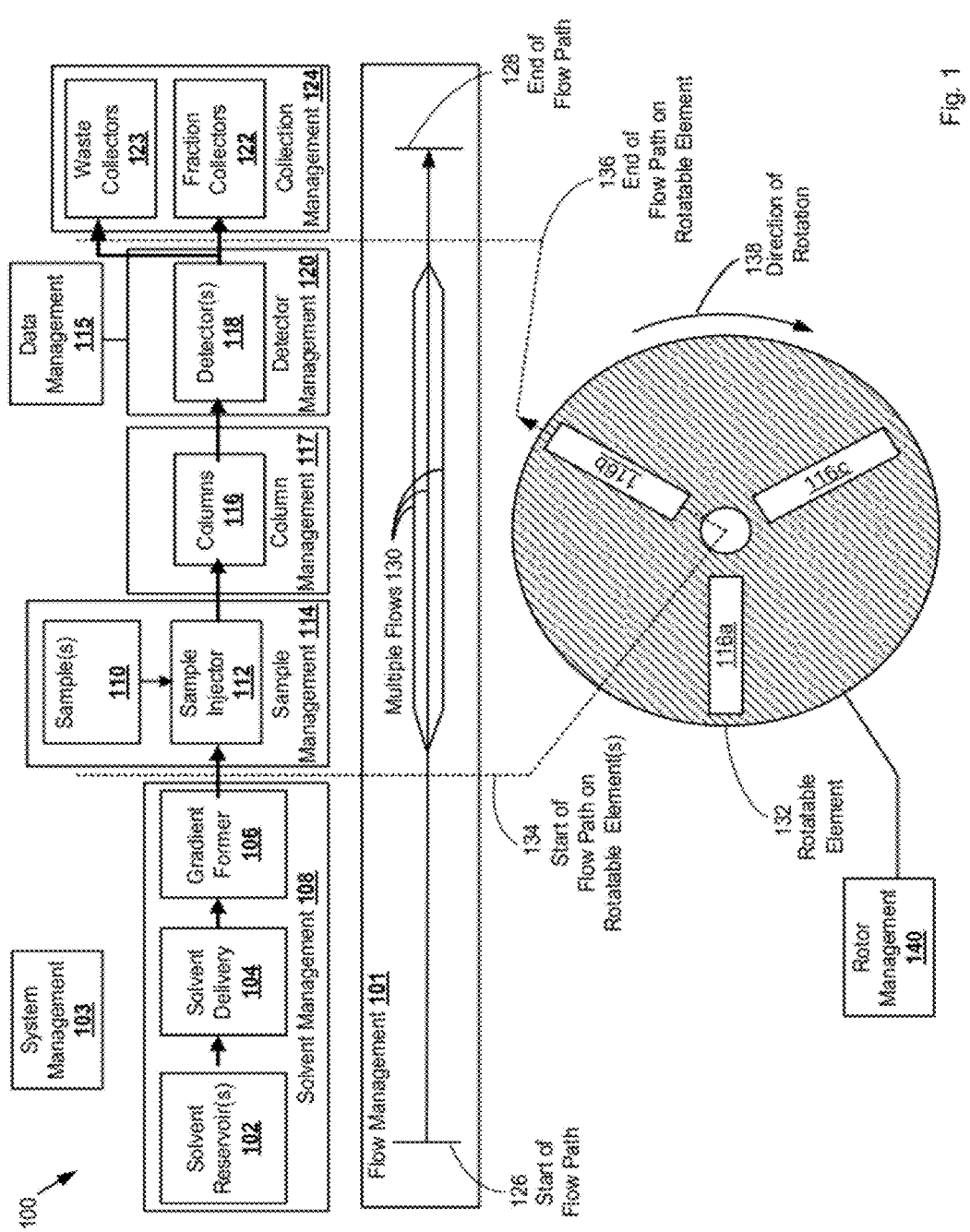
FIG. 1 is a block diagram of a chromatographic system including a rotatable element.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as may be included within the spirit and scope of the described embodiments as defined by the appended claims.

Chromatography can be described as a process that achieves physical separation of the individual components of a mixture of chemical substances. In the chromatographic process, the mixture of chemical substances can be dissolved in (or mixed with) a carrier stream (gas or liquid). The carrier stream including the mixture can be forced through a bed of particles. The carrier stream moves at a velocity through the bed of particles. In chromatography, the carrier stream is often referred to as the "mobile phase" and the bed of particles is referred to as the "stationary phase."

The particles of the stationary phase can be selected such that the components of the mixture dissolved in the mobile phase interact differently with the particles of the stationary phase. Differences in the way components of the mixture interact with the particles can affect how fast each component of the mixture moves through the stationary phase. Thus, the components of the mixture can appear to be moving through stationary phase at different velocities. When two components of the mixture are moving through the stationary phase at different velocities, after traveling through the stationary phase for some distance, the components can be become separated as the component with the faster velocity through the stationary phase travels farther in a given amount of time than the component with the lower velocity travels through the stationary phase.

In liquid chromatography, an objective is to provide a system including a selected mobile phase and a selected stationary phase that allows the components of a mixture to move through the stationary phase at different velocities. When the components of the mixture are separated, at least to some degree, various types of measurement devices can be used to characterize the properties of the separated components and in some instances determine a composition of the mixture. Further, if desired, components separated from the mixture can be collected for further processing and/or analysis.

In liquid chromatography, as described above, the mobile phase can be forced through the stationary phase, which can comprise particles, such as spherical particles of a given radius. The particles can have pores and other molecules can be bound to the particles. The particles radius, pore size and molecules that bound to the particles can be selected to have different types of physical interactions with components dissolved in the mobile phase.

The earliest implementations of liquid chromatography used gravity as a driving force to move the mobile phase through the stationary phase. For instance, a mobile phase can be added to the top of an open column packed with particles of relatively uniform particle size distribution that form a stationary phase. As the mobile phase moves through the stationary phase under the force of gravity, the components of the mixture dissolved in the mobile phase can be separated. In some instances, the separation of components can be observed visually as separated components can have different colors. When the column is a transparent material, such as glass, for certain mixtures, bands of different colors can be observed moving down the column. A column packed with particles and used to separate components in a mixture in this manner can be referred to as a "chromatographic column."

As liquid chromatography developed as a field, it was determined that the ability to separate components in a mixture using a chromatographic column can be increased by decreasing the size of the packed particles of the stationary phase. Using smaller particles increases the packing efficiency of the stationary phase and increases the surface area in a given volume on which interactions can occur between the components of the mixture and the particles of the stationary phase. Thus, methods for manufacturing spherical particles with smaller dimensions for use in a stationary phase of a chromatographic column were developed.

In a gravity-driven chromatographic column, the size of the particles in the stationary phase can not be reduced indefinitely There exists a particle size limit for which the force of gravity becomes insufficient to drive mobile phase and the mixture of components being analyzed through the stationary phase in a practical time frame. To overcome the limits of using gravity as a driving force, other forces, such as pressure, can be used to move the mobile phase through the chromatographic column.

High performance liquid chromatography (HPLC) was developed to enable the use of particles of smaller dimensions to be used in the stationary phase which increases the separation efficiency of the chromatographic column. In HPLC, high pressures are used as a driving force to move the mobile phase through the chromatographic column. In HPLC, the pressure needed to move the mobile phase through the stationary phase of a chromatographic column is inversely proportional to the particle diameter squared. To use a particle size of a few microns, the HPLC system has to be configured to operate at pressures of about 10,000 PSI, which entails the use of high performance and, hence, expensive components. Currently, pressure requirements appear to be a limiting factor to further advances in HPLC, i.e., the use of smaller particles in the stationary phase to increase separation efficiency.

To overcome the deficiencies related to pressure requirements of an HPLC system, it can be asked whether other forces can be used to drive a mobile phase through a stationary phase in a chromatographic column. As described above, gravity was used in early chromatographic systems as a driving force. The effects of gravity on an object can be simulated and even enhanced by placing the object on a platform, such as a disc, that is revolving around an axis of rotation. From the perspective of the object being moved in the rotational reference frame, the object experiences a force along a line that is perpendicular to the axis of rotation that acts in a manner similar to gravity.

The force experienced by an object in a rotating reference frame can be referred to as "centrifugal force." Centrifugal force is often characterized as some multiplier times the force of gravity. For instance, relative centrifugal force (RCF) is the measurement of the acceleration applied to an object being rotated around an axis and is characterized in units of "gravity" or g's. RCF can be calculated as, $$RCF = r(2\pi N)^2/g$$

where r is rotational radius, i.e., the distance of the object from the rotational axis, N is the rotational speed, measured in revolutions per unit of time and g is earth's gravitational acceleration. RCF can also be written as, $$RCF = 1.118 \times 10^{-5} r_{cm} N^2_{RPM}$$

where r is rotational radius measured in (cm) and $N^2_{RPM}$ is the rotational speed measured in revolutions per minute (RPM).

As is described herein, RCF can be used as a driving force for moving a mobile phase through a stationary phase packed in a chromatographic column. To use RCF, a mobile phase can be passed through a stationary phase in a chromatographic column while the chromatographic column is rotating. For example, chromatographic column can be placed on a rotatable disc and chromatographic processes can be performed while the column rotates. Devices and methods for using RCF in a chromatographic system are described with respect to the following figures.

First, a chromatographic system with one or more rotatable elements is described with respect to FIG. 1. Then, details of a various embodiments of a chromatographic system are described with respect to FIGS. 2-13. In particular, embodiments of a rotor assembly for a chromatographic system are described with respect to FIGS. 2-9C. The embodiments of the rotor assembly can support and provide flow paths for a large number of chromatographic enclosures during rotation. A "swinging bucket" configuration is described with respect to FIGS. 10A-10D. In the "swinging bucket" configuration the chromatographic enclosure is more easily detachable from the rotor assembly as compared to the embodiments described with respect to FIGS. 2-9C. An embodiment of a chromatographic enclosure before and after centrifugation is described with respect to FIG. 11. A chromatogram is described with respect of FIG. 12. Finally, a method for performing a chromatographic separation process is described with respect to FIG. 13.

Chromatographic System

FIG. 1 is a block diagram of a chromatographic system 100 including a rotatable element 132. In various embodiments, the rotatable element can also be referred to as a "rotor." The rotatable element 132 can be used to apply RCF to components of the chromatographic system. Prior to discussing the use and associated effects of RCF in a chromatographic system, such as 100, some elements of the chromatographic system 100 are described. The description and number of elements in the chromatographic system are not meant to be limiting for the embodiments described herein and are provided for the purposes of illustration only. Embodiments of chromatographic systems with rotatable elements can have other components as well as a different arrangement of components than those shown in FIG. 1.

The chromatographic system 100 can include solvent management 108. The solvent management 108 allows for different solvents to be used during various chromatographic processes and can vary from run to run of the chromatographic system. The solvent management 108 can include solvent reservoirs, such as 102. The solvent reservoirs can be used to provide a basis for a mobile phase in which a sample can be dissolved for chromatographic processing. A single solvent or a combination of solvents can be used depending on what type of sample is being analyzed. Further, the solvents that are used can be varied from run to run. Thus, a first solvent can be used for chromatographic analysis of a first sample in a first run and a second solvent can be used for chromatographic analysis of a second sample in a second run. Flow control mechanisms, such as valves, can be used to allow different solvents to be accessed at different times according to the requirements of a particular run.

A solvent delivery system, such as 104, can be used to move solvent from the solvent reservoirs for the purposes of forming a mobile phase. Typically, a pump or pumps of some type can be used to provide a driving force for moving solvents from the reservoirs 102. The gradient former 106 can be used to generate a mobile phase comprising a single solvent or a combination of solvents. Binary solvent mixtures are commonly used but more complex solvent mixtures can be employed in the embodiments described herein. During a chromatographic run, when a mobile phase is formed from a combination of solvents, the concentrations of each solvent can be varied as a function of time. The gradient former 106 can be used to control the variation in the concentrations of the constituents of the mobile phase as a function of time.

The chromatographic system 100 can include sample management 114. The sample management 114 allows for different to samples to be introduced to a mobile phase prior to introduction of the mobile phase into a chromatographic column. The sample management 114 can provide storage for various samples, such as 110, and mechanisms for loading the samples into a sample injector 112. The sample injector is an example of a sample introduction mechanism. The sample injector, such as 112, can be used to introduce a selected sample into a mobile phase. For instance, the sample injector can inject the sample into the flow of a mobile phase moving in conduit.

The chromatographic system 100 can include column management 117. The column management can be used to control conditions, such as a temperature, associated with chromatographic columns, such as 116. The temperature of a chromatographic column can be controlled using a device which either heats or cools the column such as a thermoelectric device (Peltier effect device) or any other method of adding or removing thermal energy from the column. Temperature gradients across a column can result in different viscosities across the column and hence a velocity profile that varies across the column. Typically, the temperature is highest near the center of the column and drops off towards the walls of the column as a result of heat conduction through the walls. The walls of the column can be heated to reduce the change in temperature from the center of the column to the walls such that the temperature uniform throughout the column. Also, temperature is well-known to dramatically affect chemical equilibria such as the equilibrium between the analyte, the mobile phase and the stationary phase. To obtain the most reproducible chromatographic results it can be important to have a stable temperature within the column.

The column management 117 can also include software for keeping track of properties of each column, such as but not limited to 1) when it was packed, 2) a composition of the packing, i.e., stationary phase, 3) how many times the column has been used and 4) characteristics of the types of chromatographic runs in which it has been used, such as a composition of the mobile phase solvents used from run to run.

The chromatographic system 100 can include detector management 120. The detector management 120 can involve controlling various instruments used to characterize components separated from the mobile phase during chromatographic processing in the chromatographic column. For example, one or more spectrophotometric detectors can be used to detect changes in the light intensity emitted from a light source (in the ultraviolet and visible ranges, 190 nm to 700 nm), as the light passes through windows of a flow cell through which the column effluent is passing. The physically separated components of the mixture, still dissolved in the mobile phase can pass through the flow cell where light emitted from a first light source is passed through a first window of the flow cell such that it can interact with the components. Light can exit the flow cell through a second window of the flow cell near the second window which can be gathered. The gathered light can be used to determine whether an interaction between the light and one of the separated components has occurred.

The detector management 120 can output information to data management 115. The data management 115 can be configured to collect, analyze and store data derived from one or more detectors. The data management 115 can also be configured to output data derived from a detector. For instance, the data management 115 can be configured to output a chromatogram to a visual display associated with the chromatographic system. The data management 115 can be configured to track and store information gathered from different chromatographic columns where the data can be associated with various parameters of a particular chromatographic run.

The chromatographic system 100 can include collection management 124. The collection management can include fraction collectors 122 that collect separated components that have passed through the columns 116. Different components of interest can exit the column at different times and the collection management 124 can be configured to route each of two or more components to separate fraction collectors. Some components (components can be referred to as elutes) that exit the mobile phase may not be of interest and can be considered as "waste." For instance, prior to introducing of sample, a solvent can be passed through the column. The collection management 124 can collect the solvent that elutes from the column prior to the introduction of the sample as waste in collection device, such as waste collectors 123.

In the embodiments described herein, the chromatographic system can comprise one or more rotatable elements, such as rotatable element 132. The rotatable elements can be controlled by the rotor management 140. The rotor management 140 can implement a rotation rate versus time profile for the rotatable element 132 including a spin up, a steady spin rate and a spin down. The rotor management 140 can monitor the rotatable element 132 to ensure it is operating properly and perform procedures associated with operating the rotatable element 132, such as auto-balancing. The rotor management 140 can also monitor and control power delivery for various components operating on the rotatable element 132, such as electronically controlled valves located on the rotatable element.

The system management 103 can be configured to monitor and control the over-all functioning of the chromatographic system 100 during different operational modes of the system 100, such as initialization mode, an operational mode and a shutdown mode. The system management 103 can be configured to communicate with and send commands to the flow management 101, the solvent management 108, the sample management 114, the data management 115, the column management 117, the detector management 120, the collection management 124 and the rotor management 140. The system management 103 can also be configured to communicate with other devices and systems, such as other chromatographic systems and remote computers.

The chromatographic system 100 can involve a management of one or more flows. The flow management 101 can be configured to coordinate flow throughout the system 100. The flow management 101 can be configured to control various valves and pumps located throughout the system 100 directly or through communications with other device components. For instance, the flow management 101 can be configured to send a command to the solvent management 108 to deliver a particular solvent flow rate and one or more logic devices associated with the solvent management 108 can control devices, such as valves and pumps to the deliver commanded flow rate or the flow management 101 can be configured to directly control the valves and pumps associated with the solvent management 108.

Flow Path Management and Flow Analysis

The flow management system 101 can involve the establishment and maintaining of multiple flow paths where the number of flow paths can vary from system to system or can be varied within one system. A flow in the chromatographic system 100 can involve a start of the flow path 126, which as an example can start in the solvent reservoirs 102. Fluid can be moved from the reservoirs to the gradient former 106 via the solvent delivery system 104. At a point 134 in the flow path, the flow can be transferred to the rotatable element 132. The transfer of flow can occur while the rotatable element 132 is rotating with a rotational velocity and a direction of rotation 138. In different embodiments, the rotational velocity and direction of rotation can vary. In other embodiments, the transfer of flow can occur while the rotatable element is stationary.

On the rotatable element, 132, the flow at different locations can be moving away from the center of the rotatable element 132 and at other locations, the flow can be moving toward the center of the rotatable element 132. Along a flow path on the rotor, the flow can also be moved between different levels of the rotatable elements. For instance, the flow can move through chromatographic columns at a first level and then can be moved to another level, such as to a reservoir located at a level below the chromatographic columns.

In a particular embodiment, the flow can enter near a center of the rotatable element and then start to flow away from the center and enter chromatographic columns, such as 116a, 116b and 116c. For example, the flow can start with a common source near the center, such as a mixing chamber located near the center, and then can be split into multiple flow paths. For instance, the flow can be split during the sample management 114 to allow for different samples to be introduced into different flow paths. This example of a split location is provided for the purposes of illustration only. In particular embodiments, a split location where a flow is branched into multiple flows can be implemented at any point in the flow path, such within the solvent management 108, i.e., at the reservoirs 102, before or within solvent delivery 104, before or within the gradient former 106, before within sample management 114, before or within the columns 116, before or within the detector management 120 or before or within the collection management 124. Further, the flow management 101 can be configured to implement split locations that can vary from run to run of the chromatographic system.

As an example of flow splitting, the flow can start with a single flow path prior to the sample management 114. At the sample management 114, the flow can be split into multiple flow paths 130, such as 3 flow paths, where if desired a different sample can be injected into each flow path and allowed to pass through one of the chromatographic columns, 116a, 116b and 116c.

As another example, the flow can be split after the sample management 114. A single flow can enter the sample management 114 and a common sample can be injected into the single flow. Then, after the sample management 114, the flow can be split into multiple paths to allow for parallel processing of the split flow by multiple chromatographic columns. For instance, a single flow with a common sample can be generated in the sample management and then split into three flow paths for processing by the chromatographic columns 116a, 116b and 116c.

In some embodiments, the flow management 101 of the chromatographic system 100 can be configured to allow the number of flow paths and the locations where flow paths splits occur to be switched and controlled. The flow management 101 can include flow conduits that allow a number of flow paths to be simultaneously established. Further, the flow management can include switching mechanisms, such as valves, that can be opened in closed at different locations that allow the number of flow paths established at a particular location to be changed.

As an example, the flow management 101 can control flow conduits located within the sample management 114 that allow up to 3 flow paths to be established. The flow management can control branching mechanisms that are located before and after the sample management. In a first mode, the branching mechanism can be turned on prior to the flow reaching the sample management 114 to establish 3 separate flow paths (each flow path can be associated with a chromatographic column, such as 116a, 116b and 116c). Within each of the 3 flow paths, the sample management 114 can inject a different sample which can then proceed into the chromatographic columns for analysis.

In a second mode, the flow management can be configured to switch off a branching mechanism prior to the sample management 114, such that only a single flow path enters the sample management 114 and only a single sample can be introduced. After the sample is injected into the single flow path, a branching mechanism can be actuated that allows single flow path to be split into multiple paths and pass through multiple columns. For instance, the single flow path can be split into three paths for processing by columns, 116a, 116b and 116c. The chromatographic system can be configured to operate in the first mode or the second mode.

The flow management 101 can be configured to control flow switching mechanisms that allow different combinations of flow paths to be combined or to be split at various locations throughout the chromatographic system 100, such as within the solvent management, within the sample management 114, within the column management 117, within the detector management 120 or within the collection management 124. For example, when possible three flow paths are available the flow management 101 can be configured to control flow switching mechanisms such that a single flow path, three separate flow paths or two separate flow paths can be generated at different times and at different locations within the chromatographic system 100. Further, at different flow locations, the flow can be split from a single flow to two flows, from a single flow to three flows or from two flows to a single flow.

After the flow passes through each of the columns, it can be analyzed using one or more different detectors 118. For instance, a flow cell can be located near the end of the column that includes a transparent window that allows a light source to be shown through the flow cell. During the passage of the column effluent (solvent mixture plus the physically separated components of the original sample mixture) through the flow cell, light exiting the flow cell can be captured using a detector 118, such as a photomultiplier tube. As another example, after passing through a chromatographic column a portion of the flow can be diverted to an instrument, such as a mass spectrometer, for additional analysis.

In some embodiments, a single detector can be used for analysis of multiple flow paths. For instance, a single light source and single photomultiplier tube can be used to analyze flow flowing through multiple flow cells, such as three flow cells associated with each of the chromatographic columns, 116a, 116b and 116c. An advantage of instrument sharing for multiple flow paths is reduced costs. Further details of instrument sharing are described with respect to FIGS. 10A-10D.

At another point in the flow path, such as 136, the flow can exit the rotatable element 132. The exit 136 from the rotatable element can occur while the rotatable element 132 is rotating or while the rotatable element is stationary. As shown in the figure, after the flow leaves rotatable element 132, it can enter a waste or fraction collector. In 128, the flow (elutes) entering the waste and/or fraction connectors can mark the end of the path.

Besides flow splitting, flow coalescing can also occur. In FIG. 1, an example of flow coalescing is indicated where the multiple flows converge into a single flow. For example, when there is no sample collection, all of the output from the chromatographic columns can be coalesced into a single flow that is diverted into a common waste collector. Like the flow splitting, the chromatographic system 100 can include flow switching mechanisms that allow different flow paths to be coalesced at different locations where the locations where the flow is coalesced can be varied from run to run. The flow management 101 can be configured to perform the flow control associated with the flow coalescing, such as controlling the locations where flow coalescing occurs.

Column Condition Management

One aspect of the chromatographic system 100 is an ability to establish a set of repeatable conditions within a chromatographic column. Thus, for a given flow path, system 100 can be configured to establish and maintain a particular set of conditions associated with a chromatographic column. The conditions can include but are not limited to establishing and maintaining 1) a flow velocity within the column, 2) a solvent composition that varies with time during the chromatographic process, 3) a column temperature, 4) a solvent temperature and 5) a rotational condition of the column, such as a constant angular velocity.

In particular embodiments, prior to introducing a sample into the chromatographic column, the chromatographic system 100 can be configured to establish an initial steady-state condition, such as a steady flow velocity, within the chromatographic column. Establishing an initial steady-state condition can refer to determining that each of a selected set of column parameters are varying within some acceptable range over a particular time period. One reason for establishing steady-state conditions prior to introduction of chromatographic sample is process repeatability. Chromatographic experiments can be repeated for a number of reasons and it can be desirable that the conditions of the experiment be carried out each time in the same manner.

For example, chromatographic experiments can be repeated from the purposes of fraction collection. For a given set of conditions within a chromatographic column, a sample constituent can remain in the column for a certain period of time depending on its interactions within the chromatographic column. The amount of time that a sample constituent remains in the column can vary from constituent to constituent and is a function of the column conditions (Chromatographic column conditions can be intentionally selected to encourage a time differentiation between an amount of time one constituent remains in the column relative to another constituent where the time differentiation is a reflection of the chromatographic separation efficiency of the column). Sample constituents exiting the column at a certain time can be collected. The portion of the flow exiting the column at a certain time that is collected can be referred to as a fraction. One advantage of establishing steady-state conditions in the chromatographic column prior to sample introduction is that a repeatable processes can be set-up where fractions are collected at a certain time after the sample is introduced.

As another example, the chromatographic process can be used to determine a presence and an amount of a particular constituent in a sample. The chromatographic process can be repeated a number of times to establish statistical error bounds for a measurement, such as an amount of a constituent in a sample. As a rule of thumb, a sampling error is proportional to $1/N^{1/2}$ (e.g., 100 samples are required to establish a 10% error bar). Thus, the chromatographic process can be repeated many times on a particular sample to establish some reasonable error bounds for a measurement, such as an amount of a particular sample constituent. One advantage of establishing steady-state conditions in the chromatographic column prior to sample introduction is to minimize errors associated with transient effects that can occur from run to run.

Referring to FIG. 1, a number of different components can be involved in establishing steady-state flow conditions within column associated with a particular flow path. In one embodiment, this function can be controlled by the flow management 101. To establish steady-state conditions, the flow management 101 can receive data and send instructions to various components in the chromatographic system 100.

As an example, to establish a steady flow condition, the system 100 can initialized for a run and then a rotatable element, such as 132, can be spun up via some angular velocity profile to a constant angular velocity. During spin-up or after the constant velocity is reached, the flow management 101 can initiate flow on the rotatable element 132. To initiate the flow, the flow management can instruct a solvent delivery system, which can be located on or off the rotatable element 132 to begin introducing a solvent into a flow path. The solvent can then begin flowing through the system 100, such as through a chromatographic column, such as 116a, 116b or 116c.

In one embodiment, to determine whether a steady-state mobile phase velocity has been reached, the flow management 101 can send instructions to the solvent management 108 to provide a solvent composition with a first component that is varying in a known way, such as the first component increasing or decreasing as a fraction of the composition as a function of time. The component that is being varied can be selected such that it does not interact with the stationary phase of the chromatographic column and is detectable by one of the instruments in the detector management 120. Using the information regarding how the first component is being varied and the information received from the detector management 120, the flow management can determine a mobile phase velocity and its variation over time.

In another embodiment, a mass flow meter can be located in the flow path, such as in the flow path after a flow cell. The mass flow meter can be used to determine a flow velocity. Based upon information received from the mass flow meter, a system component, such as the flow management 101, can determine whether a steady-state mobile phase velocity has been achieved. When it is determined that the mobile phase velocity as well as other column conditions are within acceptable values and their variation over time is within an acceptable limit, the column can be identified as being ready for sample introduction.

As previously described, the rotatable element 132 can include a number of columns, such as the three columns 116a, 116b and 116c. The determination regarding steady state flow and/or column conditions being reached prior to sample introduction can be made on a column-by-column basis. The flow and/or column conditions determined for each column at least prior to sample introduction can include but are not limited to a mobile phase flow velocity, a solvent composition, a flow pressures (e.g., before and after the column), a flow temperatures (e.g., before, after the column), column temperatures (e.g., on the outside of the column) and combinations thereof. As previously described, data associated with each column including whether steady state has been reached for the column can be stored by one or more of the system components, such as the column management 117.

Measurements of flow and column conditions can also be made as a function of time after a sample is introduced. For instance, a flow velocity can be measured while a sample is progressing down a chromatographic column. As another example, column temperatures on an outside of the column at one or more locations along the column can be recorded as a sample is moving down a chromatographic column.

In some embodiments, the chromatographic system 100 can be configured to determine whether flow and/or column conditions measured during a chromatographic process are within acceptable ranges. A chromatographic process can take a particular amount of time and the column conditions can be monitored during the time associated with the chromatographic process. An unacceptable condition can occur prior to a sample being introduced, such as a steady state condition not being reached, or after sample introduction. For instance, for one or more of the columns, a particular value at one time or a time variation of a parameter, such as a mobile phase flow velocity or a temperature can be out of an acceptable range. One or more column parameters being determined to be out of an acceptable range can result from a number of factors, such as a faulty flow cell associated with one of the columns (e.g., one of the windows can be dirty), a faulty temperature sensor associated with one of the columns, a faulty pressure sensor associated with one of the columns or a leak in one of the flow paths (a pressure sensor can be used to determined whether a leak has occurred).

Based upon determined flow and column conditions during a particular a run, the system 100 can be configured to identify acceptable and unacceptable columns. Certain columns can be identified as unacceptable prior to a sample being introduced. For instance, a column can be identified as unacceptable when it is determined that steady state conditions have not been met in a particular column. Other columns can be identified as unacceptable after a sample is introduced. For example, an out of range pressure measurement can be detected for a particular column while a sample is proceeding down a column and the column associated with the out of range pressure measurement can be identified as unacceptable.

In some embodiments, the system 100 can be configured to operate with some of the columns identified as unacceptable where data collected from unacceptable columns can be ignored and data gathered from columns determined to be acceptable can be used. For example, a first chromatographic column, such as 116a, can be identified as unacceptable for one of the following: 1) when initial steady-state conditions are not established within an acceptable range, 2) a steady-state condition is reached but a parameter is out of range or 3) a flow or a column condition is determined to be out of an acceptable range while a sample is proceeding down the chromatographic column. A second chromatographic column, such as 116b, can be identified as acceptable when it is determined that steady-state conditions are reached and all values are within an acceptable range prior to and after sample introduction, i.e., during the chromatographic process associated with a particular run. Like the determination of whether steady-state conditions have been established, the identification of columns as being acceptable or unacceptable for the purposes of using data gathered from the column can be made on a column by column basis.

System Functions On or Off of a Rotatable Element

In various embodiments, functions of the chromatographic system 100 can be performed by components located on a rotatable element, such as 132, or performed by components located off of a rotatable element. Whether a particular function is performed on or off of rotatable element can vary from system to system and can also vary from run to run within a single chromatographic system. This delineation of the system elements between rotatable elements and non-rotatable elements is provided for illustrative purposes only and is not limited to the example described with respect to FIG. 1.

In FIG. 1, a portion of the flow path and associated systems are shown on the rotatable element 132 and a portion of the flow path and associated systems are shown located off of the rotatable element. For example, solvent management 108 and collection management 124 are shown off the rotatable element 132 and the sample management 114, column management 117 and detector management 120 are shown located on the rotatable element 132. In other embodiments, an entire chromatographic system 100 including solvent management 108, sample management 114, column management 117, detector management 120 and collection management 124 can be located on rotatable elements, such as 132. Further, some parts of the chromatographic system 100 can be duplicated on rotatable and non-rotatable elements. For instance, a chromatographic system 100 can include solvent management components, such as first solvent reservoirs located on the rotatable element and a second solvent reservoir located on a non-rotatable element. In some instances, the first solvent reservoir on the rotatable element 132 can be used. In other instances, the second solvent reservoir on the off the rotatable element 132 can be used. In yet other embodiments, the first solvent reservoir on the rotatable element 132 and the second solvent reservoir off the rotatable element can both be used.

In another example, the detector management 120 can include first instrumentation located on the rotatable element 132, such as a mass spectrometer, and second instrumentation, such as a light source and a photomultiplier tube located off of the rotatable element 132. Further, even when the light source and the photomultiplier tube are located off the rotatable element, a flow cell that is needed to use this instrumentation can be located on the rotatable element 132. In some embodiments, only the first instrumentation located on the rotatable element 132 can be used. In other embodiments, only the second instrumentation located off of the rotatable element can be used. In yet other embodiments, a combination of instruments located on and off of the rotatable element, such as the first instrumentation and the second instrumentation can be used.

Stationary-Rotational Interfaces

As described above, a chromatographic system can include one or more rotatable elements, such as 132. At various times, during the operation of the chromatographic system, one or more rotatable elements, such as 132, can be at rest or can be rotating. When a rotatable element is rotating, it can be desirable to provide an interface that allows some quantity to be moved between a stationary element and the rotatable element. Some examples of these quantities include fluids (e.g., gasses or liquids), power and data. A single rotational element can be coupled to stationary elements via multiple stationary-rotational interfaces. For instance, a rotatable element can coupled to a number of different stationary elements via multiple fluid interfaces, power interfaces and data interfaces.

In particular embodiments, an interface can be designed to move a quantity in only one direction, such as from a stationary element to a rotating element or from a rotating element to a stationary element. For instance, a first fluid interface can be configured to only deliver fluid from a stationary element to a rotating element while a second fluid interface can be used to only deliver fluid from a rotatable element to a stationary element. In other embodiments, an interface can be configured as bi-directional and allow a quantity to be both moved from a stationary element to rotatable element and from the rotatable element to the stationary element simultaneously or at different times.

For instance, a single fluid interface can be configured to deliver fluid from a stationary element to a rotatable element and to receive fluid from a rotatable element and deliver it to a stationary element at the same time. In this example the flow can be moving between the stationary and rotatable elements via separate flow conduits. In another example, at first time a single fluid conduit can be used to deliver fluid from the stationary element to a rotatable element and at a second time, it can be used to receive fluid from the rotatable element and deliver it to a stationary element.

Operational Modes

The chromatographic systems described herein, such as system 100 in FIG. 1, can be configured to operate a number of different modes. During the different operational modes, the chromatographic system can perform different functions. A few examples of different operation modes are initialization, operational, spin-up, spin down, chromatographic processing and data collection between runs, and malfunction.

During initialization, the chromatographic system can perform a number self-checks to determine a status of its various system components, such as but not limited to instrumentation statuses, fluid reservoir level statuses, gas pressure statuses, pump statuses, valve statuses, a motor status, balancing checks, device power statuses, and device communication statuses. These self checks can be associated different system elements, such as flow management 101, solvent management 108, sample management 114, data management 115, column management 117, detector management 120, collection management 124 and rotor management 140. After self-checks have been performed, it can be determined whether the chromatographic system can enter into an operational mode or whether corrective actions are needed for one or more of chromatographic system components. The chromatographic system can output whether corrective actions are needed or chromatographic system can indicate that it is in an operational state.

After the chromatographic system enters into an operational state, it can be configured for a particular run. In some embodiments, the chromatographic system, such as via system management 103, can provide an interface that allows a user to specify one or more adjustable parameters of the run. After parameter of a particular run is specified, the chromatographic system can implement the run using the selected parameters. For example the chromatographic system can spin up one or more rotatable elements, such as element 132, from a resting state to some angular velocity target according to some angular velocity profile. Spin-up can include rotor management functions, such as checking and adjusting a balance of the system and flow management functions, such as initial fluid introduction into the system and leak detection.

After spin-up, the system can determine whether it has reached conditions, such as a steady flow condition, such that chromatographic processing can begin. When it is ready for chromatographic processing, functions such as sample introduction and data collection can begin. The system can monitor the chromatographic processing until it determines a run is completed. When a run is completed, the chromatographic system can begin a spin-down procedure.

During spin-down, a rotatable element 132 can be decelerated according to some angular velocity profile from a particular angular velocity to rest. Prior to or during spin down, the flow management 101 can change flow functions, such as shutting down the flow in the rotatable element 132. After spin-down, while the rotor is at rest, functions, such as draining on-rotor flow reservoirs or removing fractions collected on the rotatable element can be performed. Between runs, functions such as flushing fluids from the columns in the rotatable element for the purposes of cleaning can be performed. Flushing the columns can involve a spin-up and spin-down of the rotatable element, such as 132, to allow fluid to be pushed through system.

A malfunction can occur during any of the operation modes. When a malfunction is detected, the system 100 can go into a unique malfunction mode depending on the type of malfunction. For instance, if a leak is detected during spin-up or a sudden change in balance is detected while the rotatable element is rotating, such as a result of a leak or a component failure, a spin-down malfunction mode can be implemented. The spin-down malfunction mode can involve de-accelerating the rotatable element faster than it is normally de-accelerated during normal operations.

Rotatable Elements

In FIGS. 2-8, details of one embodiment of a rotatable element that can be utilized with chromatographic system are described. Additional embodiments of a rotatable element are described with respect to FIGS. 9A-9C. In particular, with respect to FIGS. 2 and 3, a rotor assembly including a number of chromatographic columns is described. With respect to FIGS. 4A and 4B and 6 a number of components of the rotor assembly are discussed. In FIGS. 5A-5C, further details of the rotor assembly are described including a discussion of a flow path through the rotor assembly. In FIGS. 7A-C and 8, a number of components for allowing the rotor assembly to be utilized as part of a chromatographic system are discussed. With respect to FIGS. 9A, 9B and 9C, embodiments of rotor assemblies including sample injection, column conditioning, power generation, off-rotor communications, fraction collection and a reaction chamber are described. With respect to FIGS. 10A-10D, an alternate system for performing centrifugal liquid chromatography that incorporates a swinging bucket design is described.

Figure 2:
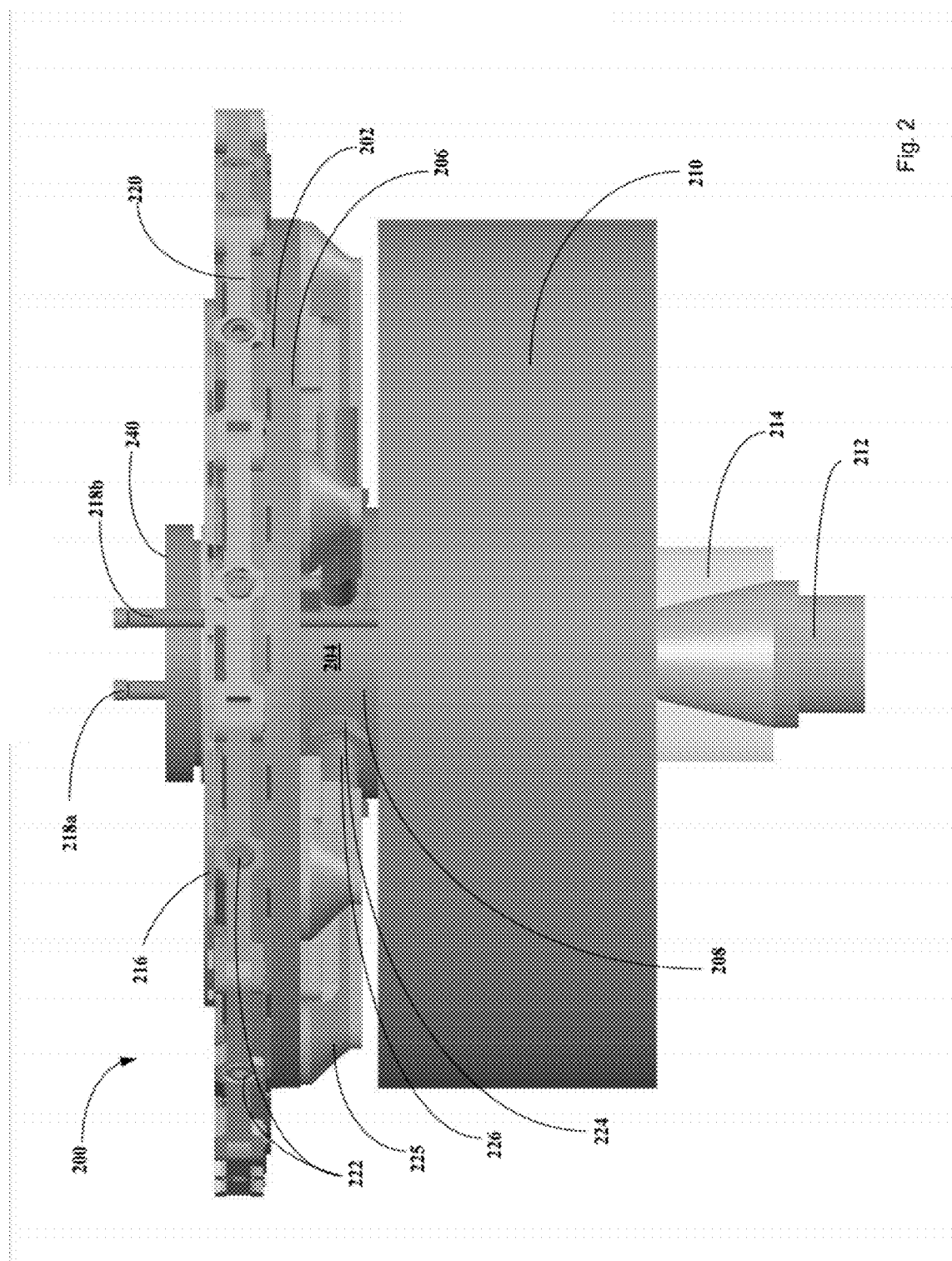
FIG. 2 is a side view of an embodiment of a rotor assembly configured for use in a chromatographic system.
Figure 3:
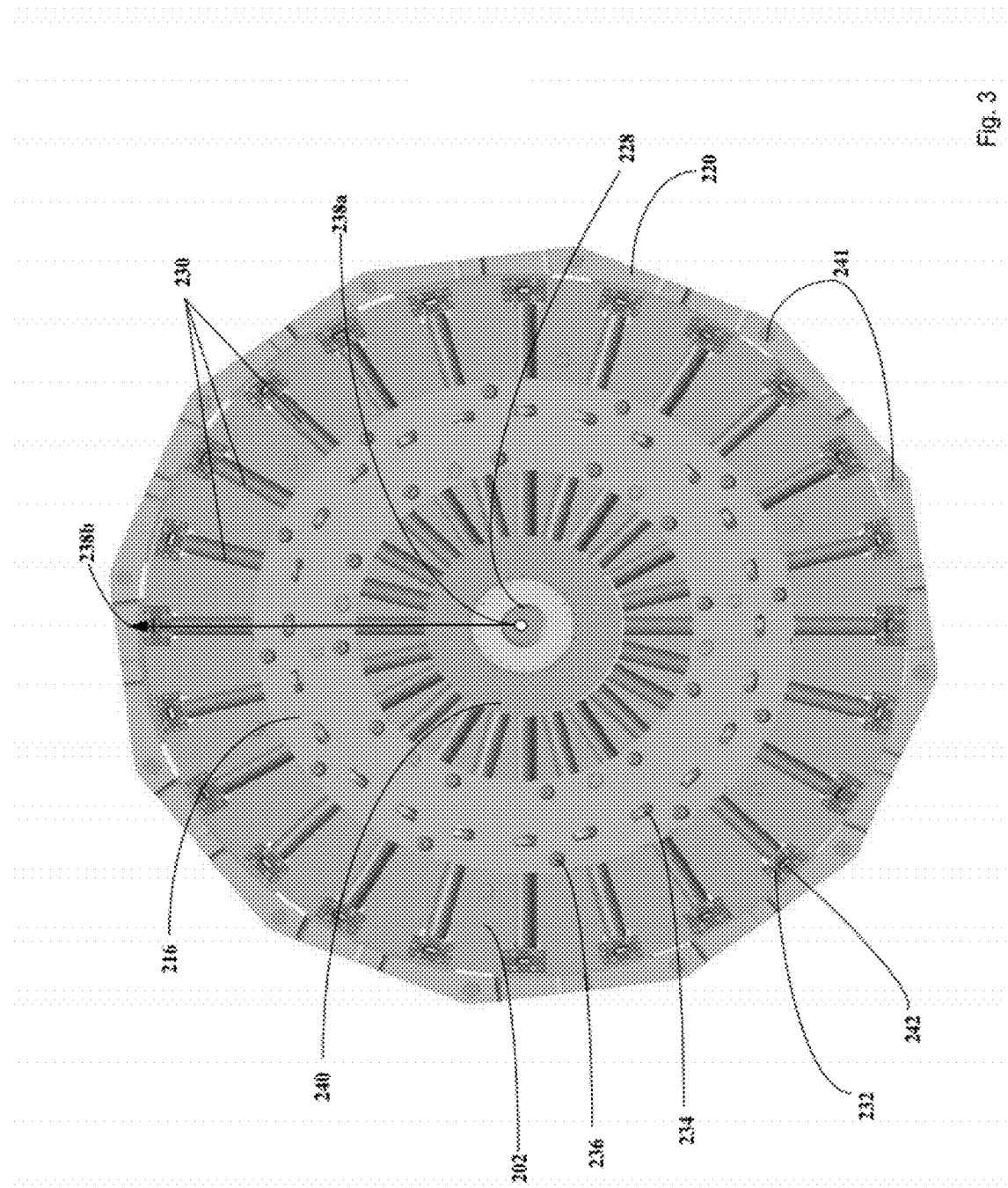
FIG. 3 is a top view of an embodiment of a rotor assembly configured for use in a chromatographic system.

FIGS. 2 and 3 are a side view and top view of an embodiment of a rotor assembly 200 configured for use in a chromatographic system, such as the chromatographic system described with respect to FIG. 1. The rotor assembly is one embodiment of a rotatable element. As is described with respect to FIG. 1, the components on or off of a rotatable element can vary from chromatographic system to chromatographic system. Thus, the embodiments described with respect to FIGS. 2-9C are provided for the purposes of illustration only.

The rotor assembly 200 can include a platter assembly 202, a manifold assembly 204, an adapter plate assembly 214 and a liquid introduction assembly including a mixing chamber 228 located in a center portion of the platter assembly 202. The manifold assembly 204 includes a disk portion 206 and a column portion 208. The liquid introduction assembly can be coupled to the platter 202 via a number of fasteners. The platter 202 can be coupled with fasteners to the disk portion 206 of the manifold assembly. A bottom of the column portion 208 of the manifold assembly can be coupled to the adapter plate assembly 214 via an adapter plate (see FIG. 6 for more details of the adapter plate assembly 214 and the adapter plate).

A reservoir 210 is coupled to the adapter plate assembly 214. The adapter plate assembly includes an interface to a shaft, such as tapered shaft 212. The shaft provides a coupling mechanism to a motor (not shown) that allows an angular velocity to be imparted to the rotor assembly 200. The angular velocity of the rotor assembly can be varied as a function of time based upon operating commands sent to the motor. In one embodiment, the motor can be a Sorvall Model RC5C (Thermo Scientific, Waltham, Ma), which can provide RPM's between 300 to 22,000 and RCF's up to 55,000 g's. Further details of the manifold assembly 204 and the adapter plate assembly 214 including a coupling of these components is illustrated with respect to FIGS. 5A and 6. In general, any suitable mechanism can be used to drive a rotor and impart an angular velocity to the rotor. For instance, systems using a compressed gas, such as compressed air, can be used to drive a rotor.

As is illustrated in FIG. 3, the platter 202 includes a number of columns, such as 230. The columns, which can also be referred to as chromatographic enclosures, include a hollow interior portion in which materials, such as materials used to perform a chromatographic process, can be packed. During operation, the hollow interior portion can provide a flow conduit for a flow path (e.g., see FIG. 5A). When packed with chromatographic materials, a chromatographic separation can occur along a portion of flow path within the columns, such as 230.

In the embodiment shown in FIG. 3, 24 columns are arranged around the platter 202. In some embodiments, as is shown, the columns, such as 230, can include a common length, a common outer diameter and a common inner diameter. The columns can also be generated from a common material, such as a metal or metal alloy. Further, the columns can be distributed around the circumference of the platter 202, such that an equal angular spacing is provided between each of the columns. In yet other embodiments, some flow conduits used in the rotor assembly can be generated from a flexible material, such as a flexible plastic.

In other embodiments, the number of columns on a platter can be varied, such that a platter 202 can include more or less than the 24 columns that are shown. In addition, on a single platter, a length of the column, an outer diameter and an inner diameter of the column can vary from column to column over the number of columns arranged on platter 202. Further, a composition of a chromatographic material, such as a stationary phase material, packed within the column can vary from column to column. Also, the angular spacing between columns does not have to be equal and the spacing between columns can vary from column to column. Further, the material form which the column is generated can vary from column to column (e.g., first column can be composed of a ceramic material and a second column can be composed of a metal alloy.)

In yet other embodiments, a rotor assembly can include a number of platters. The platters can be arranged in a stacked configuration one on top of the other. In one embodiment, a transmission and/or mechanisms can be associated with each platter that can be used to allow the platters to engage and disengage from a rotating shaft and to rotate at different speeds from one another. From platter to platter, the number of columns can be varied. Further, the column parameters, described above, such as the column length, outer diameter, inner diameter, column material, column spacing and column packing material can vary from platter to platter.

In the embodiment in FIG. 3, a flow cell, such as 232 can be located at the end of each column. The flow cell 232 can include windows and a hollow interior portion. The hollow interior portion can provide a flow conduit for flow that exits an associated column, such as a column in which a chromatographic process is performed. The windows can allow a light source to be passed through the flow cell.

In some embodiments, the flow cells located at the end of each column can be a common flow cell with a similar design, such as windows located on a top and a bottom portion of the flow cell and common dimensions for the interior portion. In other embodiments, the flow cell associated with each column can vary from column to column. For instance, a first column on the platter can be associated with a flow cell that has windows located on its sides while a second column can be associated with a flow cell that has windows located on the top and bottom. In addition, if column parameters vary from column to column, such as a column diameter, then the flow cell parameters, such as a size of an interior portion of the flow conduit, can also vary.

In other embodiments, a flow cell does not have to be associated with each column. For instance, a first column can be associated with a flow cell while a second column can be associated with a mass spectrometer and not even be associated with a flow cell. In another example, a flow cell and a mass spectrometer can be associated with a column. Thus, in general, the instrumentation associated with a chromatographic column can vary from column to column on a single platter and can also vary between platters. Further details of instrumentation that can be utilized with a column, such as a column in which a chromatographic process can be performed, are described below in the section titled, "Instrumentation."

Returning to FIGS. 2 and 3, the columns, such as 230, can be held in place via a column clamp ring 216. The column clamp ring 216 can be attached to the platter 202 via a plurality of fasteners, such as 236. In one embodiment, a load associated with each column can be channeled through a load support mechanism, such as a pre-load nut 234. The pre-load nut 234 is visible through the column clamp ring 216. The pre-load nut can be coupled to platter 202.

During rotation, the columns experience a large RCF, which can be hundred's to thousands of g's. When a flow cell is located at the end of a column near an outer edge of the platter 202, as is shown in FIG. 3, the large RCF experienced by the column can be transferred as a force to the flow cell, such as 232. If too large a force is transferred to the flow cell, a shape of the flow cell can be distorted including a shape of the flow cell windows, such as 242. A distortion in the flow cell, such as a distortion in the windows, can cause degradation in the optical properties of the flow cell and hence can degrade a measurement quality associated with using the flow cell. A load support mechanism, such as a pre-load nut, can be used to bear some of the loads generated by the column during rotation and hence, reduce potential loads on the flow cells, such as 232. The pre-load nut associated with each column can be mechanically coupled to the platter 202 such that a portion of a load on the column is transferred to the platter or some other support structure rather than to the flow cell.

The liquid introduction assembly including a mixing chamber 228 can be located in a center 238a of the rotor assembly 200. In one embodiment, fluid can enter the mixing chamber 228 from a fluid source that remains stationary while the rotor assembly 200 is rotating. For instance, one or more flow conduits can be inserted down into the mixing chamber 228 where the conduits can remain stationary while the mixing chamber 228 is rotating. During operation, fluid can exit the conduits and enter the mixing chamber 228 to provide a continuous and controlled supply of fluid to the rotor assembly 200.

An assembly including a gas bearing where the gas bearing provides an interface between the assembly including the conduits and the rotor assembly 200 can support the conduits. The rotor assembly 200 can include a seat 240 for the gas bearing. While the rotor assembly is rotating, the gas bearing can rest on the seat 240. Further details of the gas bearing support assembly that can include the stationary fluid source and support for the conduits are described with respect to FIGS. 7A-7C.

Fluid can enter the mixing chamber 228 and then move along a flow path from the center 238a of the platter 202 to an edge of the platter 238b. In some embodiments, the columns can be arranged proximately along radial lines (i.e., lines that pass through a center of the platter 202) such that a direction of the bulk flow is along one of the radial lines. In other embodiments, one or more of the columns can be arranged along a non-radial line that does not pass through a center of the platter. Nevertheless, a centrifugal force component along the non-line radial line can still move the flow through the non-radially aligned column.

In one embodiment, fluid components from one or more sources can enter the mixing chamber 228 and can be mixed. Mixing can be generated from a rotation of mixing pins in the mixing chamber. The mixed fluid components can exit the mixing chamber 228 through a number of ports, such as a port associated with each column. Thus, in one embodiment, two or more of the columns can receive fluid from a common source. More details of the mixing chamber 228 are described with respect to FIG. 5A.

A fluid mixture can then move through each of the columns and into an associated flow cell near the edge 238b of the platter 202. After passing through the flow cell, such as 232, the fluid can move beyond the edge 238b of the platter 202 and into a return segment link 220. The return segment links, such as 220, can include a flow channel that routes the fluid exiting a flow cell along the edge of the platter 202. The return segment link, such as 220, can be connected to a return flow channel that is next to a column that feeds it fluid. Once the flow enters the return channel, it can be moving generally away from edge 238b and towards center 238a.

In this embodiment, a fluid flow can enter a beginning of a column that is located near a center of the platter 202 and exit an end of column near the platter edge. The column can include a chromatographic packing material such that a chromatographic separation of components in a fluid mixture can occur as the flow moves from the beginning of the column to the end of the column. The centrifugal forces on the fluid in the column can increase as fluid in the column moves down the column toward the edge of the platter 202. For this orientation, the increasing centrifugal forces can result in a fluid pressure increasing along a length of the column as the chromatographic process occurs. This pressure profile along the column differs from chromatographic systems, such as a high performance liquid chromatography (HPLC). In HPLC, pressure is used to move fluid from a beginning of the chromatographic column to an end of the chromatographic column. Thus, the pressure drops from the beginning of the column to the end of the column as opposed to increasing.

In particular embodiments, a maximum operational pressure of the rotor assembly can be about 100 PSI. For instance, the peak pressure as the pressure increases from a center of the rotor to the edge of the rotor can be less than 100 PSI. In other embodiments, the maximum operational pressure can be less than 50 PSI. The maximum pressure levels, such as below 100 PSI, are much less than HPLC maximum pressure levels, which can be 1000's of PSI for smaller particles sizes.

In a particular embodiment, the return segment links, such as 220, can be linked together via connectors, such as 241. The inner surface of each return segment link can conform to an outer surface of the platter 202. For instance, when the outer surface of the platter 202 is curved, then the links can conform to the curvature of the outer surface of the platter 202. The links can each be coupled to the platter via fasteners, such as 222. Further details, of the return segment links are discussed with respect to FIGS. 5A-5C.

After moving through the return segment link and into a return flow channel in platter 202, the flow can move into a circumferentially aligned channel in the disk portion 206 of manifold assembly 204. The circumferentially aligned channel can drain into the manifold blocks, such as 225. Each manifold block can be coupled to an adjustable tube 226, which is coupled to the column portion 208 of manifold assembly via lock nut 224. The flow can then move through the column portion of the manifold assembly and eventually into reservoir 210. Fluid can be periodically drained from the reservoir 210 via the reservoir drainage tubes, 218a and 218b. More details of the flow path including the flow path through the interior of the rotor assembly 200 are described with respect to FIGS. 5A-5B

Figure 4A:
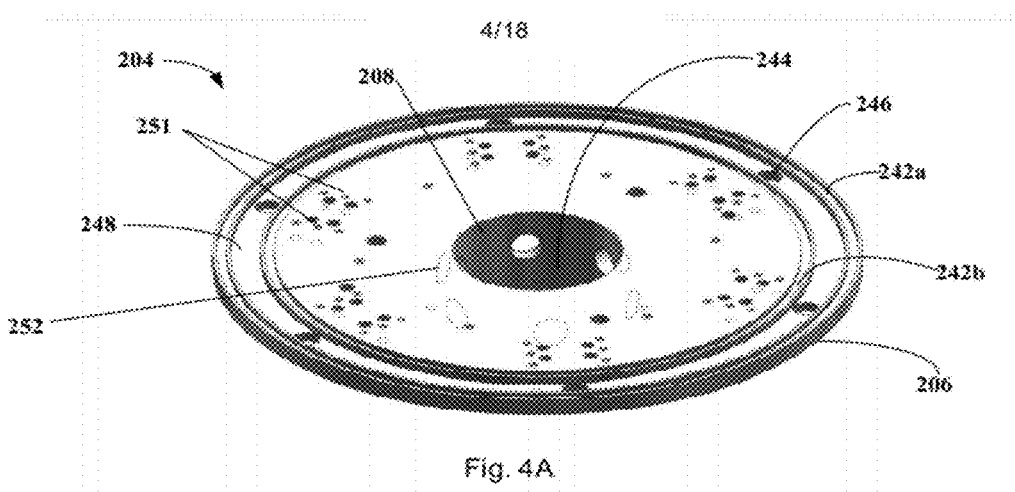
FIGS. 4A and 4B are a top perspective view and a bottom view of a manifold assembly configured for use in a chromatographic system.
Figure 4B:
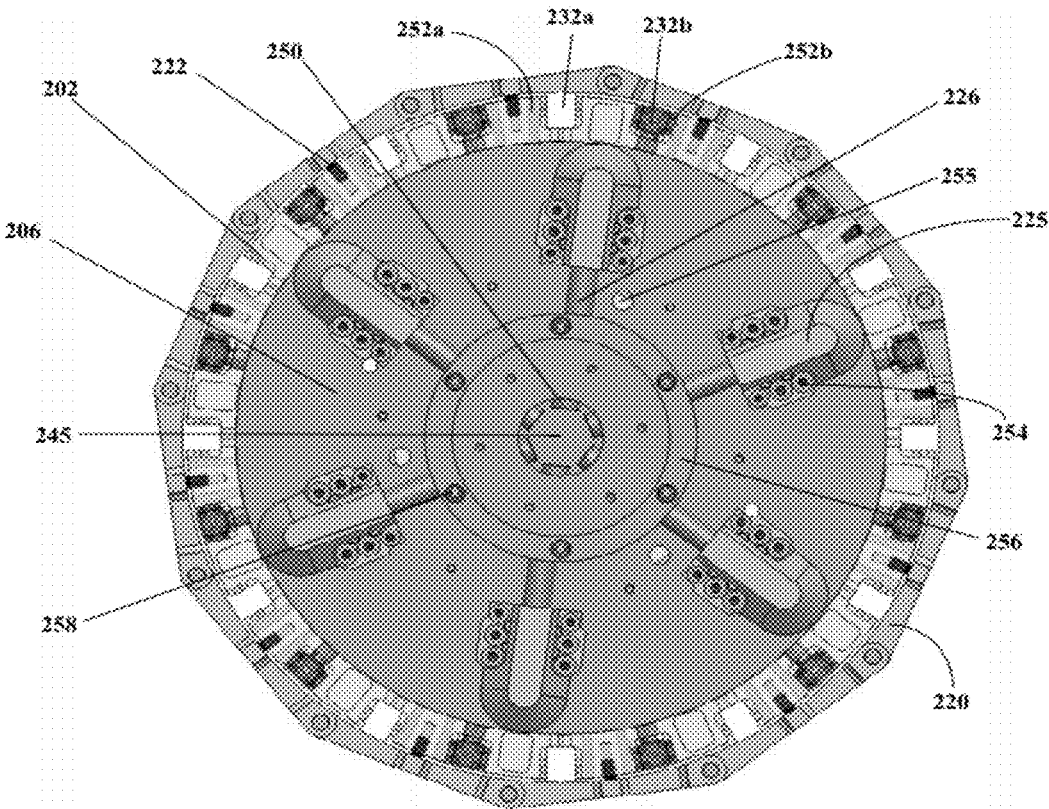

FIGS. 4A and 4B are a top perspective view and a bottom view of manifold assembly 204. The disk portion of the manifold assembly can include a circumferentially aligned drainage channel 248. An outer 242a and inner channel 242b can surround the drainage channel 248. The outer and inner channels, 242a and 242b, can support circular gaskets (not shown). When the top of manifold assembly is coupled to the bottom of the platter 202, the circular gaskets can press against the bottom of the platter 202 and prevent fluids from leaking from the drainage channel 248 during operation of the rotor assembly 200.

The drainage channel 248 can include a number of drainage holes, such as 246. Six drainage holes are shown in the FIG. 4A. The drainage holes can be each coupled to a manifold block, such as 225. The manifold disk portion 206 can include a number of apertures, such as 251, for fasteners, such as 254, that couple the manifold blocks, such as 225, to the disk portion.

An adjustable tube can be coupled to each manifold block 225. An aperture 252 in the column portion 208 of the manifold assembly can allow an end portion 250 of the adjustable tube to be inserted through the column 208 and to drain into a central hollow portion of the column 208. In FIG. 4B, end portions, such as 250, of adjustable tubes, such as 225, can be seen within the central drainage column 244 of the manifold column 208.

The manifold assembly 204 can be coupled to the adapter plate assembly 214 which includes an adapter plate (see FIG. 6) via mounting holes, such as 258, in the bottom ring portion 256 of the manifold assembly 204. Fasteners can be inserted through the mounting holes to couple the manifold assembly 204 to the adapter plate assembly 214. A bottom opening 245 in drainage column 244 can be coupled to drainage channels in the adapter plate assembly 214 to allow fluid to exit the drainage column 244 and travel through the adapter plate assembly into the reservoir 210.

The reservoir 210 can include a number of drainage tubes, such as 218a and 218b in FIG. 2. As previously described, reservoir 210 can be periodically drained via the drainage tubes. In one embodiment, the drainage tubes can pass through the bottom of the disk portion 206 of the manifold assembly 204 via apertures, such as 255. The platter 202 can also include apertures (not shown) that allow the drainage tubes to pass through the platter.

As is described with respect to FIG. 1, in embodiments described herein, flow paths can be split and then coalesced. As an example, in the rotor assembly 200, a single flow path starts in the mixing chamber 228 and then is split into 24 separate flow paths (see FIGS. 2 and 3). As is shown in FIGS. 4A and 4B, the 24 separate flow paths can coalesce into a single drainage channel 248. The single drainage channel 248 can split into 6 separate flow paths through the manifold blocks, such as 225, which then are coalesced into a common drainage column 244.

Referring to FIG. 4B, the diameter of the disk portion 206 of the manifold assembly is smaller than the diameter of platter 202. The smaller diameter of the disk portion 206 allows the flow windows on the bottom of the flow cells, such as 232a and 232b, to be accessed. Thus, if a light source is provided proximate to the top portion of the flow cells, light emitted from the light source that has passed through the flow cell and exited via the bottom window can be gathered. An instrument mount for providing a light source and gathering light exiting from a flow cell while the rotor assembly is rotating is described with respect to FIG. 8.

In FIG. 4B, the platter 202 is rendered as partially transparent. Thus, a portion of the return flow channel tubes associated with each flow cell can be viewed. For instance, return flow channel conduits, 252a and 252b, which are each next to flow cells, 232a and 232b, respectively are visible. Fasteners, such as 222, are also visible. The fasteners, such as 222, couple the return segment links to the platter 202.

In one embodiment, the return flow channel conduits can be formed by drilling into a solid portion of the platter 202. As previously described, the return flow channels, such as 252a and 252b, can route fluid that has exited the flow cells and entered into the return segment links to move towards the circumferentially aligned drainage channel 248 in the disk portion of the manifold assembly 204 and away from the edge of the platter 202.

The return flow channel can be positioned to the side of each flow cell (as opposed to below the cell) to allow access to the bottom windows of the flow cells. In other embodiments, such as to accommodate different instrumentation, the return flow channels can be routed along a different path. Further details of a return flow channels are described with respect to FIG. 5B.

FIG. 5A is a side cross sectional view of a rotor assembly 200 with an illustrated flow path. The flow path can start in solvent reservoirs 285 where one or more solvents can be delivered to the flow path. In some embodiments, a number of different solvents can be simultaneously delivered to the flow path where the fractions of solvent components in the solvent composition can vary over time. In this embodiment, the solvent reservoirs are not located on the rotor assembly 200. As previously described, in other embodiments, one or more solvent reservoirs can be located on the rotor assembly 200. For instance, a solvent reservoir can be associated with each or a portion of columns, such as 230a and 230b, on the platter 202. The one or more solvents can be delivered by a pump (not shown). An embodiment of a solvent reservoir located on a rotor assembly is described in more detail with respect to FIGS. 10A-10D.

Returning to FIG. 5A, as previously described with respect to FIGS. 2 and 3, a gas bearing support assembly can include or more flow conduits (see FIGS. 7A-7C and 8 for more details of the gas bearing support assembly 400). The one or more flow conduits can be part of a flow path, such as 260. The flow conduits in the gas bearing support assembly 400 can be used to deliver fluids, such as solvents to the mixing chamber 228. In one embodiment, a flow conduit in the gas bearing support assembly 400 can also be used to deliver a sample for use in a chromatographic process to the mixing chamber 228. In some instances, the sample can be mixed with one or more solvents in the mixing chamber 228.

In the mixing chamber 228, a number of mixing pins, such as 275, can mix one or more fluids entering the mixing chamber. The mixing pins can rotate according to the angular velocity of the rotor assembly 200. At typical rotational speeds, the mixing pins can tend to remove air from the fluid. Thus, when only a single fluid is delivered to the mixing chamber and a mixture of fluids is not created, an advantage of the mixing chamber 228 can be removing air from the single fluid prior to its entry into the columns, such as 230a and 230b.

The mixing chamber 228 includes a number of apertures, such as 276, that allow fluid to exit from the mixing chamber. In one embodiment, each aperture is in fluid communication with a chromatographic column where the column contains a single chromatographic stationary phase. In other embodiments, one aperture, such as 276, in the mixing chamber 228 can be in fluid communications with multiple chromatographic columns. For instance, in a tube-within-tube a tube design, a number of tubes can be placed within the interior of a hollow cylinder where each tube contains a separate chromatographic stationary phase. An entrance to each of the tubes can be provided near a top of the hollow cylinder that is in fluid communication with one of the apertures in the mixing chamber. During operation, fluid exits the mixing chamber via the apertures and then enters each of the tubes. The tubes can have circular or non-circular cross sections.

In another embodiment, a valve can be situated proximate to each aperture. The valves can be used to control a rate of fluid entering each aperture. For instance, the valves can be used to control a size of an opening associated with each aperture. In some instances, the valves can close to prevent fluid from exiting via a particular aperture. For example, if a leak is detected downstream of a first aperture, the valve associated with the first aperture can be actuated to prevent additional fluid from exiting via the first aperture.

A number of columns, such as 230a and 230b, can extend from the mixing chamber to the edge of the platter 202. In one embodiment, the columns can be arranged in symmetric pairs to help balance the rotor assembly 200 when it rotates. For instance, columns 230a and 230b can be a symmetric pair of columns with similar mass properties. However, as previously described, the mass properties of column pairs can vary from column pair to column pair.

In a particular embodiment, the columns can extend along a line that is perpendicular to the axis of rotation 265 through the center of the rotor assembly 200. In other embodiments, the columns can extend along a line that is not perpendicular to the axis of rotation (e.g., two angles can be defined relative to the axis of rotation that determines the line that each column follows such as two angles used in a spherical coordinate system). For instance, each of the columns can be sloped downward or upward from the center axis 265 of the rotor assembly to the edge of the platter 202. The platter 202 can be thicker or include additional support structure to support columns that extend above or below the platter 202.

As another example, rather than a single column 230a extending toward the edge of the rotor, the platter 202 can include two columns at this location one sloped downward and one sloped upwards that connect to the mixing chamber and lead to the edge of the platter 202. In yet another example, the platter 202 can include 3 columns, column 230a which is straight across the platter, a second column sloped upward above column 230a and a third column sloped downward below column 230a. Each of the columns can be connected to the mixing chamber 228 or can be connected to separate fluid reservoirs.

In yet other embodiments, an inner area through which fluid flows in the flow conduits between the mixing chamber 228 and the edge of the platter 202 can be constant. For instance, the inner area of the column 230a and the flow cell 232 can be approximately constant. In one embodiment, such as inside the flow cell 232 or column 230a, the inner area of flow conduit can remain constant but a shape of the perimeter of the inner area can change along the flow conduit. For instance, the shape of the inner area of the flow conduit can transition from a square of with an area to a circle of the same area where during the transition between the two shapes the area remains constant.

In other embodiments, the inner area of the flow conduits between the mixing chamber and the edge of the platter 202 can vary between the mixing chamber and the edge of the platter 202. For instance, a flow restrictor with a small inner area than the rest of the conduits can be placed near the end of column 230*a* or after flow cell 232 to slow down the flow velocity.

During operation, the rotation of the rotor assembly 200 can cause fluid to build up on side walls 266 of the mixing chamber 228. In one embodiment, a portion of the side walls 266 can be generally parallel to an axis of rotation of the rotor assembly 200 while other portions can be angled relative to the center axis of rotation. Other mixing chambers shapes are possible. For instance, a lower portion of the mixing chamber 228 can be a bowl shaped to some curvature profile.

When a fluid is added to the mixing chamber 228 while the rotor assembly 200 is rotating, a fluid head of some thickness 268 can build up on the side walls of the mixing chamber 228. Thus, boundaries of the fluid head can include a portion of the top, bottom and side walls of the mixing chamber and a free boundary that extends some distance (e.g., the fluid head thickness) into the mixing chamber 228. The free boundary can be approximately described as a cylindrical shaped wall of fluid that is parallel to an axis rotation of the rotor assembly 200.

As shown in FIG. 3, a top of the mixing chamber 228 can be partially covered but can include an aperture. In one embodiment, the aperture can be circular but other shapes can also be used. As described above, one or more flow conduits can be passed through the aperture to allow fluid to be delivered to the mixing chamber 228. As is described in more detail with respect to FIGS. 7A-7C, the top of the mixing chamber can be covered by a gas bearing.

The gas bearing can enclose the mixing chamber and can prevent fluid and fluid vapors contained in the mixing chamber 228 from escaping. The gas bearing can remain stationary while the rotor assembly 200 including the mixing chamber 228 is rotating. Thus, during operation, the mixing chamber 228 enclosure can be formed from a portion of components that can be rotating and a portion of the components that can be non-rotating. In other embodiments, an enclosure can be form formed between two components rotating at different rates. For example, the gas bearing that sits on top of the mixing chamber can be associated with a component that can remain stationary or rotate at a different rate than the rotor assembly.

In addition, a fluid enclosure including stationary and non-rotating components or components rotating at different rates is not limited to use as a mixing chamber. For instance, the mixing pins can be removed from the mixing chamber to form a fluid enclosure that is used as a fluid reservoir. Also, a similar enclosure can be used to drain fluid from the rotor assembly. In this example, a bottom portion of the rotor assembly 200 can rest on a gas bearing. The gas bearing can be stationary and include a chamber that is topped by the rotor assembly 200. A flow conduit that rotates with the rotor assembly 200 can extend from the rotor assembly 200 into the chamber to deliver fluid into the chamber while the rotor assembly is rotating. Then, fluid can then be extracted from the chamber.

As is described in more detail as follows with respect to FIG. 5A and FIGS. 5B, 5C, 7A, 7B and 7C. Along a flow path on the rotor assembly 200 that starts in the mixing chamber 228 and ends at some location, such as in the reservoir 210 or via an interface that allows the flow to leave the rotor assembly 200, the flow can be contained. One advantage of containing the flow in various enclosures along its path through the rotor assembly is safety. Many fluids that can be utilized with the devices described herein can be dangerous. For example, some fluid can be flammable while other fluids can be health damaging, such as being a cancer causing agent in humans. Thus, keeping the fluids contained in rotor assembly 200 along its flow path can provide for safer operating conditions than including open air interfaces on the rotor assembly 200 where fluids or fluid vapor can more easily escape from the rotor assembly 200 (If the fluids used with the rotor are not unsafe, than the rotor assembly can be designed that includes interfaces where the fluid is not totally contained, such as an open air interfaces where fluid moves through a space that is at least partially unenclosed).

Returning to FIG. 5A, the rotor assembly 200 can be configured such that a thickness of the fluid head 268 in the mixing chamber can be adjusted. For instance, thickness of the fluid head can be adjusted by changing the geometry of the flow path in the rotor assembly 200 so that the fluid head does not extend into an inner perimeter of the aperture in the top of the mixing chamber. To illustrate how the fluid head thickness 268 can be adjusted, first a flow path through the mixing chamber 228 to the exit 250 of the adjustable tube 226 is described including an initialization of the flow along this flow path. Second, an equilibrium condition is described where forces acting on the fluid in two segments of the described flow path can balance. Finally, adjustments to the configuration of the rotor assembly 200 that can affect the equilibrium condition including the fluid head thickness 268 are discussed. At the equilibrium condition, the fluid head thickness 268 in the mixing chamber can be a certain value. Thus, changing the equilibrium condition can change the fluid head thickness in the mixing chamber 228.

In the rotor assembly 200, a line 262 is drawn at a constant radius 264 from a center axis 265 of the rotor assembly. The flow path 260 is shown near the center axis 265 of the rotor assembly. The line 262 crosses the flow path through the rotor assembly 200 in the mixing chamber 228 and near the exit 250 of the adjustable tube 226. The exit 250 can drain fluid from the adjustable tube into to central drainage column 244 of the manifold assembly 204.

The rotor assembly 200 can rotate with an angular velocity about its center axis 265 when a force is imparted to the rotor assembly by a motor (not shown). As previously described, the centrifugal forces increase as a distance from the center axis of rotation 265 increases and the angular velocity of the rotor assembly increases. The centrifugal forces can move fluid through the rotor assembly 200.

For the purposes of discussion, two segments of the flow path through the rotor assembly 200 can be defined. A first flow path segment can be defined as starting at the wall of fluid on free boundary of the fluid head 268 in the mixing chamber 228 and moving outwards (increasing radius) to end within the return link 220. A second flow path segment can be defined as starting at the exit 250 and moving outwards (increasing radius) to end within the return segment link 220. The first and second flow path segments can be joined in the return segment link 220.

In one embodiment, to initialize the flow in the two flow segments, the rotor can be spun up from rest to a constant angular velocity. Fluid introduction can begin during spin up (prior to reaching the target angular velocity) or after the rotor assembly 200 has reached the target angular velocity. In some embodiments, residual fluid can remain in the rotor assembly from a previous run. The residual fluid can fill all or portions of the first and second flow path segments. Thus, a portion of the first and second flow path segments can be dry at initialization while other portions can include residual fluid.

During spin-up, fluid introduction can begin in the mixing chamber 228. Not all rotor assemblies 200 necessarily include a mixing chamber 228. In some embodiments, a rotor assembly 200 can have multiple fluid introduction points, such as separate introduction points for each column such that a common introduction point, such as 228, is not used. Thus, this example is provided for the purposes of illustration only.

Typically, for chromatographic separation process performed in the columns, such as 230a and 230b, fluid can be passed from one in end of the column to the other end of the column. In the embodiment in FIG. 5A, fluid can be introduced at the beginning of the column 270 that is closest to the mixing chamber 228 and flow through the column to an end 280. To get flow to the beginning of the column 270, various flow paths can be configured. For instance, a flow path is shown in FIG. 5A where flow starts near the center of the rotor in the mixing chamber and moves continually away from the center on its way to the beginning of the column. In other embodiments, the flow can start at a radius than is greater than the radius of the beginning of the column and then move towards the center of the rotor until it reaches the beginning of the column 270 and reverses direction to flow into the beginning of the column 279.

In yet other embodiments, chromatographic columns, such as 230a and 230b, can be located on a return flow segment. First, the flow can move from a center 265 of the rotor assembly 200. At some radial distance from the center of the rotor back it can be turned towards the center of the rotor to enter a return flow segment. The chromatographic column can be located on the portion of the flow path where the flow is moving towards the center of the rotor, i.e., the return flow segment. For example, a flow path can be configured where the flow moves from the end 280 of the column 230a to the beginning of the column 270 while a chromatographic separation process is performed in the column 230a. In this example, instrumentation, such as a flow cell or a mass spectrometer can be located at the beginning 270 of the column 230a, i.e., the instrumentation configuration can reverse of what is shown in FIG. 5A.

In other embodiments, a chromatographic column does not have to be straight. The column can be curved in some manner from the center of the rotor to the edge of the rotor. In general, a flow conduit that follows some path in the rotor assembly 200 can be used to perform a chromatographic process. The chromatographic flow conduit can be straight or curved. In the chromatographic flow conduit, flow can be generally moving towards the center of the rotor assembly or away from the center of the rotor assembly 200. Prior to reaching a beginning of the chromatographic flow conduit where the flow enters, the flow can be moving along a flow path where the radial distance from the center of the rotor assembly is varying including where the radial distance is increasing, decreasing, constant or a combinations thereof along the flow path. Further, the flow can be moving at radial distances that are greater or lesser than the radial distance where the flow enters the chromatographic flow conduit. Finally, after reaching an end of the chromatographic flow conduit and exiting, the flow path can be moving along a flow path where the radial distance from the center of the rotor assembly is varying including where the radial distance is increasing, decreasing, constant or combinations thereof along the flow path.

During different modes of operation of the rotor assembly 200, reverse flow configurations can also be achieved. For instance, if the flow is blocked from reaching exit 250, such as via actuation of a valve, on the return flow path segment from the edge of the platter 202 towards the center 265, then fluid that is at a radial distance above the valve location can begin flowing back towards the edge of the platter 202 and then reverse directions and flow back towards the center 265 of the rotor assembly 200 via the flow cell 232 and the column 230a. Thus, in particular embodiments, flow paths can be configured where the flow can move in one direction at some times and in an opposite direction other times.

Returning to FIG. 5A, during flow initialization, the fluid introduced into the mixing chamber 228 can exit the mixing chamber 228 and can enter into the columns, such as 230a and 230b. Each column can include two detachable caps, such as, 272 and 274, which are shown coupled to column 230b. In one embodiment, the two detachable caps can be threaded and screwed onto the ends of each column. The caps can each include a flow conduit. In particular embodiments, the flow conduit in each detachable cap is the same area as flow conduit in its associated column.

The first attachable cap, such as 272, can provide an interface for the column to the liquid introduction assembly including the mixing chamber 228. In some embodiments, the first attachable cap can include a surface, such as a seat or a groove, on which a gasket of some type is placed. The gasket can be used to form a seal between the mixing chamber assembly and the first attachable cap. Similarly, the second attachable cap, such as 274, can provide an interface between each column and an associated flow cell, such as 232. The second attachable cap can include surfaces for interfacing with the flow cell, such as protuberance that is inserted into the flow cell 232 as well as a seat or grooves for holding one or more sealing mechanisms, such as a gasket.

If fluid is first introduced into the mixing chamber during spin-up, then the rotor assembly 200 may have to reach an angular velocity threshold before fluid can enter into the columns, such as 230. When the angular velocity threshold is reached, the fluid in the mixing chamber 228 can enter into the column 230a and progress down from a beginning 270 of the column to an end 280 of the column to establish a flow path 278 within the column 230a. The angular velocity threshold can depend on a chromatographic packing material property, such as a size of the packing material particles, used in the chromatographic column 230. Typically, smaller diameter packing particles can require a greater RCF to move the flow through the packing material as compared to larger diameter particles. Since RCF is proportional to the angular velocity squared, larger RCF's can be generated by increasing the angular velocity of the rotor assembly 200.

After the flow path 278 is established in the column 230a, the fluid can exit the column to establish a flow path 286 in the flow cell 232. The flow cell 232 includes optical windows, such as 282, and apertures 284 that allow access to the optical windows. Next, the flow can exit the flow cell 232 to establish a flow path 288 in the return segment link 220. As the flow progresses through the return segment link 220, the first flow path segment from the mixing chamber 228 to the return segment link 220 can fill with fluid and the flow can begin entering into the second flow path segment. The flow can then begin moving from the return segment link 220 towards a center of the rotor assembly 200 and eventually reach the exit 250 of the adjustable tube 226.

Figure 5B:
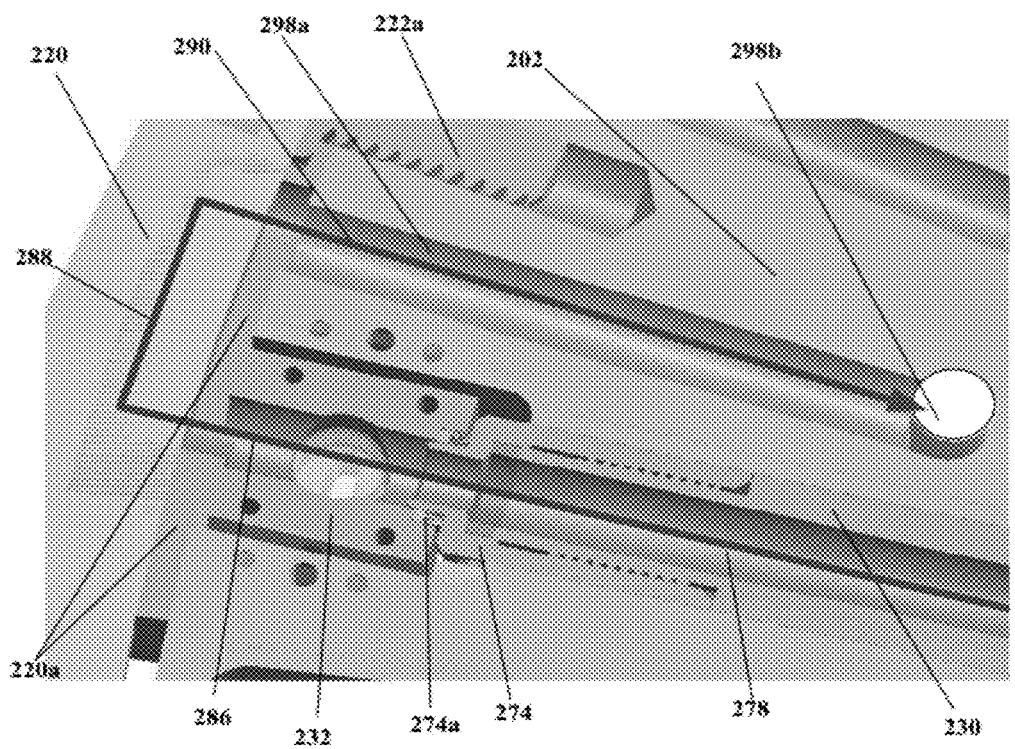
FIG. 5B is a top perspective cross sectional view of a platter, chromatographic column, a flow cell, a return segment link and a return flow channel with an illustrated flow path.
Figure 5C:
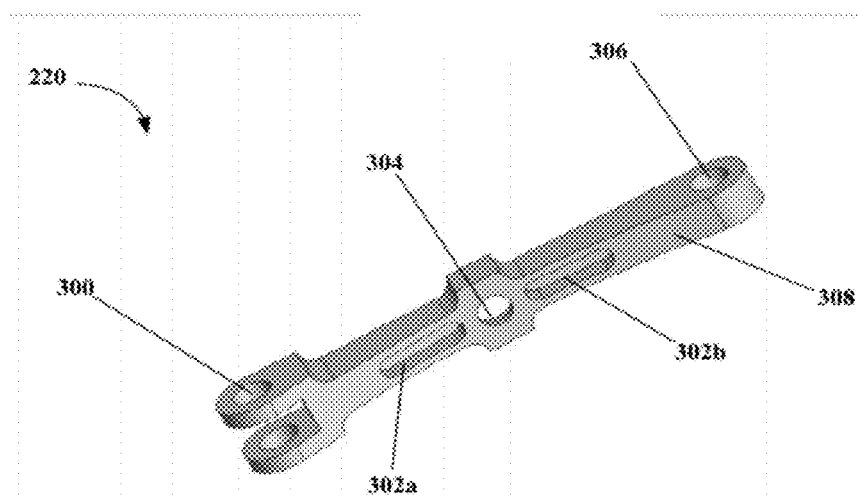
FIG. 5C is a perspective view of a return segment link.

In the second flow path segment where the flow is generally moving from the platter's 202 edge to the center axis 265, the fluid can exit the return segment link 220, to establish flow path 290 in a return flow channel (More details of the flow path in the return segment link 220 and a return flow channel are described with respect to FIGS. 5B and 5C.). The flow can exit the return flow channel and begin filling the drainage channel 248 to establish a flow path 292 in the drainage channel. As described with respect to FIG. 4A, the flow 292 can receive flow from a number of return flow channels associated with different columns. Two gaskets can be used to prevent fluid in the drainage channel 248 from escaping. Cross sections of gaskets, such as 275a and 275b, are indicated in FIG. 5A.

In other embodiments, the second flow path segment can receive only fluid from the first flow path segment. For instance, the second flow path segment can comprise flow conduits that receive only fluid associated with the flow through the column 230a and flow cell 232 and not other columns. In this embodiment, additional return flow conduits (not shown) can be used. For instance, one manifold block 225 and one adjustable tube 226 can be associated with one return flow channel from each column, such as 230a, and the drainage channel 248 can be eliminated. As previously described, coalescing the flows from multiple columns in the drainage channel can reduce an amount of flow conduits that are used in the rotor assembly 200. One advantage of reducing the flow conduits can be reduced manufacturing costs.

After the flow enters the drainage channel 248, it can exit through one or more apertures into one of the manifold blocks, such as 225, to establish a flow path 294 within the manifold block 225. The manifold block 225 can be connected to adjustable tube 226. The flow can exit the manifold block 225 to establish a flow path 295 in the adjustable tube 226. The flow path in the adjustable tube 226 can end at the exit 250.

Fluid can be introduced into the mixing chamber 228 until the fluid head thickness 268 reaches the same radial location 264 of the exit 250. At this point, if no additional fluid is introduced to the mixing chamber, to satisfy an incompressible Bernoulli's equation, the fluid head thickness 268 can reach equilibrium at about the same level of the exit 250. Because of viscous and other non-linear effects, such as precession of the rotor assembly about its center axis 265, the radial locations of the exit 250 and the fluid head thickness 268 may not be exactly the same but can be at approximately the same distance. If additional fluid is introduced into the mixing chamber 228, the fluid head thickness can reach a radial location that is smaller the radial location of the exit 250. When the fluid head thickness 268 is greater than its equilibrium value, the flow in the rotor assembly 200 can attempt to return to the equilibrium condition. As a result, flow can start moving out of the mixing chamber 228 and flowing through the rotor assembly 200. Excess fluid can spill out of the exit 250.

If at some time, fluid introduction is stopped in the mixing chamber, then fluid can spill out of the exit 250 and into the drainage column until the fluid head thickness 268 reaches about at the same radial location as the exit 250. When the fluid is continually introduced into the mixing chamber drainage column 244, the flow can continually exit through each of the adjustable tubes and exit into the drainage column 244 to establish a flow path 296 in the drainage column. The flow can exit the drainage column 244 through a bottom of the manifold assembly 204 and eventually reach an interior of the reservoir, such as 210a. Details of the flow path after it exits the manifold assembly 204 are described in more detail with respect to FIG. 6.

The radial location of the fluid boundary surfaces associated with the fluid head and the exit 250 can vary. In the embodiment in FIG. 5A, during rotation, the centrifugal forces can cause the flow to build up against a gravitational pull such that it extends from a bottom of the mixing chamber to top of the mixing chamber and from a bottom of the adjustable tube to the top of adjustable tube across each of the exits, such as exit 250. As a result of at least surface tension and gravity effects, the boundary surface of the fluid head from the top to the bottom of the mixing chamber or the boundary surface of the fluid across the exit 250 can be curved such that the radial distance from the center axis of rotation 265 can vary across the fluid boundary surfaces at these locations. As the angular velocity of the rotor assembly is increased, the radial variations along the fluid boundary surface can decrease, i.e., the surface can become more vertically aligned.

In one embodiment, to reach the equilibrium described above where the fluid head thickness 268 is at about the same radial location 264 as the exit (i.e., the fluid head thickness 268 is at about line 262), the rotor assembly 200 can be spun up to a constant angular velocity (Also, as previously described, fluid can be introduced to the mixing chamber during spin-up of the rotor assembly where the angular velocity of the rotor assembly is increasing over time.). After the rotor assembly 200 reaches some target angular velocity, fluid can be added to the mixing chamber 228 where it can progress through the rotor assembly 200 until the flow reaches the exit 250 and begins to flow out the adjustable tubes 226. A rate that fluid is added to the mixing chamber 228 can be used to control a flow velocity in the rotor assembly 200 including a flow velocity in the columns, such as 230a and 230b.

As previously described with respect to FIG. 1, after a determination is made that a steady flow velocity is established in the columns, such as 230a and 230b, a sample can be introduced at some location on the rotor assembly 200. For example, the sample can be added to the mixing chamber 228. From the mixing chamber, the sample can be dispersed to each of the columns. In another example, as is described in more detail with respect to FIG. 9A, a sample can be injected near a head of each column, such as 230a and 230b. When the column includes a chromatographic packing material, the sample can undergo a chromatographic separation, which can be analyzed via measurement made using the flow cells at the end of each column, such as 232.

The equilibrium fluid head thickness 268 can be adjusted by changing the distance 264 of the exit 250 from the center axis of rotation 265. For example, the equilibrium fluid head thickness can be selected so that during operation the fluid head does not extend into the aperture in the seat 240 of the mixing chamber 228. As previously described, the aperture in the seat 240 of the mixing chamber can provide an entrance for one or more flow conduits that can deliver fluid into the mixing chamber 228.

In general, in various embodiments, a rotor assembly 200 can include 1) a first flow path segment where the flow moves along some flow path such that a final radial distance from the center 265 along the flow path is greater than the initial radial distance and 2) a second flow path segment, connected to the first flow path segment, where a final radial distance of the flow path segment is smaller than the initial radial distance of the flow path segment. An exit can be placed at the final radial distance of the second flow path segment such that fluid can leave the second flow path segment. The radial distance from the center axis 265 where the exit is located on the second flow path segment can determine an equilibrium location in the first flow path segment. Fluid can be introduced into the first flow path segment at some rate. The rate that the flow is introduced into the first flow path segment can be used to control a flow velocity through the first flow path segment and the second flow path segment. As is described below, the fluid introduction rate and associated flow velocity can be relatively insensitive to changes in the angular velocity of the rotor assembly 200.

Returning to FIG. 5A, in yet other embodiments, the exit radius, such as 264, of exit 250 of each of the adjustable tubes 226 can be adjusted. The exits, such as 250, for each of the adjustable tubes can be located at the same or different distances from the center axis 265 of the rotor assembly 200. The adjustable tubes, such as 226, can include threads 297 that mate with threads in the manifold assembly 204 and threads (not shown) that mate with threads in the manifold block 225. The adjustable tubes can be screwed to different depths into the manifold block 225 to change the radial distance 262 of the exit 250. A lock nut 224 can be used to fix be used to secure adjustable tube 226 such that the radial distance of the exit 250 remains fixed during rotation of the rotor assembly 200.

In particular embodiments, the rotor assembly 200 can include a mechanism that allows the radial distance of the exit 250 to be dynamically changed. For instance, the ends of each of the adjustable tubes, such as 226, can include a flexible end piece that is elastically extendable. In operation, a force can be applied to each of the flexible end pieces to change the radial distance of the exit 250 associated with the flexible end piece. For instance, when force is not applied to the flexible end piece, the exit 250 can be near the wall of the drainage column 244 and when a force is applied, the exit 250 can be stretched toward the center of the drainage column 244.

An advantage of configuring the rotor assembly 200 with a first flow path segment to the rotor edge connected to a second flow path segment from the rotor edge is that once an equilibrium condition is established, the flow velocity can be controlled by changing the flow introduction rate in the first flow path segment, such as but not limited to via the mixing chamber 228. When ideal conditions are approached, the flow introduction rate to the first flow path segment needed to obtain a particular flow velocity in the columns can be essentially independent of the angular velocity for a wide range of angular velocity operating conditions.

Further, the flow introduction rate in the mixing chamber 228 needed to obtain a particular flow velocity in the rotor assembly 200 can be much less sensitive to changes in angular velocity as compared to other flow configurations where the flow is not is routed back away from the edge of the rotor. For example, the flow can be allowed to exit at the rotor edge, such as from return segment link 220, rather than allowed to exit at 250. In one embodiment, a fluid collection ring, such as 210, can surround the rotor edge and receive fluid, such as fluid exiting from the return segment links (In this example, the return segment link does not turn the flow back towards the center 265 of the rotor assembly). For this configuration as compared to a configuration shown in FIG. 5A where the flow is routed back toward the axis of rotation 265, the exit velocity at the rotor edge and the flow through the columns can be much more sensitive to changes in angular velocity. Typically, for this type of configuration the exit flow velocity can increase as the angular velocity of the rotor assembly is increased because RCF increases.

With respect to FIGS. 5B and 5C, further details of the flow near the rotor edge are described. In particular, FIG. 5B is a top perspective cross sectional view of the platter 202, column 230, which can contain packing material (referred to also as a stationary phase material) used in a chromatographic process (not shown), a flow cell 232, a return segment link 220 and a return flow channel, such as 298a and 298b, with an illustrated flow path. The column 230 can rest on platter 202. The platter 202 can include a groove in which the column rests.

As previously described, a detachable cap 274 can be coupled to the end of the column 230. In one embodiment, the detachable cap 274 can include a protuberance that is configured to fit into an opening in the flow cell 232. A gasket 274a can surround the protuberance to form a seal between the detachable cap 274 and the flow cell. The platter 202 can include a recessed portion into which the flow cell 232 can be placed.

The flow cell 232 can include an opening that allows fluid to travel into the return segment link 220 (see 252a and 252b in FIG. 5C). Flow can exit the channel in return segment link 220 and enter into a return channel, 298a and 298b. A gasket 220a can be placed between the return segment link 220 and the edge of the platter 202. The gasket 220a can be configured to keep fluid from leaking at the interface between the return segment link 220 and the flow cell 232 and the interface between the return segment link 220 and the return flow channel, 298a and 298b.

The platter 202 can include an acceptor for a fastener 222a. The fastener can be inserted through an aperture in the return segment link 220. Tightening the fastener can increase a force on the gasket 220a between the return segment link 220 and the platter 202. The force on the gasket 220a can provide better seal integrity, which can prevent leakage. The return flow channel can include a portion 298a that goes into the platter 202 through an outer edge of the platter 202 and a portion 298b that goes down through the platter (portion 298a and 298b are at angle to one another). The portion 298b can exit into the drainage channel 248.

FIG. 5C is a perspective view of an embodiment of a return segment link 220. The return segment link 220 can include apertures 300 and 306 that allow the return segment link 220 to be coupled to two other return segment links. A pin can be inserted through each of the apertures 300 and 306 to couple the return segment link to the other return segment links. When all of the return segments links are coupled together, an unbroken chain is formed around the edge of the rotor.

The return segment link 220 can include an aperture 304. As illustrated in FIG. 5B, a fastener can be inserted through the aperture 304 to couple the return segment link to the platter 202. In one embodiment, the return segment link 220 can include two recessed portions 302a and 302b. Each of the recessed portions can allow flow between a flow cell and a return flow channel in the platter 202. Thus, in one embodiment, each return segment link 220 can be associated with the flow from two different chromatographic columns.

An inner surface of the return segment link 220 can be curved. The surface curvature can be selected such that the when the return segments are linked, the inner surfaces of the return segment links 220 form a circle that is slightly larger than the circle around the edge of the platter 202. With the surface curvature 308, the forces generated from the fastener that is attached through aperture 304 can be better distributed. A better distribution of forces over surface 308 can improve the seal integrity between the return segment link 220 and the outer edge of the platter 202.

FIG. 6 is a side view of the rotor assembly 200 with a cross-sectional view of a reservoir 210 and a partially transparent view of the adapter plate assembly 214. The adapter plate assembly 214 can include an adapter plate 318. The manifold assembly 204 can be coupled to the adapter plate 318 via fasteners, such as 320. The tapered shaft 212, which can be connected to a motor (not shown), can be coupled to a disk portion 214a of the adapter plate assembly 214 via a fastener 316. The tapered shaft 212 can be inserted into a bottom portion of the adapter plate assembly 214 and secured to it via the fastener.

The reservoir 210 can also be coupled to the adapter plate assembly 214, such as to the disk portion 214a of the adapter plate assembly. The adapter plate 318 can include one or more flow conduits. The flow conduits can allow flow exiting from the drainage column 244 in the manifold assembly 204 to enter into the adapter plate. One or more gaskets (not shown) can be used for sealing purposes where the fluid interface on the manifold assembly 204 meets the fluid interface on a top of the adapter plate 318.

Fluid can enter from the manifold assembly 204 into the adapter plate 318 and then travel through one or more flow conduits to exit the adapter plate via one or more apertures 310. In a particular embodiment, the flow can travel in an increasing radial direction from the center of the rotor assembly to enter into the reservoir 210. The flow can then travel into an interior portion of the reservoir, such as 210*a*.

A seal can be formed at the fluid interface between the reservoir 210 and the adapter plate 318. In one embodiment, a channel can run around an edge of the adapter plate 318 which can be sealed by the gaskets 314*a* and 314*b*. An advantage of this approach is that the adapter plate 318 can be inserted into an interior portion of a single piece reservoir drum, such as 210. The reservoir drum 210 can include a circular ledge 322 or a number of arms that extends from an inner surface of the reservoir drum. The adapter plate 318 can rest on this ledge or the arms. The disk portion 214*a* of the adapter plate assembly can be configured to be inserted through the circular ledge 322 or arms. The circular ledge or arms can include mounting points for attaching the reservoir drum to the adapter plate 318.

In particular embodiments, the reservoir drum can include multiple pieces, such as two halves or four quarters. The adapter plate 318 can include flow conduits that extend from the adapter plate 318 that are configured to be inserted into apertures in the reservoir drum 210 or the reservoir drum 210 can include flow conduits that extend from the reservoir drum and can be inserted into the adapter plate. The reservoir drum 210 can be formed in multiple pieces to allow for assembly. This configuration can be used an alternate to using the sealed channel around the edge of the adapter plate.

Different rotor assemblies can have different manifold assembly designs and different waste reservoir designs. For example an inner diameter of the waste reservoir drum 210 or an outer diameter of the manifold assembly 204 can be larger. Different adapter plates 318 can be used to accommodate the different configurations of the manifold assembly 204 or the reservoir drum while allowing a portion of the adapter plate assembly that is coupled to the tapered shaft 212 to be reused.

The rotor assembly described with respect to FIGS. 5A, 5B, 5C and 6 comprises a number of modular components. The modular architecture is provided for the purposes of illustration only and is not meant to be limiting. An advantage of some modular architectures can be ease of assembly, disassembly, more configuration options and reduced manufacturing costs. A disadvantage of some modular architectures can be that more modular components can introduce more fluid interfaces that necessarily need to be sealed and thus, more potential locations for leaks.

To eliminate potential leak points, in some embodiments, some components can be integrally formed to perform functions associated with two separate components. For instance, in some embodiments, a manifold assembly can include a waste reservoir that is integrally formed with the manifold assembly to eliminate the flow conduits through the adapter plate 318. As another example, the mixing chamber enclosure is formed as a separate component from the platter 202. In other embodiments, the mixing chamber enclosure can be an integral component of the platter 202. Further, the manifold block 225 and adjustable tube 226 can be formed as a single flexible conduit.

In yet another example, the platter 202 includes a number of grooves on which columns can be rested. Thus, the columns can be removed, such as for the purposes of packing or cleaning the columns and then be placed back on the platter. In other embodiments, the columns can be integrally formed into the platter 202. For instance, a solid disk from which the platter is formed can have a number of holes bored into it that can serve as columns. In another embodiment, metal can be poured over a conduit structure that can be subsequently removed to provide an internal conduit system within a platter such as 202.

In yet another embodiment, a number of open channels can be formed on a first plate and then the channels can be covered. For instance, a second plate can be adhered to the second plate to cover the channels. After the channels are covered each channel has an entrance and an exit. For instance, a number of radially aligned channels directed can be formed on a first "washer" shaped disk where each channel progresses from an inner radius to an outer radius of the washer. Then, a second structure, such as a second washer of a similar dimension of the first washer with a flat surface can be adhered to the first washer to form enclosed channels. In particular embodiments, open channels can be formed in each of two separate plates, such as forming half cylinder channels in each of the plates. When the two separate plates are joined, enclosed channels with a circular cross section are formed.

Figure 7A:
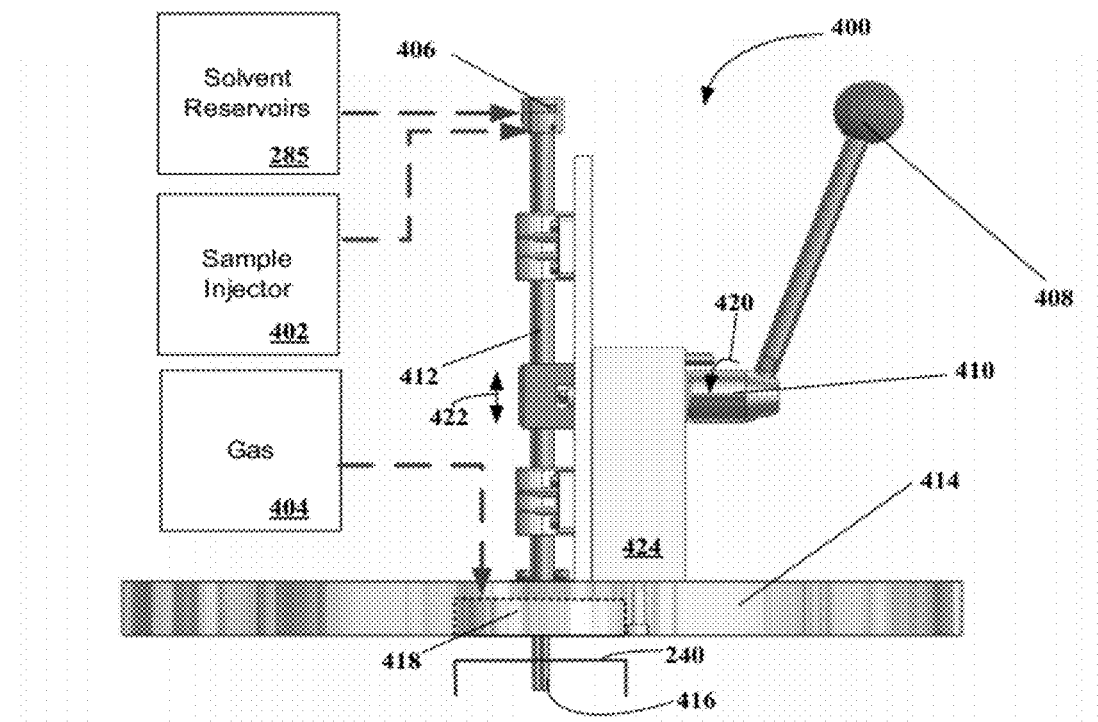
FIGS. 7A-7C are side and perspective views of a gas bearing support assembly.
Figure 7B:
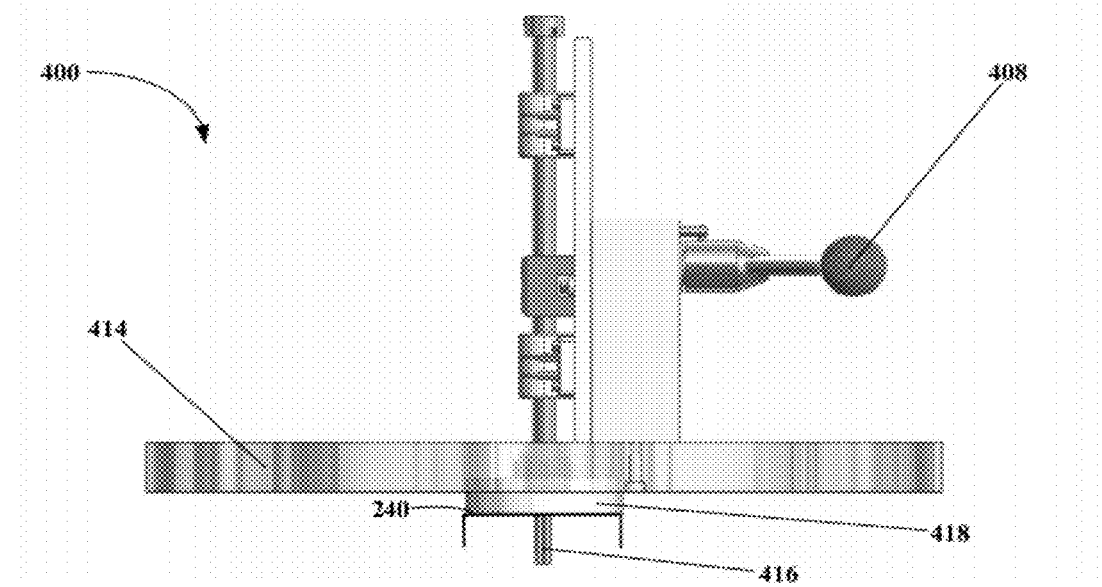
Figure 7C:
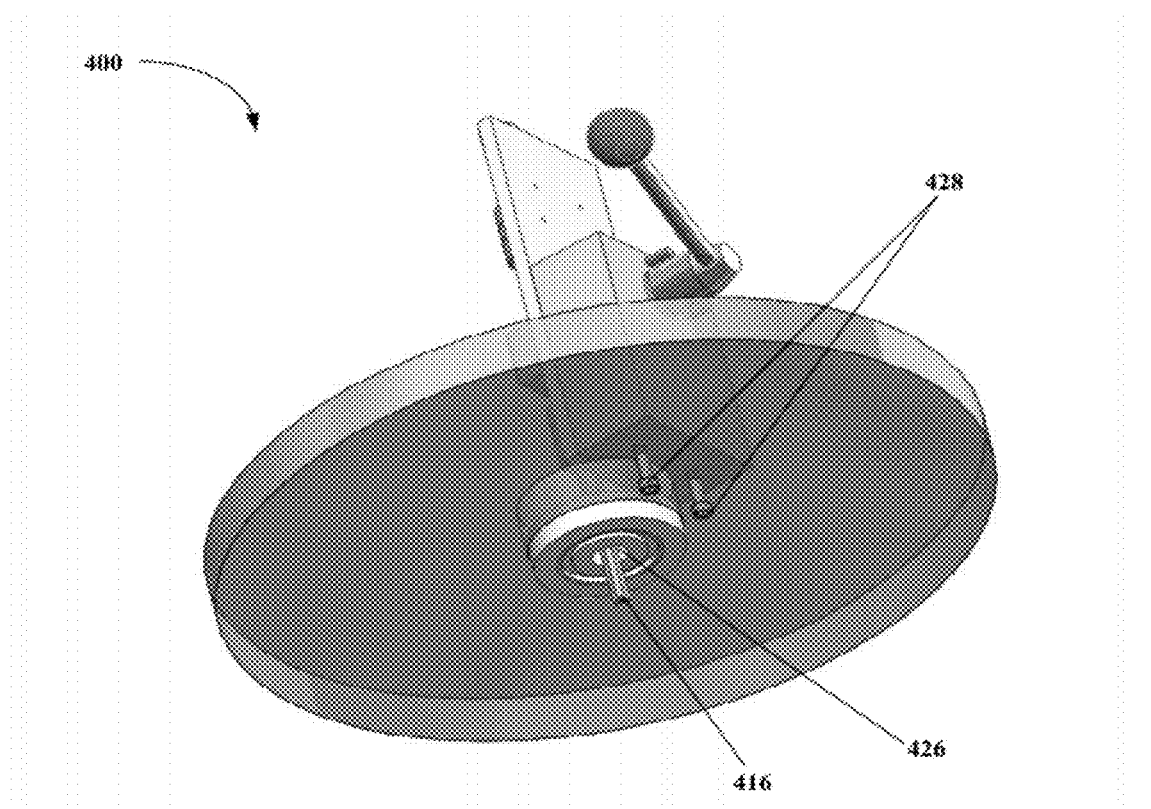

FIGS. 7A-7C are side and perspective views of a gas bearing support assembly 400. The gas bearing support assembly 400 can be placed upon a drum type rotational mechanism that rotates a rotor assembly (see FIG. 8). The lid 414 can act as a lid to the drum. The lid can be composed of a hard transparent material, such as bullet-proof glass. The bullet proof glass can allow the operation of the rotor assembly to be observed while providing protection from parts that can be flung from the rotor assembly as a result of a mechanical failure of some type. In other embodiments, the lid can be formed from another type of material, such as non-transparent material.

During rotation of the rotor assembly 200, the gas bearing 418 can rest on the seat 240 of the rotor assembly, such as 200. The weight of the gas bearing support assembly 400 that is transferred through the gas bearing 418 and onto seat 240 can help stabilize a rotor assembly, such as 200, during rotation. For example, the weight of the gas bearing support assembly 400 can help to lessen precession effects that can occur while the rotor assembly is rotating.

The gas bearing support assembly 400 can include a number of flow conduits. The flow conduits 416 can run through a hollow shaft 412 and extend through an aperture in a center portion 426 of the gas bearing 418. As previously described, when the gas bearing 418 rests on seat 240, the flow conduits can extend into a chamber located below the seat 240, such as a mixing chamber 228. Further, the bottom of the gas bearing 418 can act as a portion of a lid to the mixing chamber to help contain fluid in the mixing chamber.

In a particular embodiment, three flow conduits 416 are shown extending through the gas bearing assembly. The three flow conduits can be used to deliver a variety of fluids to the mixing chamber, such as two different solvents and a sample fluid. The concentrations of the different solvents can be varied over time to form an elution gradient. In other embodiments, more or less flow conduits can be run through shaft 412 and into the mixing chamber. In some instances, a gas bearing assembly can be used for the purposes of rotor assembly stabilization and may not include any flow conduits. In another instance, for a particular run, one or more flow conduits can be inactive and not utilized.

The shaft 412 can include one or more fluid interfaces allow one or more flow conduits from the solvent reservoirs 285 and/or the sample introduction mechanism 402 to be connected to the flow conduits running through a center portion of the shaft. For instance, the shaft 412 can be coupled to a cap 406 with interfaces that can connect to flow conduits, such as flexible tubing, from the solvent reservoirs 285 and the sample introduction mechanism 402. One or more pumps associated with the solvent reservoirs and the sample introduction mechanism 402 can move fluid into the shaft.

In one embodiment, one or more of the pumps can be a positive displacement pump, such as a piston driven pump. In another embodiment, one or more of the pumps can be positive displacement pump, such as a buoyancy pump. A compressed-air-powered double-diaphragm pump is one example of a buoyancy pump. This type of pump can run on compressed air and has a minimal amount of moving parts. In yet another embodiment, the pump can be a gas amplifier pump.

The gas bearing 418 can be porous. The pores in the gas bearing allow gas to flow through it. When the gas bearing 418 rests on seat 240 and the rotor assembly is rotating, the gas pumped through the gas bearing 418 can form a thin layer between the gas bearing 418 and the rotating seat 240. The thin layer of gas minimizes friction between the gas bearing 418 and the seat 240. Some times the seat 240 and the gas bearing can come into contact. This contact can eventually wear out the gas bearing 418.

The gas bearing can include an interface to a gas source 404, such as a pressurized argon container. During operation, the pressurized argon can flow through the gas bearing 418. An advantage of argon is that it is the third most common gas in the atmosphere and it is inert. However, other gases can be used and Argon is provided for the purposes of illustration only.

The gas bearing support assembly 400 can be configured to allow the shaft 412 and the gas bearing 418 to be raised or lowered, 422. The gas bearing support assembly is shown in a raised position in FIG. 7A and a lowered position in FIG. 7B. In one embodiment, the gas bearing support assembly can be raised or lowered via lever 408. The lever 408 can coupled to a rotatable shaft 410 where a rotation 420 of the shaft 410 raises or lowers the shaft 412 and the gas bearing 418. The rotatable shaft 410 can be supported by support block 424. The support block 424 can be coupled to the lid 414 via one or more fasteners, such as 428.

Figure 8:
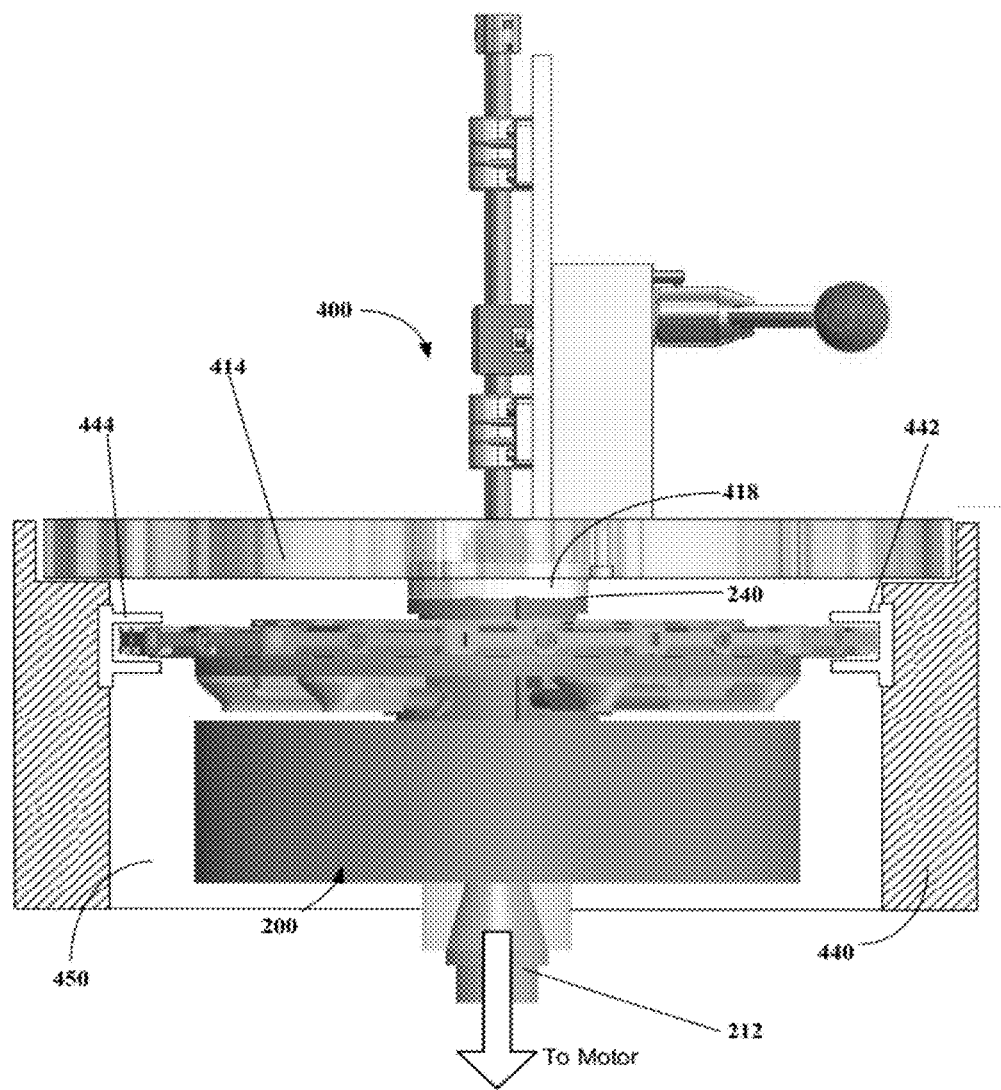
FIG. 8 is side view of a rotor assembly, gas bearing assembly within a containment structure and including instrument mounts.

FIG. 8 is side view of a rotor assembly 200, gas bearing support assembly 400 within a containment structure 440 and including instrument mounts, such as 444 and 442. The gas bearing support assembly 400 is shown in engaged position where the gas bearing 418 rests on the seat 240 of the rotor assembly 200. The gas bearing lid can rest on a ledge of the containment structure 440.

In one embodiment, the containment structure 440 can be drum shaped and can be formed from a metal. The containment structure 440 can include an aperture that allows the tapered shaft 212 to be coupled to a motor that is located below the rotor assembly 200. The motor can be used to impart an angular velocity to the rotor assembly 200.

One or more apertures can be provided in the containment structure or the lid 414 (not shown). The apertures include conduits that allow gasses to be evacuated from the chamber 450. In one embodiment, the chamber 450 can be sealed so that a vacuum of some level can be established in the chamber. To improve sealing, a gasket can be placed between the lid 414 and the containment structure 440. Further, fasteners can be used to more securely couple the lid 414 to the containment structure. The one or more apertures in the lid 414 or the containment structure 440 can be connected to a vacuum pump. When the vacuum pump is activated a vacuum of some level can be established in the chamber 450. The vacuum pump can also be used for safety purposes to limit an accidental build-up of dangerous gasses in the chamber 450, such as flammable gas.

One or more instrument mounts, such as 442 and 442, can be coupled to the containment structure. In one embodiment, each instrument mount, such as 442 and 444, can include a light source and a light gathering device. The light source and light gathering device can be aligned with the flow cell windows on the rotor assembly 200 as previously described. To allow the light source and the light gathering device to be aligned with the flow cells, which are near the edge of the rotor assembly 200, the instrument mounts can extend over and under a portion of the rotor assembly 200.

In a particular embodiment, two fiber optic cables can be attached to each instrument mount, such as 442 and 444. A first fiber optic cable can be coupled to a light source, such as light source that emits photons at one or more different wavelengths. A second fiber optic cable can be coupled to a photomultiplier tube. The second fiber optic cable can receive photons emitted from the first fiber optic cable that have passed through a flow cell. The gathered photons can be passed to a photomultiplier tube. The photomultiplier tubes and the lights sources can be located outside of the containment structure 440.

The signal generated from the photomultiplier tube can be used to analyze constituents of the fluid passing through the flow cell. The light sources associated with each instrument mount can produce different wavelengths, such as but not limited to a visible wavelengths, ultra violet wavelengths and infrared wavelengths. In various embodiments, zero, one or more than two instrument mounts with light emitting and light gathering capabilities can be used.

In another embodiment, the instrument mounts, such as 442 and 444, can include gas bearings. The gas bearings can help to stabilize the rotor assembly 200 during rotation and can help to prevent the rotor assembly from colliding with the instrument mounts, such as 442 and 444. A flow conduit, such as flexible tube, can be coupled to each of the instrument mounts to provide gas for the gas bearings. The flow conduit can be coupled to a gas source that is used with each of the gas bearings.

The instrument mounts, such as 442 and 444, can include a rotatable joint that allows a portion of the instrument mount to rotate. Via the rotatable joint, a portion of the instrument mount, such as the upper portion of the instrument mount can be rotated, such as rotated upwards, to allow the rotor assembly to be placed in or removed from the containment structure 440.

In one embodiment, when there is enough clearance between the sides of the containment structure and the edge of the rotor assembly, a portion of the instrument mount, such as the portion including the fiber optic cables can be located on retractable arms. The retractable arms can be retracted to allow a rotor assembly to be placed in or removed from the containment structure. The retractable arms can be extended to allow the fiber optic cables or any other instrumentation on an instrument mount coupled to the retractable arms to be placed in a position above and/or below the rotor assembly 200.

As the rotor assembly rotates, various rotor locations can rotate in a repeating manner past the instrument mounts. To keep track of the current rotor location, such as a rotor location at which a measurement is made. An indexing system can be provided. The indexing system can be used to uniquely identify a location where a measurement is made on the rotor assembly. A generated index can be associated with a measurement made using the instrumentation associated with the instrument mounts.

As an example, the rotor assembly 200 can include an identifier such as markings that allow a rotor location to be determined. For instance, the platter 202 of the rotor assembly 200 can include visible markings that uniquely identify a location, such as location where each column is placed. The marking can be a symbol, such as a number and/or letter or a bar-code. As another example, RFID tags storing an identifier can be placed at various locations around the edge of the rotor assembly 200, such as a location where each column is placed.

A detector can be located on the instrument mount that is configured to detect the identifiers as they pass by the instrument mount. For instance, a camera can be used to detect an identifier, such as a symbol or a bar-code. As another example, a laser and a detector can be used to read an identifier, such as a bar-code. In yet another example, an RFID tag reader can be used to receive an identifier from an RFID tag placed on the platter.

During operation, many measurements can be made. The measurements can be associated with a particular chromatographic column. The amount of measurements that are made can depend on an angular velocity of the rotor assembly and length of time over which measurements are made. A detected identifier can be used as an index to map a set of measurements to a particular feature of the rotor assembly, such as to a particular column and associated flow cell. The indexed measurements can be used to generate a time varying profile of the measurements associated a particular chromatographic column.

FIG. 9A is a top view of an embodiment of a rotor assembly configured for use in a chromatographic system. Parts of the rotor assembly have been previously described with respect to FIG. 3. A power generation ring 333 can be coupled to the rotor assembly. The power generation ring 333 can include components of an electric generator, such as one or more coils of wire, and voltage conversion circuitry.

When used as an electric generation, the power generation ring 333 can be moved past magnets, such as magnets mounted on the instrument mounts described with respect to FIG. 8. As the coils move past the magnets, a current can be induced in the one or more wire coils. The generated electricity can be used to power devices on the rotor assembly. In another embodiment, the power generation ring 333 can include a number of batteries that are evenly distributed around the rotor assembly for balance. These batteries may or may not be chargeable via an electric generator located on the rotor assembly.

In yet another embodiment, a brush interface can be used to transfer power to the rotor assembly 200. For example, a conductive stripped can be placed around an edge of the containment structure 440 shown in FIG. 8. One or more arms with conductive brushes or some other contact mechanism can be extended from the rotor assembly 200 such that the conductive brushes contact the conductive strip, which is stationary, to deliver power to the rotor assembly. The conductive strip can be insulated so that the entire device is not electrified. In another example, a portion of the rotor assembly 200, such as the tapered shaft 212 can include an insulated conductive strip. Conductive brushes, which are stationary, can be located within the containment structure 440 that contact the insulated conductive strip on the rotor assembly. Electricity can be transferred between the metal brushes to the rotor assembly while it is rotating to power various devices located on the rotor assembly.

The voltage conversion circuitry can condition electricity received from an off-rotor source or power generated on-rotor for use with various devices located on the rotor assembly 200. One or more electrical conduits can lead from the power generation ring 333, such as conduit 334 to allow various devices to receive power. The conditioned electricity can be used to power electronically actuated valves, communication devices, on-rotor instrumentation, on-rotor sensors and environmental control devices, such as heating elements as well as to charge on-rotor batteries.

In FIG. 9A, the electrical conduit 334 is shown coupled to heating elements, 329 and 331, and to a sample introduction mechanism 325. The heating element rings, such as 329 and 331, can include a single electrical heating coil or multiple electrical heating elements that receive power from the power generation ring 333. A controller can be associated with one or both of the heating element rings, i.e., one controller for both rings or a separate controller for each ring. The one or more controllers can be configured for controlling a heat output of each of the heating element rings. In one embodiment one or both of the heating element rings can include one or more heating elements associated with each column where the heating elements for each column can be individually controlled. Temperature sensors can be located along the columns and control, such as a target temperature value, can be based upon data received from the temperature sensors.

In one embodiment, a sample introduction mechanism 325 can be located on a rotor. For instance, the sample introduction mechanism 325 can include a fluid interface, such as an electronically actuated valve, that connects a sample reservoir in the sample introduction mechanism to each of the columns and allows samples stored in the sample reservoir to be injected into each column. The sample introduction mechanism 325 can include one or more on-board injectors, such as one or more pumps, that allow a fluid stored in the sample reservoir to be injected into each column. In one embodiment, the injector can be a syringe pump.

In addition, the sample introduction mechanism can include one or more refill ports, such as 327, that are each connected to a sample reservoir. The refill ports can allow the sample reservoirs to be refilled. In particular embodiments, a single sample reservoir can provide samples to multiple columns. For instance, one sample reservoir can supply two or more columns where a single refill port, such as 327, is associated with the reservoir. Further, the sample used in each sample reservoir can vary from reservoir to reservoir. Thus, during operation, a number of different samples can be chromatographically processed simultaneously on the rotor. In other embodiments, when multiple sample reservoirs are used, the sample reservoirs can include separately controlled injectors. The injectors can be separately controlled to allow different samples to be introduced at different times relative to one another. The sample introduction mechanism 325 can include a controller for controlling devices located on the sample introduction mechanism, such as sample injectors or controllable valves.

The rotor can include on-board circuitry 337, such as processor, memory, battery and/or a communication interface. In one embodiment, circuitry 337 can include a wireless communication interface that allows communication between the rotor and a remote device, such as a system management device, such as the system management described with respect to FIG. 1. The circuitry 337 can include a communications bus that allows data to be transmitted from the circuitry 337 to the various devices. For instance, the circuitry 337 can receive commands from a remote device that are transmitted to a particular device on the rotor assembly, such as the power generation ring 333, heating element rings, 329 or 331, the sample introduction mechanism 325 or an adjustable valve.

A number of devices that generate data on-board the rotor can be connected to the communications bus 341 via a wired communication link, such as 339. In other embodiments, wireless communication links can be used to provide communications between the various devices on the rotor. An advantage of wireless links is that the wiring paths through the rotor assembly can be minimized. For example, various devices can include wireless transmitters/receivers that allow for communications with the circuitry 337.

Devices can generate data that is sent to the circuitry 337 via wireless and/or wired communication links. The circuitry 337 can store and/or send the data to a remote device. For example, the rotor can include a number of sensors such as but not limited to temperature sensors, flow rate sensors, flow level sensors (e.g., the reservoir 210 or the mixing chamber 228 can include a flow level sensor), pressure sensors and combinations thereof. Data from the sensors can be transmitted to a remote device via the circuitry 337. In other embodiments, particular devices can include their own communication interface that is not connected the circuitry 337. For instance, the sample introduction mechanism 325 can be configured to communicate directly with a remote device rather than through an intermediary device, such as circuitry 337.

As another example, the rotor can include on-board instrumentation that generates measurement data. The on-board instrumentation can communicate with circuitry 337 to send data to a remote device. In some embodiments, the data can be sent in real-time, i.e., as it is generated. In other embodiments, one or more devices can include a memory that allows data to be stored and then later transmitted to a remote device. The memory can also serve as a back-up data source where data is both transmitted and real-time and stored to memory, such that if any of the real-time data is lost, such as due to a transceiver malfunction, data can be recovered from the memory.

FIG. 9B is a side view of an embodiment of a rotor assembly configured for use in a chromatographic system including a fraction collection mechanism 350. In general, the fraction collection mechanism receives eluents eluted from a chromatographic enclosure. Thus, the fraction collection mechanism can be considered an eluent reservoir. The location of this fraction collection mechanism is provided for illustrative purposes only. Different rotor configuration can have different column and flow path configurations where a different placement of the fraction collection mechanism may be utilized.

In one embodiment, a fluid interface, such as a valve 352, can connect the fraction collection mechanism to flow path located in a return flow channel on the platter 202. As is described with respect to FIGS. 5A and 5B, the return flow channel can be coupled to an exit of a flow cell, such as 232 via a return segment link 220. The valve 352 can be opened and closed at various times to allow fluid that has exited the flow cell 232 to enter into the fraction collection mechanism 350 or by-pass the fraction collection mechanism 350. The valve 352 can be opened and closed while the rotor assembly is rotating.

In particular embodiments, the valve 352 can receive commands to open and close that are initiated on a device that is located off of the rotor. The remote device based upon information, such as measurements made via the flow cell, can determine when to open and close the valve and then send a command that causes the valve to open or close. In another embodiment, a controller located on the rotor assembly can make this determination and in response can send a command to the valve 352 to either open or close.

The fraction collection mechanism 350 can include one or more chambers for storing collected fractions. For instance, the fraction collection mechanism 350 can include four chambers 356 with four valves 354 that are individually controllable to direct fluid to each of the four different chambers. The chambers, such as 356, can each include an access aperture that allows a collected fraction to be extracted. For instance, in some embodiments, fractions can be collected via the apertures, after a run is completed and the rotor assembly is at rest.

A fraction collection mechanism, such as 350, can be associated with one or more columns. For instance, a single fraction collection mechanism can be configured to receive fractions from a single chromatographic column or can be configured to receive fractions from multiple columns. The number of fraction mechanisms on the rotor assembly can vary depending on a mapping between each fraction collection mechanism and a number of columns it serves as well as a total number of columns on the rotor. Further, when fraction mechanisms are employed, a fraction collection mechanism does not have to be associated with every column on the rotor. Thus, a number of fraction collection mechanisms on the rotor assembly can vary for different rotor assembly configurations.

In yet other embodiments, a variable volume eluent capture device, such as 350, can come after the detectors, such as a flow cell. A variable volume eluent capture device can include a wireless remote controlled electric motor that turns a lead screw inside a chamber, such as a cylindrical chamber. Onto the lead screw can be attached a piston-like sealing washer. As the lead screw turns, the piston-like sealing washer can move towards the outside of the chamber thereby allowing liquid to flow at a rate that is affected by the rate of movement of the piston-like sealing washer.

A variable volume eluent capture device can be incorporated into the reservoir, such as 210, previously described. In another embodiment, a device, such as a reverse syringe pump, can be used as a variable volume eluent capture device. In some cases, it can desirable to have multiple chamber variable volume eluent capture devices on the end of each column such that fraction collection is possible. In this case, a multiport valve can be added between the column and the variable volume eluent capture devices.

Figure 9C:
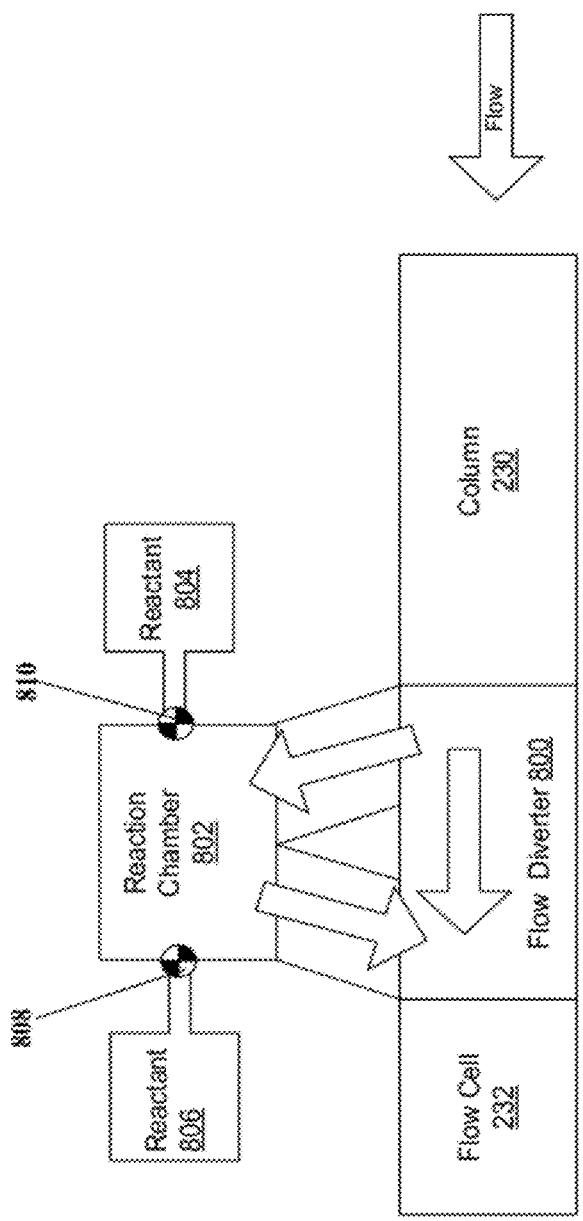
FIG. 9C is a block diagram including a reaction chamber located between the end of a column and a flow cell.

FIG. 9C is a block diagram including a reaction chamber located between the end of a column, such as 232 and a detector or structure associated with a detector, such as flow cell. In some instances, after a chromatographic separation, a chemical reaction can be performed on analyte leaving a chromatographic enclosure, such as column 232. The reaction can be performed to allow the analyte allow to be better identified with a particular detector. For instance, if an analyte, pre-reaction, does not fluoresce, it can not be detected by a fluorescence detector, such as a LIF detector (see Instrumentation section below). Via a chemical reaction, the analyte can be altered to produce products with enhanced detection characteristics, such as products that are detectable with a particular type of detector.

In one embodiment, a flow diverter, such as 800, can be used to divert a flow leaving the column, such that it either moves directly to a detector, such as flow cell 232 or is diverted into a reaction chamber, such as 802, before it reaches the flow cell. The reaction chamber 802 can include access ports that allow one or more different reagents, such as 804 and 806, to be added alone or in combination to the reaction chamber 802. The access ports can be controlled by valves, such as 808 and 810. In embodiments described herein, all or a portion of the columns can include reaction chambers, such as 802. Further, a reaction chamber, such as 802 can receive an analyte from one or more different columns.

The reaction chamber can include an ultrasonic vibration generator. In one embodiment, the ultrasonic vibrations can be generated by a piezoelectric element. The ultrasonic vibrations can enhance reaction rates of the analyte and reagent ensuring completeness of the chemical reaction. In one embodiment, the reaction chamber 802 can be located between the column 230 and flow cell without use of a flow diverter, such as 800. In this embodiment, reagents can be added to the reaction chamber when desired or the flow can be allowed to pass without adding reagents. In yet other embodiments, multiple reactions chambers can be used, such as a series of reaction chambers where a multi-step reaction is performed.

In other embodiments, another type of energy source can be used to affect a reaction, such as to increase a reaction rate in the reaction chamber 802. For instance, a microwave source can provide microwaves to the reaction chamber. In another example, a temperature control mechanism can be used to heat or cool the reaction chamber as needed.

Figure 10A:
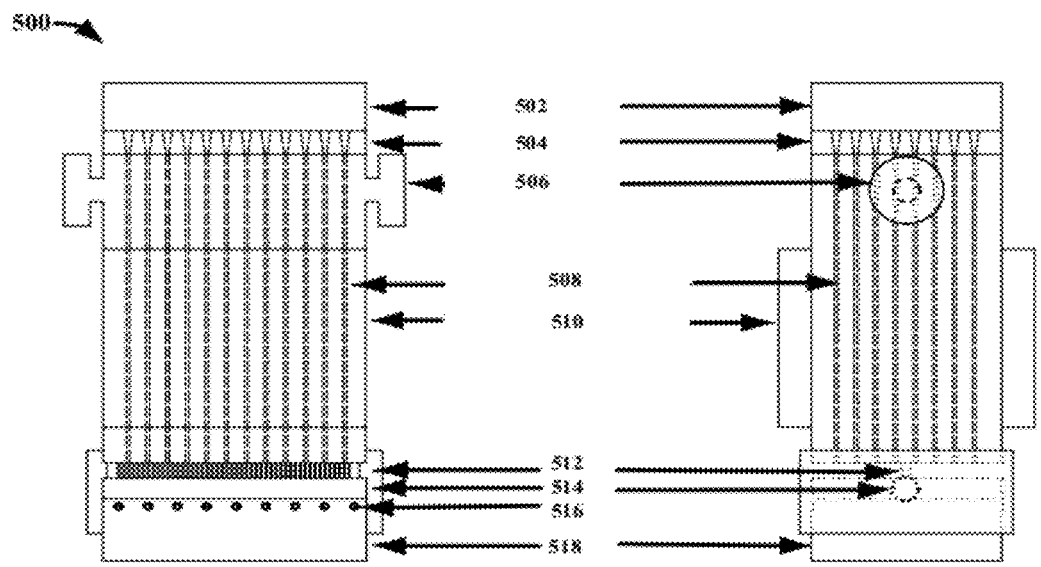
FIG. 10A is a front and side view of a bucket assembly including a plurality of columns for performing chromatographic separation.
Figure 10B:
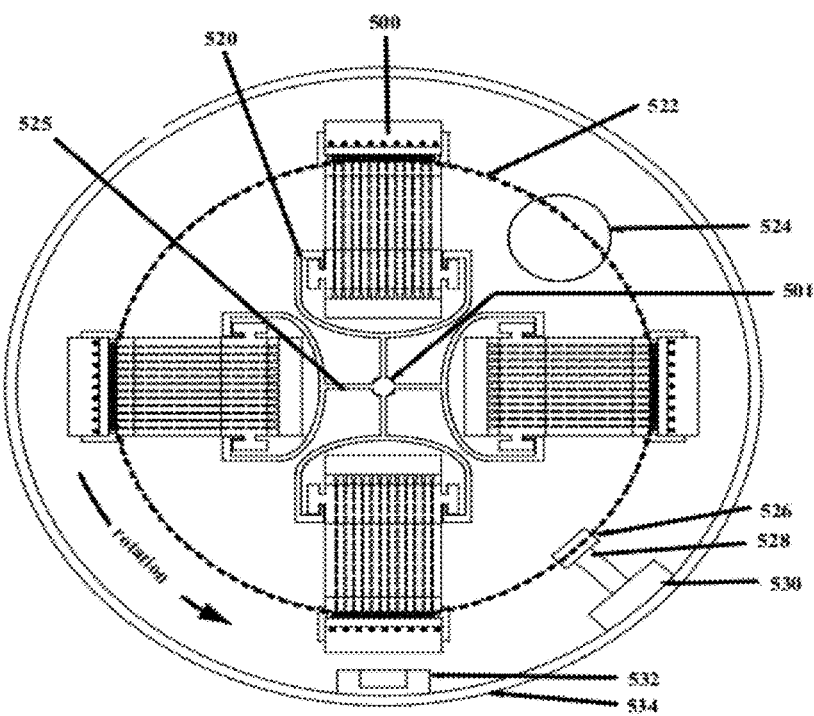
FIG. 10B is a top view of a rotor assembly including a plurality of buckets during rotation.
Figure 10C:
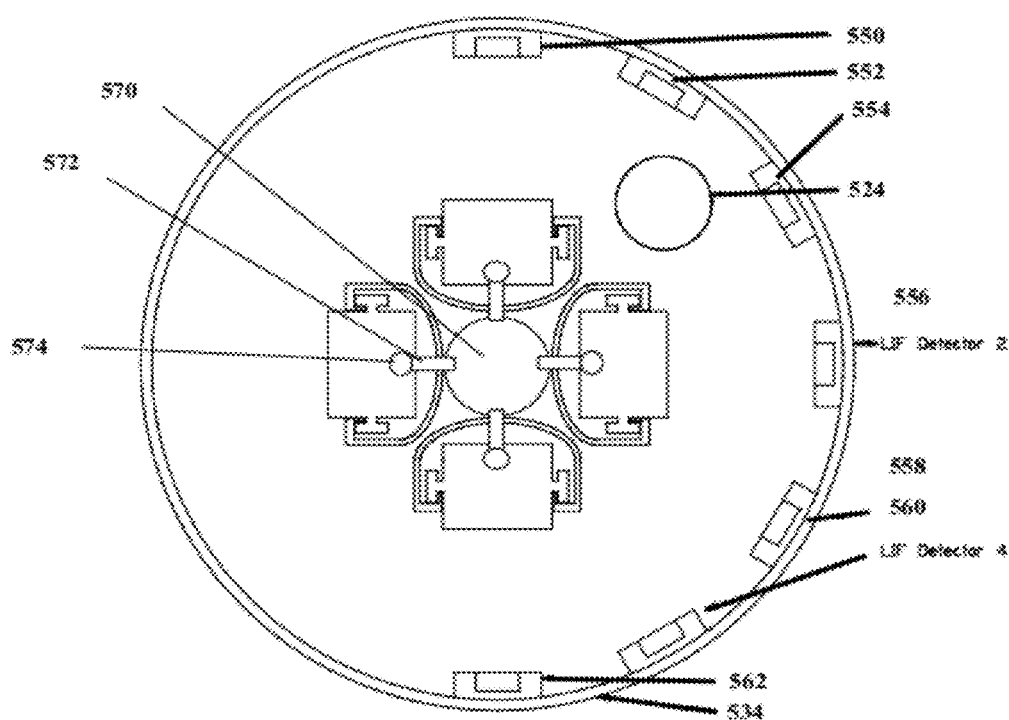
FIG. 10C is a top view of a rotor assembly including a plurality of buckets at rest.
Figure 10D:
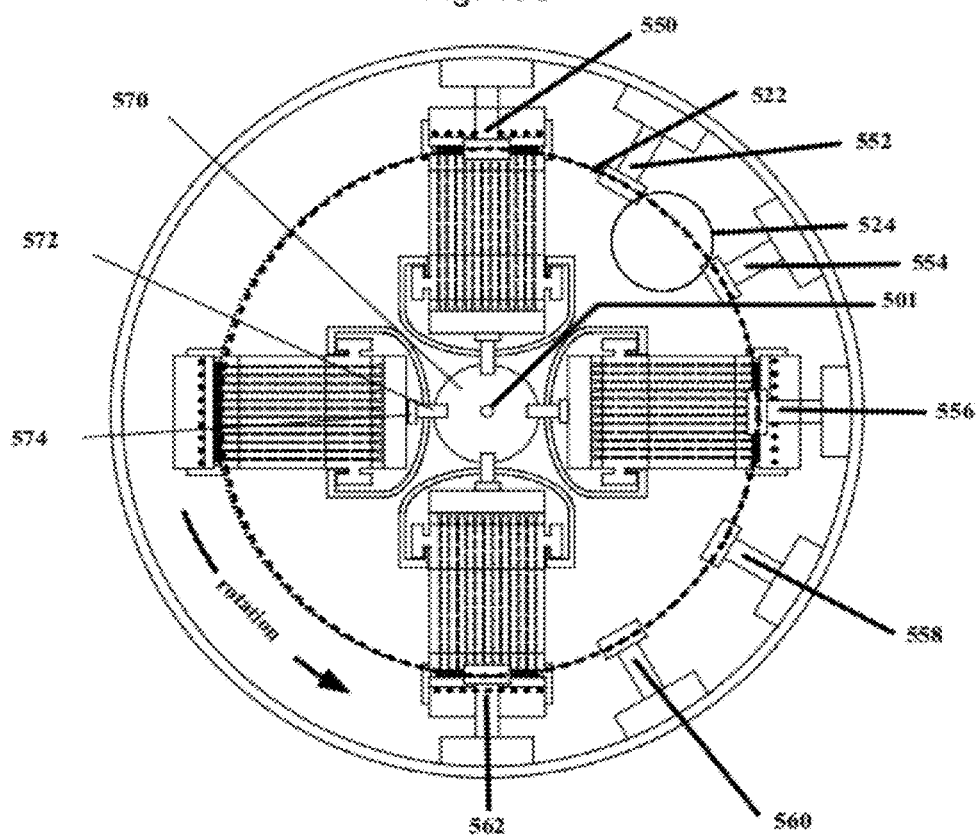
FIG. 10D is a top view of a rotor assembly including a plurality of buckets during rotation.

With respect to FIGS. 10A-D, an alternate system for performing centrifugal liquid chromatography is described that incorporates a swinging bucket design. FIG. 10A is a front and side view of a bucket assembly 500 including a plurality of columns for performing chromatographic separation. The bucket assembly is detachable. In operation, as is shown in FIGS. 10B-D, the bucket assembly 500 can be coupled to a rotor assembly and rotated. The rotation can impart centrifugal forces to the bucket assembly. The bucket assembly can be coupled to the rotor assembly via a rotor support 506. During rotation, the centrifugal forces can drive fluid down a number of chromatographic columns in which a chromatographic separation is performed.

The bucket assembly 500 can include a solvent reservoir 502 that can be pre-loaded with a solvent and a sample mixture. The solvent reservoir 502 can be coupled to a large number of chromatographic columns 508 via a well plate 504. During rotation, the solvent and sample can be driven through orifices in the well plate 504 via centrifugation. In one embodiment, the well place can include 96 orifices coupled to 96 columns.

In another embodiment, each bucket assembly can be coupled to a central reservoir associated with the rotor assembly that rotates with the buckets. The central reservoir can be located near an axis of rotation of the rotor assembly (see FIG. 10C). The central reservoir can control a fluid mixture delivered to each rotor assembly including a solvent composition for an elution gradient and a sample. In a particular embodiment, a flexible fluid interface, such as a flexible hose, can be attached from central reservoir to the solvent reservoir 502 on each bucket, such that fluid from the central reservoir can be delivered to the solvent reservoir 502. As will be described below, a position of the bucket assembly can change during spin-up from a vertical position to a horizontal position. The flexible fluid interface can be used to accommodate a change in position of the bucket assembly during spin up.

A pack 510 including a battery and a transceiver can be coupled to the bucket assembly 500. The battery can be used to power a flow rate control device 514. In one embodiment, the flow rate control device 514 can be a motorized stopcock. The motorized stopcock can be coupled to each of the columns. When the stopcock is closed liquid does not flow through the columns 508. When the stopcock is partially open, liquid can flow through the columns 508. When liquid starts moving down the column, air displaced from the columns can be released via vents, such as 516.

A position of the stopcock can be used to affect a flow rate in each of the columns. As the stopcock is more fully opened, the flow rate can be increased through the columns. In one embodiment, a flow rate control device 514, such as the stopcock can be remotely controlled. A remote device can send commands to request a particular stopcock position via the transceiver. Data associated with flow rate control device 514, such as its current state, can be sent to a remote device via the transceiver.

In a particular embodiment, a sample reservoir can be located above the solvent reservoir 502, separate from the solvent reservoir, so that the sample can initially be kept separate from the solvent. A mechanism, such as a valve can be used that allows the sample to be introduced into the solvent reservoir. In operation, the solvent can first be allowed to propagate through the columns to establish a flow in the columns. Then, the sample can be introduced into the solvent reservoir, such as 502, and a mixture of solvent and sample can be allowed to propagate down the columns 508. The solvent reservoir 502 can include a mixing mechanism, such as an ultrasonic mixer, that mixes the solvent and sample, after the sample is introduced.

A number of flow cells 512 can be located near the end of the columns 508. The flow cells can be used to perform a number of optical measurements of flow exiting the columns, 508. Details of some of the optical measurements that can be made are described as follows with respect to FIGS. 10B-10D. After exiting the flow cells, waste can be collected in the solvent receptacle 518.

FIG. 10B is a top view of a rotor assembly 525 including a plurality of buckets, such as 500. The top view is during rotation of the rotor assembly 525 and the buckets. The rotor assembly 525 can be configured to rotate around an axis 501. The rotor assembly 525 can include a number of mounts, such as 520, for attaching the bucket, such as 500. In the embodiment of FIG. 10B, the rotor assembly 525 can include 4 mounts for attaching 4 separate buckets, such as 500, if desired. The rotor assembly 525 can be surrounded by a containment structure 534, such as a metal drum.

At rest, the buckets, such as 500, can be aligned vertically with the gravity vector (see also FIG. 10B). During operation of the rotor assembly 525, as its rotational speed increases, the bucket 500 can swing up to a horizontal position as shown in FIG. 10B. In a horizontal position, the transceivers on the bucket can pass over a transceiver location 524 located on a bottom portion of the containment structure 534. Via the transceiver location 524 data transmitted from each of the buckets can be sent to a remote device or a remote device can send data or commands to each of the buckets, such as commands to a flow control device located on each of the buckets.

In alternate embodiment, a number of buckets, such as 500, can be mounted to a platter, such as platter as described with respect to FIGS. 2-8 so that the bucket is always in a horizontal position. Utilizing a platter design, the buckets can be connected to a fluid reservoir, such as a mixing chamber 228, for solvent and sample introduction and can be connected to another flow path that allows waste to be collected from the buckets in a reservoir, such as reservoir 210 previously described. Further, the bucket can be configured in flow path where a velocity generated by the flow introduction rate is substantially independent of the angular velocity, i.e., where the flow moves from the center to an edge of the platter and then returns back towards the center.

Two instrument assemblies are shown. Each instrument assembly can include a mount, such as 530, which is attached to the containment structure 534, a retractable arm 528 coupled to the mount and one or more detector elements, such as 526, coupled to the retractable arm 528. The arm 528 is in an extended position while an arm 532 is in a retracted position. When the arm 528 extended position, the detector elements 526 can located over an optical flow cell line 522 so that measurements involving the flow cells can be made. When an arm, such as 532, is in a retracted position, then instrumentation associated with the instrument assembly may not be used.

In some embodiments, a plurality of instrument assemblies can be available. However, every instrument assembly and its associated instrumentation may not be used for every run of the chromatographic system. When an instrument assembly is not in use, it can stowed, such as in a retractable position, as shown in FIG. 10B.

FIG. 10C is a top view of a rotor assembly including a plurality of buckets at rest. FIG. 10D is a top view of a rotor assembly including a plurality of buckets during rotation. The rotor assembly includes a central reservoir 570. The central reservoir can control fluid composition for each of the buckets. Fluid from the central reservoir 570 can be delivered to the buckets via a flexible fluid interface 572. The flexible fluid interface 572 can include a detachable connector 574 that can be linked to an acceptor on the bucket.

In particular embodiments, the central reservoir 570 can include multiple chambers for storing different mobile phase fluids. Further, the reservoir can include a gradient former and a mixing chamber. The gradient former can control a composition of a mobile phase fluid using different fluids. In addition, the central reservoir can include a sample introduction mechanism and one or more sample reservoirs arranged to introduce a sample. The sample can be combined with a mobile phase fluid in the mixing chamber. The mixing chamber can be in fluid communication with each of buckets via the flexible fluid interfaces, such as 572.

In one embodiment, a flexible power interface (not shown), such as power cable, can be coupled to the flexible fluid interface 572. The flexible power interface can be attached to an acceptor on the bucket to deliver power to devices, such as controlled valves on the bucket. The flexible power interface can be coupled to a central portion of the rotor assembly. As previously described with respect to FIG. 9B, during rotation, a brush interface can be used to deliver power to a rotatable element from a power source that is located off of the rotatable element.

A brush interface can be used to deliver power to a central portion of the rotor assembly while it is rotating. Thus, the buckets can also receive power from the off-rotor power source via the flexible power interface between the central portion of the rotor assembly and each of the buckets. The off-rotor power source can also be used to power devices associated with the central reservoir 572. In another embodiment, an on-rotor power source can be used, such as an electronic generator or batteries, to power the central reservoir 572 and devices on the buckets.

The configuration in FIGS. 10C and 10D includes 7 instrument mounts for different types of detectors, 550, 552, 554, 556, 558, 560 and 562. During operation all or portion of the detectors can be utilized. In FIG. 10D, for one embodiment, all of the detectors can be utilized. Thus, all of the arms associated with the detectors are shown as being engaged in FIG. 10D. In this instance, for each revolution of the rotor assembly, seven different measurements can be made for each flow cell and then repeated for each subsequent revolution.

In particular embodiments, detector 550 can be a visible and UV absorbance detector. Detector 552 can be a fluorescence detector. Detectors 554, 556, 558, 560 and 562 can be Laser-induced fluorescence (LIF) detectors. For each of the LIF detectors, a laser with a different wavelength can be employed. Further details of instrumentation, such as details regarding an absorbance detector, a fluorescence detector and a LIF detector are described in the following section.

Instrumentation

After a sample has undergone a chromatographic separation, such as one performed during rotation of one of the column as previously described, one or more detectors can be employed to identify eluents that have exited the column. In chromatography, matching a retention time of an eluent in the column to the retention time of a known eluent does not necessarily provide sufficient information to identify the eluent. Thus, additional detectors can be employed.

In chromatography, the combination of a given substance's retention time for a specific set of chromatographic parameters and the response characteristics of that specific substance for a given detector can form the basis of determining the chemical identity of that substance. Since all substances respond differently for each type of detector, the more detectors used, the more certainty there can be about the chemical identity of the substance. When these two parameters are combined with the retention time relative to one or more reference substances, the chemical identity can be determined with near certainty The detector can be a system component that emits a response due to the detection of an eluting sample compound and subsequently signals a peak on the chromatogram. Typically, the detector can be positioned immediately posterior to the stationary phase in order to detect the compounds as they elute from the column. For example, as described above, flow cells can be used with many types of optical detectors. Thus, the flow cell can be typically positioned at the end of the column.

Information generated from a detector can often be displayed as a time changing value, such as a curve with peaks and valleys that change over time as different sample components elute from a column. The width and height of the peaks can usually be adjusted using the coarse and fine tuning controls associated with the detector. Also, the detection and sensitivity parameters associated with a detector can often be controlled.

As previously described, in some embodiments, a detector and all its associated components can be located on a rotatable element, such as rotor assembly. Further, some signal processing associated with detector can also be performed on the rotor assembly. For instance, a flow cell, its associated detectors and a processor for performing signal processing associated with the detector can be located on a rotatable element, such as rotor assembly described with respect to FIGS. 2-9C or a bucket assembly described with respect to FIGS. 10A-D. In other embodiments, a portion of the detector can be located on the rotatable element and a portion can be located on a stationary off-rotor, such as the flow cells and detectors described with respect to FIGS. 2-10D. In yet other embodiments, a detector can be totally located off of the rotatable element. For example, collected fractions can be transferred off a rotatable element by some mechanism to a detector for further analysis.

There are many types of detectors that can be used with embodiments described herein. Some of the detectors that be used with the embodiments described herein include: Refractive Index (RI), Ultra-Violet (UV), Visible, Fluorescent, Radiochemical, Electrochemical, Near-Infra Red (Near-IR), Mass Spectroscopy (MS), Nuclear Magnetic Resonance (NMR), Light Scattering (LS) and combinations thereof. These detectors are described as follows.

There are two types of detectors in liquid chromatography. The first type can require direct contact of the detector's transducer with the column eluent. These include electrochemical detectors of various types and mass spectrometers. The second type does not require direct contact of any physical element of the detector with the column eluent. These can include the detectors that measure the changes in one part or another part of the electromagnetic spectrum as well as nuclear magnetic resonance detectors.

Refractive Index (RI) detectors can be used to measure the ability of analyte molecules to bend or refract light. This property for each molecule or compound is called its refractive index. For some RI detectors, such as differential RI detectors, light can proceed through a bi-modular flow-cell to a photodetector. One channel of the flow-cell can direct the mobile phase passing through the column while the other can direct only the mobile phase. Detection can occurs when the light is bent due to samples eluting from the column, which can be read as a disparity between the two channels. For other types of RI detectors the degree to which the light is refracted by the analytes as they pass through the flow cell can be detected directly without reference to another flow cell.

Ultra-Violet (UV) and Visible (Vis) light detectors can be used measure the ability of a sample to absorb light. This measurement can be accomplished at one or several wavelengths. Typically, UV detectors can have a sensitivity of about $10^{-8}$ or $10^{-9}$ gm/ml. Typically, UV detectors require a light source and light gathering element. In general, light sources can be broad spectrum lamps, emission line lamps, light emitting diodes, or even a laser. As previously described, the light emitted from the light source can be directed through a flow cell or several optical focusing or filtering elements can be used to focus the light onto the optically transparent window of the flow cell.

As examples, a fixed wavelength measurement can be used to detect absorbance at one wavelength, such as 254 nm. A variable wavelength measurement can be used to detect absorbance at different wavelengths one wavelength at a time, but over a wide range of wavelengths. For example, for the embodiment where a flow cell rotates underneath a stationary detector, a first wavelength of a light source can be used on a first revolution of a rotor assembly, a second wavelength on a second revolution and a third wavelength and then start over again with the first wavelength. This type of measurement could be repeated for many 2 or more different wavelengths and is not limited to only 3 wavelengths. In another embodiment, a diode array can be used to measure a spectrum of wavelengths simultaneously. In yet another embodiment, several different light sources with or without accompanying optical focusing elements, mounted on a fixed position relative to the rotatable element can be focused onto the flow cell such that for each revolution of the rotatable element, many different wavelengths can be used with a single common flow cell on the rotatable element.

Scanning UV/Vis detectors can be used to measure and detect samples over the entire UV to visible (UV-Vis) spectrum. They can be highly valuable tools in the identification and analysis of sample compounds. In this type of detector, the response of the substance passing through the flow cell to the light in the flow cells is measured and recorded. To detect over an entire spectrum, the detector can proceed in one of two ways. The first can be to scan across the entire spectral region, which can be accomplished by a scanning monochromator spectrometer. A standard scanning monochromator spectrometer can use a tungsten or deuterium lamp that emits a broad spectrum light source. The light can then be directed across a grating or prism which reflects the light through an exit slit to the sample cell. The sample can then detected by a photomultiplier tube. The wavelength of the light can be adjusted by rotating the grating or prism, but only one region can be scanned at a time. Subsequently, data points can be obtained at different times.

The second method can involve monitoring the entire UV-Vis region simultaneously. One technique can be to use several photomultiplier tubes positioned to detect in the spectral regions of interest. Another is to use the linear photodiode array (LPDA) spectrophotometer which measures in the 190-1100 nm region simultaneously. No monochromatic light is needed and data can be retrieved in milliseconds. This detection methodology can be used for analyzing kinetic or chemical intermediates, or separating and analyzing overlapping chromatographic peaks using spectography.

Fluorescent detectors can be used measure the ability of a compound to absorb light at a given wavelength (excitation) then re-emit light at a slightly higher wavelength. Each compound can have a characteristic fluorescence. The excitation source can pass through the flow-cell to a photodetector while a monochromator measures the emission wavelengths. Typically, fluorescent detectors can have a sensitivity limit of about $10^{-9}$ to $10^{-11}$ gm/ml.

Laser-induced fluorescence (LIF) is a spectroscopic method that can be used for detecting species. As previously described, one or more different LIF detectors can be used with the embodiments described herein. The species to be examined can be excited with monochromatic laser light. The wavelength can be often selected to be the one at which the species has its largest cross section. An excited species can, after some time, usually in the order of few nanoseconds to microseconds, de-excite and emit light at a wavelength larger than the excitation wavelength. The emitted light, fluorescence, can measured using a detector of some type.

In particular embodiments, disperse spectra and/or excitation spectra can be generated and measured. To perform a disperse spectra measurement, a fixed lasing wavelength can be used and the generated fluorescence spectrum can be analyzed. To perform an excitation spectra measurement, a lasing wavelength can be varied and fluorescent light at a fixed emission wavelength or range of wavelengths can be measured for the various lasing wavelengths.

One advantage fluorescent detectors is that it is possible to get two- and three-dimensional images since fluorescence takes place in all directions (i.e. the fluorescence signal is isotropic). Further, the signal-to-noise ratio of the fluorescence signal can be very high, providing a good sensitivity to the process. It can also be possible to distinguish between more species, since the lasing wavelength can be tuned to a particular excitation of a given species which is not shared by other species.

Radiochemical detection can involve the use of radio-labeled material, such as tritium ($^3$H) or carbon-14 ($^{14}$C). It can operate by detection of fluorescence associated with beta-particle ionization. One application can be metabolite research. Two detector types can be a) homogeneous and heterogeneous. In a homogeneous detector, a scintillation fluid can be added to a column effluent to cause fluorescence. In a heterogeneous detector, lithium silicate and fluorescence caused by beta-particle emission can interact with the detector cell. Typically, this type of detector can have sensitivity limit up to $10^{-9}$ to $10^{-10}$ gm/ml.

Electrochemical detectors can be used to measure compounds that undergo oxidation or reduction reactions. Usually, this measurement can be accomplished by measuring gain or loss of electrons from migrating samples as they pass between electrodes at a given difference in electrical potential. In particular embodiments, the electrodes can be located near the end of one or more of the columns in the configurations previously described herein, such as on a rotor assembly or a bucket assembly. Typically, this type of detector can have a sensitivity limit of about $10^{-12}$ to $10^{-13}$ gm/ml.

In a Mass Spectroscopy (MS) detector, a sample compound or molecule can be ionized. Then, it can be passed through a mass analyzer, and the ion current can be detected. There are various methods for ionization. In a first method, often referred to as Electron Impact (EI), an electron current or beam created under high electric potential can used to ionize the sample migrating off the column. In a second method, often referred to as chemical ionization, ionized gas can be used to remove electrons from the compounds eluting from the column. In a third method, often referred as Fast Atom Bombardment (FAB), xenon atoms can be propelled at high speed in order to ionize the eluents from the column. This type of detector can have detector can have detection limit of $10^{-8}$ to $10^{-10}$ gm/ml. In particular embodiments, this methodology can be performed on a rotatable element during rotation of the element.

In Nuclear Magnetic Resonance (NMR) detectors, certain nuclei with odd-numbered masses, including H and $^{13}$C, can spin about an axis in a random fashion. However, when placed between poles of a strong magnet, the spins can be aligned either parallel or anti-parallel to the magnetic field, with the parallel orientation favored since it is slightly lower in energy. The nuclei can then be irradiated with electromagnetic radiation which is absorbed and places the parallel nuclei into a higher energy state; consequently, they are now in "resonance" with the radiation. Each H or C can produce different spectra depending on their location and adjacent molecules, or elements in the compound, because all nuclei in molecules are surrounded by electron clouds which change the encompassing magnetic field and thereby alter the absorption frequency.

In light-scattering (LS) detectors, when a source emits a parallel beam of light which strikes particles in solution, some light can be reflected, absorbed, transmitted, or scattered. In Nephelometry, which can be defined as the measurement of light scattered by a particulate solution, the detection of a portion of light scattered at a multitude of angles can be detected. The sensitivity can depend on the absence of background light or scatter since the detection occurs at a black or null background.

In Turbidimetry, which can be defined as the measure of the reduction of light transmitted due to particles in solution, the light scatter as a decrease in the light that is transmitted through the particulate solution can be measured. Therefore, it can quantify the residual light transmitted. Sensitivity of this method can depend on the sensitivity of the machine employed, which can range from a simple spectrophotometer to a sophisticated discrete analyzer. Thus, the measurement of a decrease in transmitted light from a large signal of transmitted light can be limited to the photometric accuracy and limitations of the instrument employed.

Near-Infrared Detectors can operate by scanning compounds in a spectrum range, such as from 700 to 1100 nm. The stretching and bending vibrations of particular chemical bonds in each molecule can be detected at certain wavelengths. With this type of detector, multiple analyses can be obtained from a single spectrum.

Chromatographic Separation

As described above, chromatography can be described as a process that achieves physical separation of the individual components of a mixture of chemical substances. In the chromatographic process, the mixture of chemical substances can be dissolved in a carrier stream (gas or liquid). The carrier stream including the mixture can be forced through a bed of particles. The carrier stream moves at a velocity through the bed of particles. In chromatography, the carrier stream is often referred to as the "mobile phase" and the bed of particles is referred to as the "stationary phase."

In the embodiments previously described herein, chromatographic enclosures, such as cylindrical columns, are described that can contain the stationary phase for a chromatographic process. The chromatographic enclosure contains a chromatographic stationary phase. At least one flow path is provided through the chromatographic enclosure such that fluid can enter the chromatographic enclosure, pass through a chromatographic stationary phase and then exit the chromatographic enclosure.

In some embodiments, a number of separate flow paths are provided within the chromatographic enclosure where there is no fluid communication between each of the separate flow paths. A separate chromatographic stationary phase is contained in each of the flow paths. The separate flow paths allow for "parallel" chromatographic processing where in each of the flow paths, a common sample fluid or different sample fluids are processed in parallel.

A flow path is provided by a structure that includes a hollow inner portion. The fluid and the chromatographic stationary phase are contained within the hollow inner structure. Generally, the fluid is driven axially through the hollow portion of the structure. For instance, the structure can be a hollow pipe where the fluid is driven axially through the hollow pipe. A length, an inner cross section and an inner cross sectional area can be defined for hollow portion of the structure associated with each flow path in the chromatographic enclosure. In some embodiments, the inner cross sectional area is constant along the length of the flow path. In other embodiments, the inner cross sectional area varies along the length of the flow path. In some embodiments, the inner cross section is circular. In general, the inner cross sectional geometry can be any shape.

In particular embodiments, an outer cross section of the structure is similar to the inner cross section of the hollow portion of the structure. For instance, the inner and outer cross section can be circles of different diameters, such that a cylindrical pipe is formed. In other embodiments, the inner and outer cross sections are not similar. For instance, a circular hollow tube can be drilled into a rectangular block of material. In some embodiments, the chromatographic enclosure is integrally formed with a rotor or housing separate from the rotor.

Each chromatographic enclosure includes an entrance and an exit. The entrance allows fluid to enter one or more separate flow paths. The exit allows fluid to exit from one or more separate flow paths. A fluid, such as the mobile phase of a chromatographic process, can enter via the entrance and exit via the exit to establish a flow of the fluid through the chromatographic enclosure including a flow through the chromatographic stationary phase contained within the enclosure.

The chromatographic enclosures can be carried by a rotor that provides a centrifugal force to the chromatographic enclosure. For instance, as described above, the chromatographic enclosures can be carried on a rotor assembly that is arranged to rotate at an angular velocity. The centrifugal forces provide a driving a driving force for moving fluid through the chromatographic enclosure. The fluid can include a sample. As the fluid including the sample moves through the stationary phase contained in the chromatographic enclosure a chromatographic separation of the sample can occur.

As an example, FIG. 11 is a front view of a chromatographic enclosure configured for a chromatographic process before and after centrifugation. A column, such as a cylindrical plastic syringe 600, can be secured within a container, such as the centrifuge tube 604. The plastic syringe 600 can include a top opening 615 and a bottom opening 616. In this embodiment, the area of the of column changes over its length as the top opening 615 is larger than the bottom opening 616. As previously described, in other embodiments, the column can be a constant area over its length.

To set-up a chromatographic process, prior to centrifugation, a number of components can be added to the plastic syringe 600. A porous plug, such as glass wool 616, can be added near the bottom of the syringe 600. The porous plug can prevent a solid stationary phase, such as 610, from exiting the column but allow fluids to exit the column.

In one embodiment, the stationary phase can be a chromatographic adsorbent 610. The type of stationary phase that is employed can vary depending on a type of chromatographic process that is set-up. A sample can interact differently with a stationary phase material depending on a type of solvent and a type of stationary phase material that is used. Different types of chromatographic processes and a few characteristics of the stationary phase materials and solvents that are used in these processes are described below, following the description of FIG. 11.

A sample 608, which can be dissolved in a liquid, can be placed above the stationary phase. The size of the stationary phase particles can be selected such that the sample does not penetrate the stationary phase under the force of gravity alone. A porous separator, such as sand 606, can be placed above the sample 608. The separator can separate the sample from a solvent source, such as solvent reservoir 602. The solvent source can act as a mobile phase in the chromatographic process. It can be placed above the sample and the separator 606.

Next, the chromatographic process configuration can be coupled to a device that can impart an angular velocity to the configuration, such as one of the rotor assemblies previous described. Under centrifugation, the solvent in the solvent reservoir 602 and the sample 608 can be driven into the stationary phase, such as 610 and down the length of the column. The sample 608 and the solvent from the solvent reservoir 602 can move through the stationary phase during centrifugation. After a period of time, the sample 608 may have moved some distance through stationary phase 610. Thus, the stationary phase is shown above and below the sample 608. Also, a portion of the mobile phase may have passed entirely through stationary phase 610 and out the exit 616 of the column to collect, as eluent 618, in a bottom of the centrifuge tube 604.

This embodiment is provided for the purposes of illustration only and is not meant to be limiting. In the embodiment of FIG. 11, the sample can begin to move through the stationary phase prior to a steady flow being established in the column. Thus, chromatographic separation can begin prior to a steady flow being established. In previously described embodiments, a steady flow can be established in the column prior to sample introduction.

In the embodiment of FIG. 11, a solvent composition, which can be a mixture of different solvents, can be used in the solvent reservoir 602. During centrifugation, the solvent reservoir 602 is not replenished and the composition of the solvent is not changed. In previously described embodiments, during centrifugation, the solvent reservoir 602 can be replenished and the composition of the solvent can be changed, i.e., gradient elution can be employed.

Different types of chromatographic processes can be performed depending on a composition of the mobile phase and a composition of the stationary phase. The embodiments described herein are applicable to any type of chromatographic process where a mobile phase is moved through a stationary phase in a chromatographic enclosure. A few examples of chromatographic processes in which the method and apparatuses described herein can be utilized include but are not limited to partition chromatography, adsorption (liquid-solid) chromatography, ion exchange chromatography, affinity chromatography and size exclusion chromatography, such as gel permeation or gel filtration. Partition chromatography generally includes both bonded phase and adsorbed phase reversed phase partition chromatography as well as normal partition chromatography.

In adsorption chromatography, a mobile liquid or gaseous phase can be used that is adsorbed onto the surface of a stationary solid phase. The differential equilibration between the mobile and stationary phase accounts for the separation of different solutes. In partition chromatography, a thin film can be formed on the surface of a solid support by a liquid stationary phase. The thin film can be covalently bound onto the surface of the support particle (bonded phase) or adsorbed onto the surface of the support particle (non-bonded phase). Analytes can differentially equilibrate between the mobile phase and the stationary liquid. In Ion-Exchange (IEX) Chromatography, solute ions of the opposite charge in the mobile liquid phase are attracted to the resin (or particulate stationary phase) by electrostatic forces and the greater the charge of the analyte, the more the analyte interacts with the surface of the stationary phase particles and the longer it takes to traverse the chromatographic system. IEX chromatography can be also useful for determining the tertiary structure and quaternary structure of purified proteins, especially since it can be carried out under native solution conditions using only aqueous solutions.

In size exclusion chromatography, an attractive interaction between the stationary phase and solute is not used. Instead, the liquid or gaseous phase passes through a porous gel which separates the molecules according to its size. The pores are normally small and exclude the larger solute molecules, but allow smaller molecules to enter the gel, causing them to flow through a larger volume. This causes the larger molecules to pass through the column at a faster rate than the smaller ones.

In affinity chromatography, the specific interaction between one kind of solute molecule and a second molecule that is immobilized on a stationary phase can be utilized. For example, the immobilized molecule may be an antibody to some specific protein. When a solute containing a mixture of proteins are passed by this molecule, only the specific protein is reacted to this antibody, binding it to the stationary phase. This protein can later be extracted by changing the ionic strength or pH.

In more detail, Reverse Phase Partition Chromatography (RPC) can include any chromatographic method that uses a non-polar stationary phase. It differs from "normal" partition chromatography (NPC) which can be done on non-modified silica or alumina with a hydrophilic surface chemistry and a stronger affinity for polar compounds. In RPC, the introduction of alkyl chains bonded covalently to the support surface can reverse the elution order as compared to NPC. In RPC, polar compounds can be eluted first while non-polar compounds are retained—hence it is called "reversed phase."

For RPC, any inert non-polar substance that achieves sufficient surface coverage of the particles of the packing can be used. One column can be an octadecyl carbon chain (C18) bonded silica (USP classification L1), 297 columns are commercially available. Another column can be by C8 bonded silica (L7-166 columns are commercially available). Other columns can be cyano bonded silica (L10-73 columns are commercially available) and phenyl bonded silica (L11-72 columns are commercially available). C18, C8 and phenyl are dedicated reversed phase packings while cyano columns can be used in a reversed phase mode depending on analyte and mobile phase conditions. It should be noted at this point that not all C18 columns have identical retention properties. Surface functionalization of silica can be performed in a monomeric or a polymeric reaction with different short-chain organosilanes used in a second step to cover remaining silanol groups (end-capping). While the overall retention mechanism remains the same subtle differences in the surface chemistries of different stationary phases will lead to changes in selectivity.

In RPC, mixtures of water (or buffered aqueous solutions) and organic solvents can be used to elute analytes from a reversed phase column. The solvents can be miscible with water and the most common organic solvents used are acetonitrile, methanol or tetrahydrofuran (THF). Other solvents can be used such as ethanol and 2-propanol (isopropyl alcohol). Elution can be performed isocratically (the water-solvent composition does not change during the separation process) or by using a gradient (the water-solvent composition does change during the separation process). The pH of the mobile phase can have an important role on the retention of an analyte and can change the selectivity of certain analytes. Charged analytes can be separated on a reversed phase column by the use of ion-pairing (also called ion-interaction). This technique is known as reversed phase ion-pairing chromatography.

Sample Results and Comparison with HPLC

An effectiveness of chromatographic separation process is often referred to as a "chromatographic efficiency." Chromatography efficiency theory describes parameters that allow relative efficiencies of various chromatographic processes to be compared. It is believed that utilizing the methods and apparatus described herein, chromatographic processes can be set-up that are more "efficient" than similar chromatographic processes that can be performed using other types of apparatus and methods, such as chromatographic processes using HPLC. Thus, in the following paragraphs, methods and apparatus for centrifugal liquid chromatography including pressure requirements and particle size limitations are compared HPLC, which is a commonly practiced form of liquid chromatography. Further, a brief description of chromatographic separation theory is described including 1) measure performance measurements of chromatographic separation efficiencies using apparatus and methods described herein and 2) a comparison of the estimated performance measurements with performance measurements obtained with other types of chromatographic apparatus, such as HPLC.

In HPLC, a common quantity that is employed is the back pressure. A back pressure calculation can be used to determine how much pressure is needed to force a fluid through a stationary phase in a column where the stationary particles are a particular size. The required pressure in HPLC can be calculated as, $$\Delta P = (\eta F L)/(K^0 r^2 d_p^2)$$

where $\Delta P$ is the pressure at the column head which decreases across the column length, $\eta$ is the viscosity, F is the flow rate, L is the length of the column, $K^0$ is the specific permeability, r is the column radius and $d_p$ is the particle diameter. It can be seen that increasing the flow rate, a fluid viscosity and length of the column or decreasing the particle diameter all lead to greater pressure requirements. For small particle sizes, such as below 2 micrometers, in HPLC, the pressure requirements become prohibitive. For example, in HPLC, pressures above 10,000 PSI can be required to utilize 2 micrometer particles.

In the embodiments described herein using centrifugal liquid chromatography, the backpressure requirements and an importance of pressure appear to be different than HPLC. For instance, for a given particle size as well as the other parameters in the formula described above, the pressure at which the chromatographic systems described herein operate appears to be much less than what would be required in HPLC system. Also, systems using centrifugal liquid chromatography can behave differently in regards to pressure than HPLC systems. For instance, in some embodiments described herein, the pressure can increase from the head of the column along the column length rather than decrease along the column like in HPLC.

Without being bound by a particular theory, the column can be viewed as a number of layers where a fluid moves from layer to layer as it proceeds down the column. In separation efficiency theory, as is described below, each of these layers can be referred to as a "plate." When pressure is used as a driving force, such as in HPLC, it is believed a small amount of pressure is needed to move the fluid across each layer. Thus, the required pressure depends on the number of layers or plates in the column where the total required pressure can be considered as the summation of the pressures required to move the fluid across each of the layers. Separation efficiency is usually increased as the number of layers increase. Thus, in HPLC, increasing the number of layer and hence the separation efficiency can require more pressure.

In centrifugal liquid chromatography, the fluid can be moved across each layer via centrifugal forces and not a drop in pressure. The centrifugal forces can act on each layer independently of one another without necessarily requiring a pressure drop across the layer to move the fluid across the layer as in HPLC. Thus, in centrifugal liquid chromatography, the pressure requirements appear to much less than that of HPLC. Applicant believes this feature may not have been fully appreciated in the prior art.

Further, it is believed in the embodiments described herein much smaller particles can be used than are possible with HPLC. For instance, a use of particle sizes of about 15 angstroms may be possible. If smaller particles can be manufactured, than it is believed that smaller size particles can be used.

In chromatography, a plate model can be used to estimate separation efficiencies. The plate model supposes that the chromatographic column contains a large number of separate layers, called "theoretical plates." Separate equilibrations of the sample between the stationary and mobile phase can occur in these "plates". The analyte moves down the column by transfer of equilibrated mobile phase from one plate to the next.

The term "plate" is used as an analogy for the processes at work in the column as "plates" do not actually exist in the column. The column efficiency, i.e., its ability to perform chromatographic separation can be quantified by determining a number of theoretical plates in the column, N, or by stating the plate height, which is often referred to as Height Equivalent to a Theoretical Plate (HETP). For column of length, L, HETP can be defined as, $$HETP = L/N.$$

When comparing chromatographic processes occurring in two different columns, a larger value of N or a smaller value of HETP for a first column as compared to a second column can indicate that the first column has a greater chromatographic efficiency than the second column.

A definition of separation efficiency has been developed for liquid chromatography taking place in a column. The International Union of Pure and Applied Chemistry defines separation efficiency as:

$$N = 16(V_R/w_b)^2 = 16(t_r/w)^2$$

where N is the number of theoretical plates, $V_R$ is the volume of mobile phase entering the column between sample injection and the emergence of the peak maximum of the sample component of interest, $w_b$ is the total volume from the time the analyte begins emerging from the column to the time it has completely left the column or t is the retention time (seconds) and w is the width of the peak (seconds).

Experimental Measurements were made using a chromatographic system for one embodiment described herein. For a separation of three species, a column length of 2.3 cm, packed with a particle size of diameter of 5 micrometers, ($d_p$) and a void volume of 0.110 ml is utilized. Species 1 is FD&C Red No. 3 (Erythrosine). Species 2 is FD&C Yellow No. (Tartrazine). Species 3 is FD&C Green No. 3 (Fast Green FCF, E143). The mobile phase is 70% Water, 30% Isopropyl Alcohol (IPA), and 0.010 molar Tetrabutylammonium Phosphate (TBAP). In this experiment, a theoretical plate height is generated. These experiments resulted in the following values as shown in Table 1.

TABLE 1

Experimentally Measured Values

| Species | $V_R$ (ml) | $w_b$ (ml) | k | α (1, 2) (1, 3) (2, 3) | R (1, 2) (1, 3) (2, 3) | N (Column) | N/L (meter) |
|---|---|---|---|---|---|---|---|
| 1 | 5.3 | .009 | 47.2 | 1.15 | 94.1 | 5,548,642 | 2,412,453,033 |
| 2 | 6.1 | .008 | 54.5 | 1.42 | 244.4 | 9,302,500 | 4,044,565,217 |
| 3 | 7.5 | .009 | 67.2 | 1.23 | 164.7 | 11,111,111 | 4,830,917,874 |

$V_R$ and $w_b$, which is a value for each species, are described above with regard to the theoretical plate formula. k' is a capacity factor for each species, α is the ratio of retention volumes between two species and R is a resolution between two species, N is the number of theoretical plates and N/L is the number of theoretical plates normalized by the length of the column (0.023 m). Resolution between two species, such as between species 1 and 2, described above can be calculated as $R(A,B) = 2[V_{R-B} - V_{R-A}]/[w_{b-B} + w_{b-A}]$. For example, $R(1,2) = [V_{R-2} - V_{R-1}]/[w_{b-2} + w_{b-1}]$. $α(A,B) = k'_A/k'_B$ is a ratio of capacity factors between two species. For instance, $α(1,2) = k'_1/k'_2$.

Figure 12:
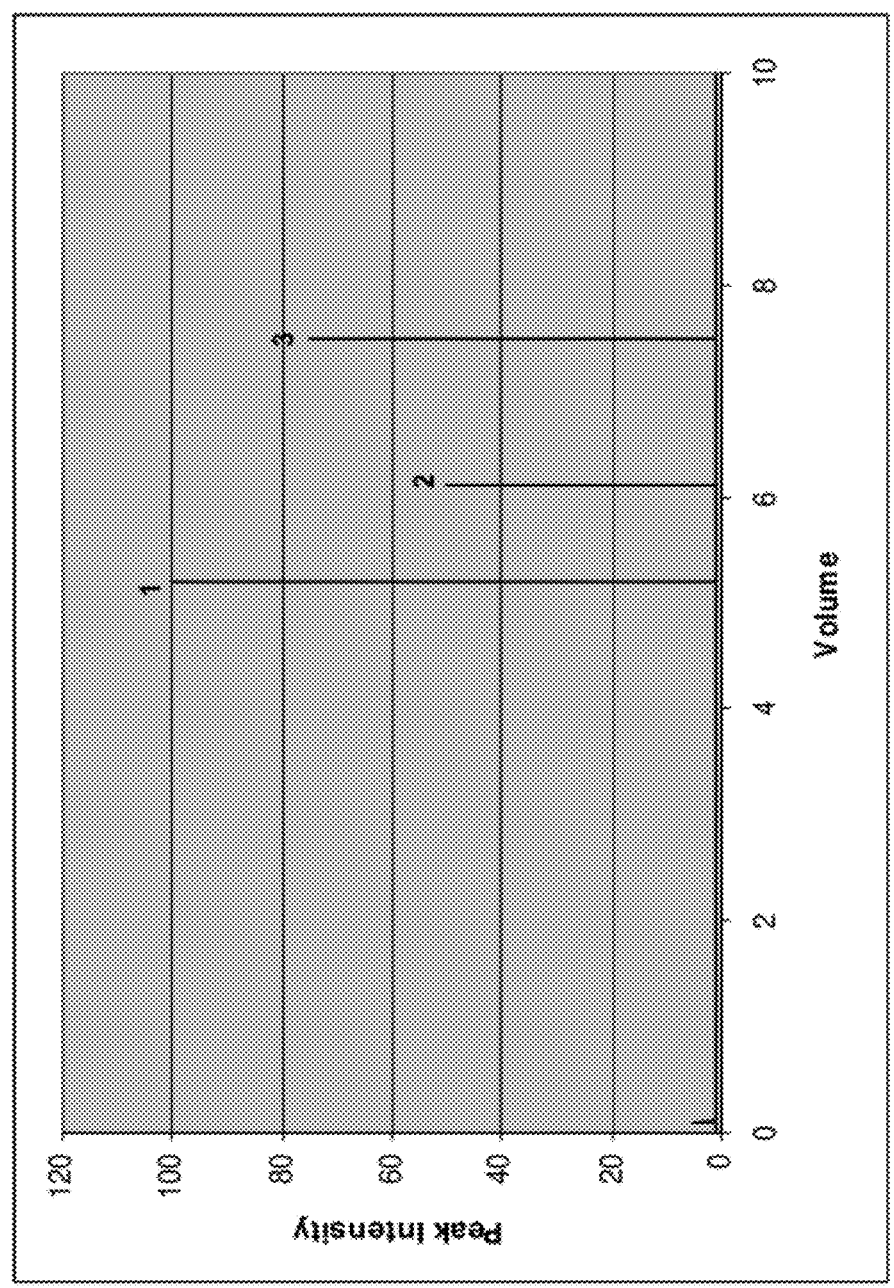
FIG. 12 is a chromatogram for a separation of 3 species.

A chromatogram with the 3 species described in Table 1 is shown in FIG. 12. The quantities derived in Table, such as theoretical plates, can be derived from data obtained from the chromatogram, such as a Volume of each peak. Although appearing as lines, on the smaller scale, the peaks have a width and can be used to calculate a volume.

The theoretical plates for each species and resolution between species are quite high. For instance, a resolution value between two species of 1.5 or greater is considered completely separated. The theoretical plate values and resolution values appear to be much higher than theoretical plate values and resolution values obtained using HPLC.

To quantify the differences between HPLC and the methods and apparatus described herein, a comparable separation was performed in HPLC and then using centrifugal liquid chromatography. Each separation used 5 micrometer diameter particles in the stationary phase. A length of the column used in the HPLC was 150 mm. A length of the column used with the centrifugal liquid chromatography was 36 mm. A similar mobile phase fluid and sample were used in both methods. Measured results for the experiments are shown in Table 2.

TABLE 2

Experimentally Measured Values

| Methodology | N (Column) | N/L (meter) | HETP |
|---|---|---|---|
| HPLC | 9,604 | 64,027 | 16 micrometers |
| Centrifugal Liquid Chromatography | 17,650,317 | 490,286,583 | about 2 nanometers |

The large differences between HPLC and the centrifugal liquid chromatography measurement were unexpected. The centrifugal liquid chromatography measurements indicate separation efficiencies that are orders of magnitude better than HPLC. There are number of possible explanations for the increased separation efficiencies of centrifugal liquid chromatography. Without being bound by a particular theory as to why the exemplary results are obtained, a few observations can be made as follows.

Diffusion resulting from concentration gradients appears to be much lower when centrifugation is used to drive a flow through a chromatographic enclosure as compared to using pressure as in HPLC. Reduced diffusion can increase separation efficiency hence contribute to the large number of theoretical plates obtained with the embodiments described herein as opposed to HPLC. Sedimentation coefficients associated with centrifugation are concentration dependent. This effect may contribute to a decrease in diffusion obtained with centrifugation.

Applications

Chromatography is a fundamental tool for practicing chemists as well as others who are applying chemistry in their own discipline. Chromatography is widely used in and essential to the petroleum industry, food industry, pharmaceutical industry, medicine (e.g., diagnostics), and many others. In more detail, the embodiments described herein can be used for chromatographic processes applied to:

Medical and biomedical research
    Quality control of pharmaceuticals
    Routine clinical determination
    Drug screening Space-related research and development
Geochemical research and development
Pharmaceutical research and development
Forensic sciences
Food and cosmetic chemical measurement
Process control in the petroleum industry
Environmental monitoring and pollution control
Investigation of the chemistry and metabolism of biological systems A few specific types of analyses that can be performed using the devices described herein include but are not limited to the analysis of human plasma proteins, nucleotides and their derivatives, amino acids and their derivatives, urinary metabolites, therapeutic drug monitoring, monitoring for drugs of abuse, and the analysis of the proteins of wheat and other seeds.

Two main goals of a chromatographic process, distinguished by their scale and purpose, can be analytical and preparative. Preparative chromatography can be used for large scale recovery and purification of a few samples. Analytical chromatography can be used to the small scale analysis of many samples to determine their composition and purity. A few examples of the samples size, column length and column inner diameter (I.D.) that can be involved in different preparative and analytical applications are described as follows,

| Name | Purpose | Scale | Column Length | Column I.D. |
| --- | --- | --- | --- | --- |
| Micro-Analytical | Data and some limited compound collection | nanograms to micrograms | 10-400 cm | .1-2 mm |
| Analytical | Data and some limited compound collection(compound identification and concentration) | micrograms to milligrams | 10-25 cm | 2-5 mm |
| Semi-preparative | Data and a small amount of purified compound | a few milligrams to a few hundred milligrams | 10-100 cm | 5-25 mm |
| Preparative | Larger amounts of purified compound | a few hundred milligrams to a few grams | 50-200 cm | 25-100 mm |
| Process | (Industrial) Manufacturing quantities | a few grams to a several kilograms | 100-250 cm | 100-2000 mm |

The embodiments described herein can be used for both preparative and analytical applications involving sample sizes that vary and scale accordingly, such as the applications described above. In situations involving larger samples, such as industrial processes, the apparatus and methods can be scaled up according. Column sizes, such as column length and a column I.D., which can vary depending on the application, as shown above, can range from 10-400 cm and 0.1-2000 mm, respectively, in various embodiments. The column length and I.D. can be configured to many different sizes to satisfy the requirements of a particle application. For instance, capillary tubes with a I.D. of 0.01 mm or less can be used. Thus, the ranges described above are not meant to limiting and are provided for the purposes of illustration only. Rotatable elements, such as rotor assemblies described above, can be scaled up or down, to accommodate columns of a particular size that are utilized in a particular application.

Methods

Figure 13:
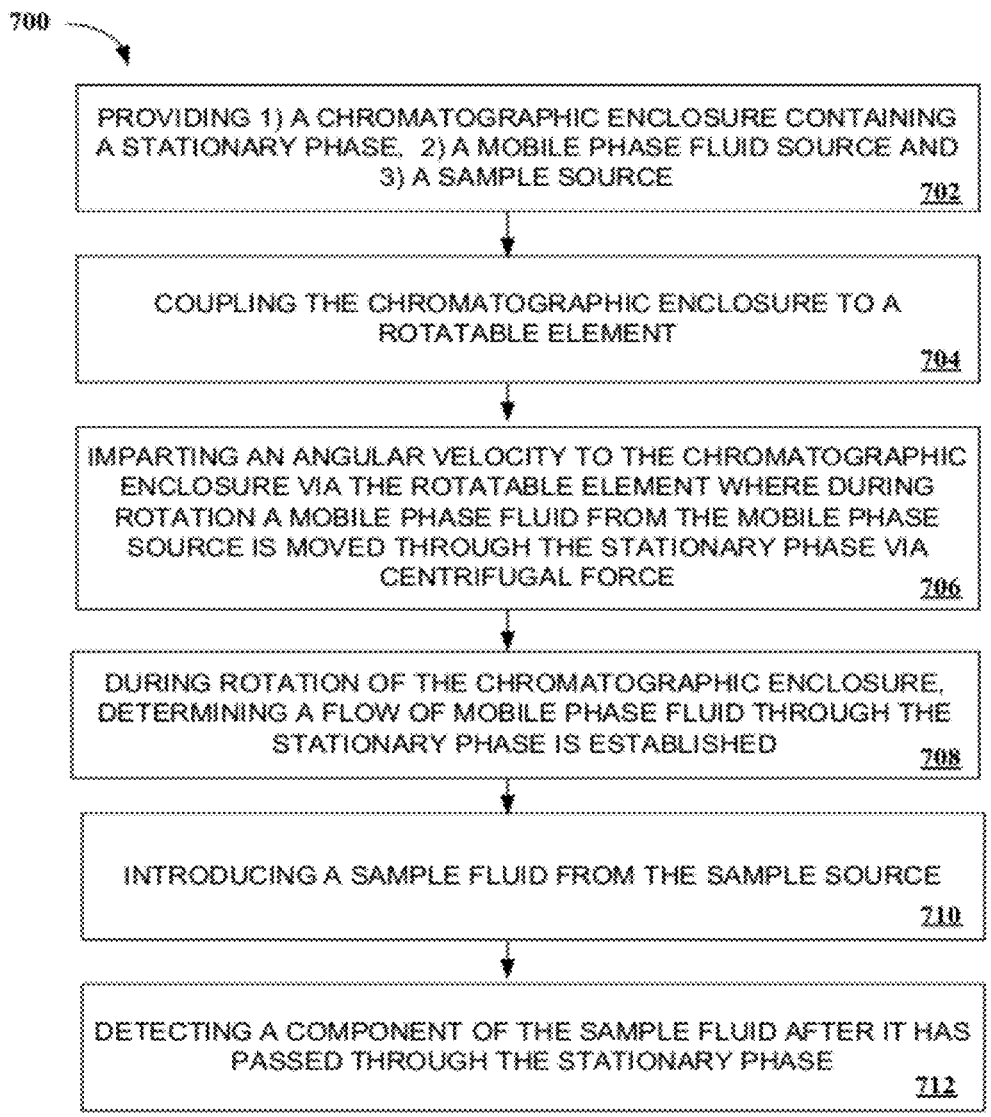
FIG. 13 is a flow chart of a method for performing a chromatographic separation process.

FIG. 13 is a flow chart of a method 700 for performing a chromatographic separation process. In 702, a number of components, such as 1) a chromatographic enclosure including a stationary phase, 2) a mobile phase fluid source and 3) a sample source can be provided. In 704, the chromatographic enclosure can be coupled to a rotatable element, such as a rotor assembly.

In 706, the rotatable element can be rotated from rest such that an angular velocity is imparted to the chromatographic enclosure. During rotation, a mobile phase fluid from the mobile phase fluid source can be moved through the stationary phase via centrifugal force. The mobile phase fluid source can be an integral component of the chromatographic enclosure or can be located separately from the chromatographic enclosure.

In 708, during rotation of the chromatographic enclosure, it can be determined whether a flow of the mobile phase fluid through the stationary phase is established. In particular, it can be determined that a steady flow is established through the chromatographic enclosure. In one embodiment, measurements made using a flow cell located near the end of the chromatographic enclosure can be used to determine whether the flow is established.

In general, a detector can be used to determine whether a steady condition has been reached in a column. Examples of detectors that can be utilized are described above, such as the detectors described in the instrumentation section. A signal from the detector can be examined over some time period, such as the signal generated from a mobile phase fluid leaving the column. The chromatogram shown in FIG. 12 is an example of a signal that can be obtained from a detector. Some noise can be associated with the signal. Steadiness can be defined as the average value of the signal varying less than some amount over a time period of interest. Multiple detectors can be associated with a column and signals from multiple detectors can be used to determine whether a steady condition has been reached.

Another factor that can be examined is the angular velocity of the rotor assembly. In some embodiments, the rotor assembly can be spun up from rest to a target angular velocity for a particular run or the rotor assembly can be at a first angular velocity for a first run and then its velocity can be increased or decreased to a new target value for a subsequent run. A detector can be used to determine whether the average angular velocity of the rotor assembly is within some range over some time period. For instance, a motor associated with the rotor assembly can report its speed. Until the average angular velocity is determined to be in range over a time period of interest, in some embodiments, sample injection may not proceed. In some embodiments, prior to initiating sample injection, a combination of signals from one or more detectors associated with a flow through a column and a signal associated with an angular velocity may both have to be within a range over a time period.

As an example, a series of runs on a chromatographic system can involve first introducing a mobile phase fluid into a column. The composition of the mobile phase fluid can produce a first signal that is output from the detector. When this signal is varying within a certain range over time, such as the signal value level is relatively flat, a sample can be injected and a gradient elution can be performed. In some instances, the gradient elution can be required to allow certain analytes to leave the column. The gradient elution can produce a signal change output from the detector. The signal change resulting from elution can have a recognizable profile, such as a line with a particular slope. Also, analytes leaving the column can produce a signal change. The signal change from the analytes can have a recognizable profile, such as peaks and valleys. The signal change produced by the analytes can have a profile that differs from the signal change produced by gradient elution, which allows in some instances, their individual contributions to the signal change to be recognized.

After the gradient elution is completed, the mobile phase fluid can be returned to its initial composition prior to the gradient elution. In response, the signal from the detector can return to its initial value of after time period, i.e., the value before gradient elution began. In some embodiments, 10-20 column volumes of fluid may be allowed to proceed through the column. When the signal returns to its initial value and its value is within some range over some time period, then, the column can be considered ready for another sample injection.

In 710, during rotation of the chromatographic enclosure, a sample fluid from the sample source can be introduced such that the sample fluid can move through the stationary phase. The movement of the sample fluid through the stationary phase can result in a chromatographic separation of one or more sample components from the sample fluid. In 712, during rotation of the chromatographic enclosure, a separated component of the sample fluid after it has passed pass through the stationary phase can be detected. For example, the separated component can pass through a flow cell near the end of the chromatographic enclosure where measurement performed using the flow cell can be used to detect a presence of the separated component. The measurement can be displayed as a chromatogram on an output device associated with the chromatographic system.

The advantages of the invention are numerous. Different aspects, embodiments or implementations may yield one or more of the following advantages. One advantage is that using centrifugation to drive fluid through a chromatographic column can allow smaller particle stationary phase particles to be used than other types of chromatographic methodologies, such as HPLC. The use of smaller particles can provide for greater chromatographic separation efficiencies than are possible with other types of chromatographic methodologies, such as HPLC. Another advantage is that the rotor assemblies described herein can allow for a large number of chromatographic processes to be performed simultaneously. The "parallel processing" of a large number of chromatographic processes can provide for shorter throughput times that enable analyses that are too time consuming and cost prohibitive to be carried out with other chromatographic processes, such as HPLC, to be performed. The many features and advantages of the present invention are apparent from the written description and, thus, it is intended by the appended claims to cover all such features and advantages of the invention. Further, since numerous modifications and changes will readily occur to those skilled in the art, the invention should not be limited to the exact construction and operation as illustrated and described. Hence, all suitable modifications and equivalents may be resorted to as falling within the scope of the invention.

What is claimed is:

1. A chromatographic system comprising:
   a chromatographic enclosure said chromatographic enclosure being arranged to contain an associated chromatographic stationary phase and to facilitate transmission of a fluid through the chromatographic stationary phase contained within the chromatographic enclosure;
   a rotor that carries the chromatographic enclosure wherein the rotor is configured to rotate the chromatographic enclosure at an angular velocity such that fluid is driven through chromatographic enclosure including through the chromatographic stationary phase via centrifugal force; and
   a fluid enclosure including a first portion configured to remain stationary while the rotor is rotating and a second portion, carried on the rotor, configured to rotate with the rotor wherein the fluid enclosure is in fluid communication with the chromatographic enclosure, and wherein the fluid enclosure is a mobile phase fluid reservoir arranged to hold a mobile phase fluid intended for delivery to the chromatographic enclosure on the rotor.

2. A centrifugal chromatographic system as recited in claim 1 further comprising an eluent reservoir arranged to hold an eluent that has passed through the chromatographic enclosure on the rotor, wherein the eluent reservoir includes a first eluent reservoir portion arranged to remain stationary and a second eluent reservoir portion arranged to rotate with the rotor.

3. A chromatographic system as recited in claim 1 wherein the first portion of the fluid enclosure further comprises a gas bearing.

4. A chromatographic system as recited in claim 1, wherein the second portion of fluid enclosure further comprises a surface on which the gas bearing sits while the second portion is rotating.

5. A chromatographic system as recited in claim 1, wherein during rotation of the rotor a force is transmitted through the first portion of the fluid enclosure to the second portion of the fluid enclosure wherein the force stabilizes the rotor.

6. A centrifugal chromatographic system as recited in claim 1, wherein the chromatographic enclosure is arranged to contain an associated chromatographic stationary phase and to facilitate transmission of a fluid through the chromatographic stationary phase contained within the chromatographic enclosure wherein the fluid is driven through the chromatographic stationary phase via centrifugal force generated from the rotation of the rotor.

7. A centrifugal chromatographic system as recited in claim 1, wherein the rotor carries a plurality of chromatographic column enclosures.

8. A centrifugal chromatographic system as recited in claim 7, further comprising at least one mobile phase fluid reservoir in fluid communication with one or more of the chromatographic enclosures.

9. A centrifugal chromatographic system as recited in claim 1, further comprising at least one sample introduction mechanism in fluid communication with the chromatographic enclosure, said sample introduction mechanism being arranged to introduce a sample fluid to the chromatographic enclosure while the rotor is rotating.

10. A centrifugal chromatographic system as recited in claim 9, further comprising a controller arranged to automatically trigger the introduction of the sample fluid into the chromatographic enclosure.

11. A centrifugal chromatographic system as recited in claim 1, further comprising a rotor drive system for imparting angular velocity to the rotor.

12. A centrifugal chromatographic system as recited in claim 1, further comprising at least one eluent reservoir in fluid communication with the chromatographic enclosure for receiving fluids eluted from the chromatographic enclosure.

13. A centrifugal chromatographic system as recited in claim 1, wherein the mobile phase fluid is compatible with a chromatographic process performed in the chromatographic enclosure and wherein the chromatographic process includes one or more of reversed-phase partitioning, adsorption, anion exchange, cation exchange, size exclusion, gel filtration, affinity interactions or combinations thereof.

14. A centrifugal chromatographic system as recited in claim 1 further comprising a mixing chamber carried by the rotor and arranged to mix the mobile phase fluid with the sample fluid on the rotor to create a mixed fluid, wherein the mixing chamber utilizes the rotation of a component carried by the rotor to enhance the mixing of the sample fluid with the mobile phase fluid, the mixing chamber being located upstream of the chromatographic enclosures.

15. A centrifugal chromatographic system as recited in claim 14 further comprising a plurality of chromatographic enclosures wherein the mixing chamber is in fluid communication with each of the plurality of chromatographic enclosures.

16. A centrifugal chromatographic system as recited in claim 1 further comprising a fluid reception mechanism configured to remain stationary and to receive, while the rotor is rotating, fluid exiting from the rotor that has passed through the chromatographic enclosure.

17. A centrifugal chromatographic system as recited in claim 16 wherein the fluid reception mechanism is a fluid collection ring.

18. A centrifugal chromatographic system as recited in claim 1 further comprising an enclosed flow path on the rotor configured to contain a fluid including the mobile phase fluid and/or sample fluid under pressure, the enclosed flow path including 1) a first segment including the chromatographic enclosure for receiving the fluid from an entrance to the flow path and communicating the fluid away from an axis of rotation for the rotor and through the chromatographic enclosure and 2) a second segment in fluid communication with the first segment for communicating the fluid toward the axis and out an exit to the flow path, said exit located at a first radial distance from the axis, such that during a rotation of the rotor the fluid continually drains from the exit when a fluid level in the first segment is located at a second radial distance from the axis less than the first radial distance wherein centrifugal force increases as the radial distance from the axis increases.

19. A centrifugal chromatographic system as recited in claim 1 further comprising a fluid enclosure including a first portion configured to remain stationary while the rotor is rotating and a second portion, carried on the rotor, configured to rotate with the rotor wherein the fluid enclosure is in fluid communication with the chromatographic enclosure and wherein the mobile phase fluid and/or the sample fluid is received in the fluid enclosure prior to entering the chromatographic enclosure.

20. A centrifugal chromatographic system as recited in claim 1 further comprising a controller configured to determine whether an approximately steady mobile phase fluid flow condition has been reached on the rotor; and a trigger a release of the sample fluid after it is determined that a steady mobile phase fluid flow condition has been reached.

21. A centrifugal chromatographic system comprising:
a rotor that carries at least one chromatographic enclosure wherein the rotor is configured to rotate the chromatographic enclosure such that fluid is driven through at least one chromatographic enclosure by centrifugal force; and
a fluid delivery mechanism in fluid communication with the chromatographic enclosure to facilitate the delivery of a mobile phase fluid to the chromatographic enclosure, wherein the fluid delivery mechanism includes a first portion configured to remain stationary while the rotor is rotating and a second portion carried on the rotor and configured to rotate with the rotor, the fluid delivery mechanism being arranged so that fluid can be passed from the first portion to the second portion of the fluid delivery mechanism while the rotor is rotating, and wherein the fluid delivery mechanism includes a mobile phase fluid reservoir arranged to hold a mobile phase fluid intended for delivery to the chromatographic enclosure on the rotor.

22. A chromatographic system as recited in of claim 21, further comprising a fluid conduit coupled to the stationary first portion of the fluid delivery mechanism configured to deliver the fluid to the second portion of the fluid delivery mechanism.

23. A chromatographic system as recited in of claim 21, further comprising a plurality of fluid conduits coupled to the stationary first portion of the fluid delivery mechanism configured to deliver the fluid to the second portion of the fluid delivery mechanism.

* * * * *